US012649845B2

(12) United States Patent
Kawai et al.

(10) Patent No.: US 12,649,845 B2
(45) Date of Patent: Jun. 9, 2026

(54) LIGHT-RESISTANT, HEAT-RESISTANT AND DURABLE ULTRAVIOLET ABSORBER

(71) Applicant: MIYOSHI OIL & FAT CO., LTD., Tokyo (JP)

(72) Inventors: Koji Kawai, Tokyo (JP); Akira Yashita, Tokyo (JP); Nobuhiro Kaneko, Tokyo (JP); Kotaro Kaneko, Tokyo (JP)

(73) Assignee: MIYOSHI OIL & FAT CO., LTD., Tokyo (JP)

( * ) Notice: Subject to any disclaimer, the term of this patent is extended or adjusted under 35 U.S.C. 154(b) by 751 days.

(21) Appl. No.: 17/417,747

(22) PCT Filed: Dec. 19, 2019

(86) PCT No.: PCT/JP2019/049869
§ 371 (c)(1),
(2) Date: Jun. 23, 2021

(87) PCT Pub. No.: WO2020/137819
PCT Pub. Date: Jul. 2, 2020

(65) Prior Publication Data
US 2022/0073702 A1     Mar. 10, 2022

(30) Foreign Application Priority Data
Dec. 26, 2018     (JP) ................................. 2018-242938

(51) Int. Cl.
*G02B 5/00*          (2006.01)
*C07D 249/20*     (2006.01)
(Continued)

(52) U.S. Cl.
CPC ............ *C08K 5/378* (2013.01); *C07D 249/20* (2013.01); *C08J 5/18* (2013.01); *G02B 5/003* (2013.01); *G02B 5/208* (2013.01); *C08J 2333/04* (2013.01)

(58) Field of Classification Search
CPC ......... C08K 5/378; C08J 5/18; C08J 2333/04; G02B 5/003; G02B 5/208; C07D 249/20
See application file for complete search history.

(56) References Cited

U.S. PATENT DOCUMENTS

| | | | | |
|---|---|---|---|---|
| 5,410,071 A | * | 4/1995 | DesLauriers | ........ C07D 249/20 548/259 |
| 5,942,626 A | * | 8/1999 | Winter | ................. C07D 249/20 548/259 |

(Continued)

FOREIGN PATENT DOCUMENTS

| | | |
|---|---|---|
| CN | 106687550 A | 5/2017 |
| EP | 0599269 A1 | 6/1994 |

(Continued)

OTHER PUBLICATIONS

Polymeric Materials Science and Engineering 2000 Volume 83, pp. 126-128.

(Continued)

*Primary Examiner* — Bijan Ahvazi
(74) *Attorney, Agent, or Firm* — Fox Rothschild LLP

(57) ABSTRACT

Provided is an ultraviolet absorber capable of efficiently absorbing harmful lights in a wavelength region of 380 to 400 nm; and suppressing the absorption of lights having a wavelength of not shorter than 400 nm, which constitutes the cause of yellowing at early stages. The ultraviolet absorber can thus be used to produce a member superior in appearance as being less affected by harmful lights, and has an (Continued)

excellent light resistance, heat resistance and durability accordingly. The highly light-resistant ultraviolet absorber of the present invention is comprised of a 2-phenylbenzotriazole derivative that contains a thioaryl ring group or the like and is represented by, for example, the following formula (1):

$$PhBzT^{1a}\text{---}S\text{---}X^{1a}\text{---}(R^{1a})_l \tag{1}$$

wherein $PhBzT^{1a}$ represents a substituted or unsubstituted 2-phenylbenzotriazole skeleton bonded to a thioaryl ring group ($\text{---}S\text{---}X^{1a}\text{---}$ . . . ), $X^{1a}$ represents a residue of a phenyl ring or the like, each of 1 $R^{1a}$s independently represents, for example, a hydrocarbon group having 1 to 18 carbon atoms, l represents an integer of 0 to 5.

10 Claims, 4 Drawing Sheets

(51) Int. Cl.
| | |
|---|---|
| *C08J 5/18* | (2006.01) |
| *C08K 5/378* | (2006.01) |
| *G02B 5/20* | (2006.01) |

(56) References Cited

U.S. PATENT DOCUMENTS

| | | | | |
|---|---|---|---|---|
| 2004/0259031 A1* | 12/2004 | Watanabe | ............. | G11B 7/254 |
| 2018/0134872 A1* | 5/2018 | Shishino | ................ | C08K 5/378 |
| 2020/0325107 A1* | 10/2020 | Kaneko | ................ | C07D 249/20 |

FOREIGN PATENT DOCUMENTS

| | | | | | | |
|---|---|---|---|---|---|---|
| EP | 3578550 | A1 | | 12/2019 | | |
| EP | 3712138 | A1 | | 9/2020 | | |
| JP | H06-505744 | A | | 6/1994 | | |
| JP | H08067813 | A | | 3/1996 | | |
| JP | 2009-184882 | A | | 8/2009 | | |
| JP | 2018-122449 | A | | 8/2018 | | |
| JP | 2018-122450 | A | | 8/2018 | | |
| JP | 2019-210289 | A | | 12/2019 | | |
| JP | 2020105022 | A | * | 7/2020 | ............. | B32B 17/06 |
| WO | 2016021664 | A1 | | 2/2016 | | |
| WO | 2016174788 | A1 | | 11/2016 | | |

OTHER PUBLICATIONS

Chinese Office Action mailed Aug. 10, 2022 in CN 201980083224.4.

Suhadolnik Jseph C. et al.: "Unexpected electronic effects on benzotriazole UV absorber photostability: Mechanistic implications beyond excited state intramolecular proton transfer", Journal of Coatings Technology, col. 74, Jan. 2002, pp. 55-61.

* cited by examiner

LIGHT-RESISTANT, HEAT-RESISTANT AND DURABLE ULTRAVIOLET ABSORBER

CROSS-REFERENCE TO RELATED APPLICATIONS

This application is a § 371 national phase entry of International Patent Application No. PCT/JP2019/049869, filed on Dec. 19, 2019, which claims priority to and the benefit of Japanese Patent Application No. 2018-242938 filed on Dec. 26, 2018, both of which are hereby incorporated herein by reference in their entireties.

TECHNICAL FIELD

The present invention relates to an ultraviolet absorber, especially an ultraviolet absorber having an excellent light resistance or heat resistance, and further having both of an excellent light resistance and heat resistance as a durability.

BACKGROUND ART

Resin members deteriorate due to the action of ultraviolet rays, and undergo quality deterioration such as discoloration and a degradation in mechanical strength, which hinders the long-term use thereof. In addition, in terms of reducing health risks such as sunburn and eye tissue damage, and further imparting optical functions, various studies have been conducted on adding an ultraviolet absorber to organic and inorganic members to shield and absorb ultraviolet rays (Patent document 1).

In recent years, in order to further enhance the effects of, for example, suppressing quality deterioration of members and preventing health problems, desired is an ultraviolet absorber capable of efficiently absorbing lights in a longer-wavelength region (380 to 400 nm), but suppressing the absorption of visible lights having a wavelength longer than 400 nm (up to 500 nm), so that yellowing of a member to which the ultraviolet absorber has been added can be suppressed, and a favorable appearance at early stages can be achieved. However, for example, the problems with a conventional benzotriazole derivative are that when it is to sufficiently absorb lights in a long-wavelength region (380 to 400 nm), the absorption efficiency in such wavelength region is low so that the benzotriazole derivative needs to be added in a large amount; and that due to the optical properties thereof, lights having a wavelength longer than 400 nm will also be absorbed massively so that a member to which the benzotriazole derivative has been added will undergo yellowing.

Particularly, the inventors of the present invention have proposed a 2-phenylbenzotriazole derivative having a sulfur-containing group, as an ultraviolet absorber capable of efficiently and sufficiently absorbing harmful lights having a wavelength of 380 to 400 nm and suppressing the absorption of lights having a wavelength of not shorter than 400 nm which constitutes the cause of yellowing at early stages (Patent documents 2 and 3). Due to its optical properties, this ultraviolet absorber can sufficiently absorb lights in a wavelength region of 250 to 400 nm; has a high ultraviolet absorption effect (molar extinction coefficient) so that the lights in such wavelength region can be efficiently absorbed even when the ultraviolet absorber is added in a small amount; and is capable of suppressing the absorption of lights having a wavelength of not shorter than about 400 nm as this ultraviolet absorber exhibits an absorption peak gradient at 350 to 390 nm that is larger than that exhibited by a conventional ultraviolet absorber so that early-stage yellowing of a member containing the ultraviolet absorber can be suppressed.

Meanwhile, other than such optical properties in terms of absorption wavelength, desired is a type of ultraviolet absorber that has an excellent affinity with organic and inorganic materials, does not bleed out from an organic or inorganic material composition containing the ultraviolet absorber, and is superior in maintaining the appearance of an organic or inorganic material. Further, it is required that the light resistance of an ultraviolet absorber be improved such that a long-term use thereof will not be hindered by, for example, a quality deterioration in light absorption capability or the like after being exposed to ultraviolet rays for a long period of time. In addition, an excellent heat resistance is also required so that, for example, discoloration, weight reduction and a deterioration in light absorption capability that are caused by thermal decomposition will not occur when placed under a high-temperature environment at a given temperature for a long period of time in a production process or in practical use settings when, for example, a resin material is being molded or dried; thus, desired is a highly durable ultraviolet absorber superior in both light resistance and heat resistance in view of a time period from production to actual use. Moreover, even in the case of an organic or inorganic material composition containing an ultraviolet absorber, desired is a type of ultraviolet absorber capable of being used to produce an organic or inorganic material composition having an excellent heat resistance in addition to an excellent light resistance where there will not be observed a discoloration, deterioration in ultraviolet absorption capability and deterioration in transparency over a long period of use.

PRIOR ART DOCUMENTS

Patent Documents

Patent document 1: JP-A-2009-184882
Patent document 2: WO2016/021664
Patent document 3: WO2016/174788

SUMMARY OF THE INVENTION

Problems to be Solved by the Invention

Patent documents 2 and 3 mainly discuss solving the problems of sufficiently and efficiently absorbing lights having a wavelength of 380 to 400 nm and suppressing early-stage yellowing by mainly employing an absorber whose basic skeleton in the sulfur-containing group is an alkyl group. However. Patent documents 2 and 3 do not at all discuss a light resistance, and even a durability including a heat resistance in addition to the light resistance of a 2-phenylbenzotriazole derivative that contains a thioaryl ring group or a thiocyclohexyl ring group.

The present invention was made in view of the above circumstances, and it is an object the present invention to provide an ultraviolet absorber capable of minimizing the impact of harmful lights by efficiently absorbing harmful lights in the wavelength region of 380 to 400 nm and suppressing the absorption of lights having a wavelength of not shorter than 400 nm which constitutes the cause of early-stage yellowing, having a favorable affinity with organic materials and inorganic materials such as glass so that a member having a superior appearance can be produced therewith; and having an excellent light resistance or heat resistance, or an excellent light resistance and heat resistance, that is, an excellent durability. It is also an object of the present invention to obtain an ultraviolet absorber-containing organic material composition where the ultraviolet absorber therein will not bleed out, the composition has an excellent affinity with the ultraviolet absorber so that the appearance of the composition can be maintained in a superior manner, and especially when the appearance thereof is transparent, such transparency can be maintained in a superior manner by suppressing yellowing. It is yet another object of the present invention to provide an ultraviolet absorber capable of being used to even produce an organic material composition that is superior in light resistance and heat resistance, that is, durability in a way such that, for example, a discoloration, deterioration in ultraviolet absorption capability and deterioration in transparency will not occur over a long period of use.

Means to Solve the Problems

In order to solve the above problems, [I] a highly light-resistant ultraviolet absorber of the present invention is characterized by comprising a 2-phenylbenzotriazole derivative that contains a thioaryl ring group or thiocyclohexyl ring group and is represented by any one of the following formulae (1) to (4):

[Chemical formula 1]

$$\text{PhBzT}^{1a}\text{—S—X}^{1a}\text{—(R}^{1a}\text{)}_l \tag{1}$$

wherein $\text{PhBzT}^{1a}$ represents a substituted or unsubstituted 2-phenylbenzotriazole skeleton bonded to a thioaryl ring group (—S—$\text{X}^{1a}$— . . . ), $\text{X}^{1a}$ represents a residue of a phenyl or naphthyl ring, each of l $\text{R}^{1a}$s independently represents a hydrocarbon group having 1 to 18 carbon atoms, an alkoxy group having 1 to 18 carbon atoms or a hydroxy group, l represents an integer of 0 to 5;

[Chemical formula 2]

$$\text{PhBzT}^{1b}\text{—S—Cy—(R}^{1b}\text{)}_m \tag{2}$$

wherein $\text{PhBzT}^{1b}$ represents a substituted or unsubstituted 2-phenylbenzotriazole skeleton bonded to a thiocyclohexyl ring group (—S-Cy- . . . ), Cy represents a cyclohexyl ring residue, each of m $\text{R}^{1b}$s independently represents a hydrocarbon group having 1 to 18 carbon atoms, an alkoxy group having 1 to 18 carbon atoms or a hydroxy group, m represents an integer of 0 to 5;

[Chemical formula 3]

$$\text{PhBzT}^{1c}\text{—S—A}^{1c}\text{—S—PhBzT}^{2c} \tag{3}$$

wherein each of $\text{PhBzT}^{1c}$ and $\text{PhBzT}^{2c}$ independently represents a substituted or unsubstituted 2-phenylbenzotriazole skeleton bonded to a thioaryl ring group (—S-$\text{A}^{1c}$-S—), $\text{A}^{1c}$ represents a phenyl or naphthyl ring residue or is a group expressed by the following formula,

[Chemical formula 4]

$$\text{——[X}^{1c}\text{—(R}^{1c}\text{)}_n\text{]——(A}^{2c}\text{)}_q\text{—[X}^{2c}\text{—(R}^{2c}\text{)}_p\text{]——}$$

wherein each of $\text{X}^{1c}$ and $\text{X}^{2c}$ independently represents a residue of a phenyl or naphthyl ring, each of n $\text{R}^{1c}$s and p $\text{R}^{2c}$s independently represents a hydrocarbon group having 1 to 18 carbon atoms, an alkoxy group having 1 to 18 carbon atoms or a hydroxy group, each of n and p represents an integer of 0) to 4, $\text{A}^{2c}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, a divalent aromatic group or a sulfide group —S—, q represents an integer of 0 or 1;

[Chemical formula 5]

$$\text{(R}^{1d}\text{)}_r\text{——X}^{1d}\text{—S——PhBzT}^{1d}\text{—A}^{1d}\text{—PhBzT}^{2d}\text{—S——X}^{2d}\text{—(R}^{2d}\text{)}_e$$

wherein each of $\text{PhBzT}^{1d}$ and $\text{PhBzT}^{2d}$ independently represents a substituted or unsubstituted 2-phenylbenzotriazole skeleton that has a thioaryl ring group (—S—$\text{X}^{1d}$— . . . or —S—$\text{X}^{2d}$— . . . ) bonded to a phenyl moiety of a benzotriazole skeleton and $\text{A}^{1d}$ bonded to a position-2 phenyl skeleton Ph, each of $\text{X}^{1d}$ and $\text{X}^{2d}$ independently represents a residue of a phenyl or naphthyl ring, each of r $\text{R}^{1d}$s and s $\text{R}^{2d}$s independently represents a hydrocarbon group having 1 to 18 carbon atoms, an alkoxy group having 1 to 18 carbon atoms or a hydroxy group, each of r and s represents an integer of 0 to 5, $\text{A}^{1d}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom.

As an index for a light resistance of such highly light-resistant ultraviolet absorber, it is preferred that when measured under the following condition(s), a difference in transmittance (ΔTuv) at at least one of wavelengths 380, 390 and 400 nm be not larger than 6%; it is more preferred that when measured under these conditions, the difference in transmittance (ΔTuv) at each of the wavelengths 380, 390 and 400 nm be not larger than 6%; it is even more preferred that when measured under these conditions, the difference in transmittance (ΔTuv) at each of the wavelengths 380, 390 and 400 nm be not larger than 4%; it is particularly preferred that when measured under these conditions, a difference in transmittance (ΔTuv) at each of the wavelengths 380, 390 and 400 nm be not larger than 2%.

<Condition for measuring difference in transmittance (ΔTuv)>

A sample prepared by applying to a soda glass an acrylic resin and the ultraviolet absorber at a mass ratio of 0.6 to 3.4:0.1 and at a film thickness of 2 to 50 μm is irradiated with an ultraviolet for 70 hours under a condition(s) of wavelength 300 to 400 nm, irradiance 42 W/m², black panel temperature 63° C. Based on a transmittance by UV-Vis transmission spectrum before irradiation (T₁uv) and a transmittance by UV-Vis transmission spectrum after irradiation (T₂uv), calculation is performed using the following formula.

$$\text{Difference in transmittance } (\Delta Tuv) = T_1uv - T_2uv \ (\%). \quad \text{[Formula 1]}$$

[II] A heat-resistant ultraviolet absorber of the present invention is characterized by comprising a 2-phenylbenzotriazole derivative that contains a thioaryl ring group and is represented by any one of the following formulae (1), (3) and (4):

[Chemical formula 6]

$$PhBzT^{1a}\text{—S——}X^{1a}\text{—}(R^{1a})_1 \quad (1)$$

wherein $PhBzT^{1a}$ represents a substituted or unsubstituted 2-phenylbenzotriazole skeleton bonded to a thioaryl ring group (—S—$X^{1a}$— . . . ), $X^{1a}$ represents a residue of a phenyl or naphthyl ring, each of 1 $R^{1a}$s independently represents a hydrocarbon group having 1 to 18 carbon atoms, an alkoxy group having 1 to 18 carbon atoms or a hydroxy group, 1 represents an integer of 0 to 5;

[Chemical formula 7]

$$PhBzT^{1c}\text{—S——}A^{1c}\text{—S——}PhBzT^{2c} \quad (3)$$

wherein each of $PhBzT^{1c}$ and $PhBzT^{2c}$ independently represents a substituted or unsubstituted 2-phenylbenzotriazole skeleton bonded to a thioaryl ring group (—S-$A^{1c}$-S—), $A^{1c}$ represents a phenyl or naphthyl ring residue or is a group expressed by the following formula,

[Chemical formula 8]

$$\text{——}[X^{1c}\text{—}(R^{1c})_n]\text{——}(A^{2c})_q\text{—}[X^{2c}\text{—}(R^{2c})_p]\text{——}$$

wherein each of $X^{1c}$ and $X^{2c}$ independently represents a residue of a phenyl or naphthyl ring, each of n $R^{1c}$s and p $R^{2c}$s independently represents a hydrocarbon group having 1 to 18 carbon atoms, an alkoxy group having 1 to 18 carbon atoms or a hydroxy group, each of n and p represents an integer of 0 to 4, $A^{2c}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, a divalent aromatic group or a sulfide group —S—, q represents an integer of 0 or 1;

[Chemical formula 9]

$$(R^{1d})_r\text{——}X^{1d}\text{-S——}PhBzT^{1d}\text{-}A^{1d}\text{-}PhBzT^{2d}\text{—S——}X^{2d}\text{—}(R^{2d}), \quad (4)$$

wherein each of $PhBzT^{1d}$ and $PhBzT^{2d}$ independently represents a substituted or unsubstituted 2-phenylbenzotriazole skeleton that has a thioaryl ring group (—S—$X^{1d}$— . . . or —S—$X^{2d}$— . . . ) bonded to a phenyl moiety of a benzotriazole skeleton and $A^{1d}$ bonded to a position-2 phenyl skeleton Ph, each of $X^{1d}$ and $X^{2d}$ independently represents a residue of a phenyl or naphthyl ring, each of r $R^{1d}$s and s $R^{2d}$s independently represents a hydrocarbon group having 1 to 18 carbon atoms, an alkoxy group having 1 to 18 carbon atoms or a hydroxy group, each of r and s represents an integer of 0 to 5, $A^{1d}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom.

[III] A durable ultraviolet absorber of the present invention is also the aforementioned heat-resistant ultraviolet absorber i.e. a highly light-resistant and heat-resistant durable ultraviolet absorber characterized by exhibiting a difference in transmittance (ΔTuv) of not larger than 6% at at least one of the wavelengths 380, 390 and 400 nm when measured by the following condition(s).

<Condition for Measuring Difference in Transmittance>

A sample prepared by applying to a soda glass an acrylic resin and the ultraviolet absorber at a mass ratio of 0.6 to 3.4:0.1 and at a film thickness of 2 to 50 μm is irradiated with an ultraviolet for 70 hours under a condition(s) of wavelength 300 to 400 nm, irradiance 42 W/m², black panel temperature 63° C. Based on a transmittance by UV-Vis transmission spectrum before irradiation (T₁uv) and a transmittance by UV-Vis transmission spectrum after irradiation (T₂uv), calculation is performed using the following formula.

$$\text{Difference in transmittance } (\Delta Tuv) = T_1uv - T_2uv \ (\%). \quad \text{[Formula 1]}$$

As an index for a light resistance of such durable ultraviolet absorber, it is preferred that the difference in transmittance (ΔTuv) thereof be not larger than 6%, more preferably not larger than 4%, even more preferably not larger than 2%, at each of the wavelengths 380, 390 and 400 nm.

An organic resin composition of the present invention contains the abovementioned highly light-resistant ultraviolet absorber, heat-resistant ultraviolet absorber or durable ultraviolet absorber; and an organic resin.

[IV] The ultraviolet absorber of the present invention is an ultraviolet absorber used in an ultraviolet shielding film for glass or in a composition for forming an ultraviolet shielding film for glass. Such ultraviolet absorber is characterized by comprising a 2-phenylbenzotriazole derivative that contains a thioaryl ring group, thiocyclohexyl ring group, thioalkyl group or thioalkylene group and is represented by any one of the following formulae (1) to (6):

[Chemical formula 10]

$$PhBzT^{1a}-S-X^{1a}-(R^{1a})_l \qquad (1)$$

wherein $PhBzT^{1a}$ represents a substituted or unsubstituted 2-phenylbenzotriazole skeleton bonded to a thioaryl ring group ($-S-X^{1a}- \ldots$ ), $X^{1a}$ represents a residue of a phenyl or naphthyl ring, $X^{1a}$ may have a substituent group(s) other than $l$ $R^{1a}$s, each of the $l$ $R^{1a}$s independently represents a hydrocarbon group having 1 to 18 carbon atoms, an alkoxy group having 1 to 18 carbon atoms or a hydroxy group, the hydrocarbon group and alkoxy group represented by $R^{1a}$ may each have hydrogen atoms of carbon chains therein substituted by, base ends of the carbon chains therein interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, $l$ represents an integer of 0 to 5;

[Chemical formula 11]

$$PhBzT^{1b}-S-Cy-(R^{1b})_m \qquad (2)$$

wherein $PhBzT^{1b}$ represents a substituted or unsubstituted 2-phenylbenzotriazole skeleton bonded to a thiocyclohexyl ring group ($-S-Cy- \ldots$ ), Cy represents a cyclohexyl ring residue, Cy may have a substituent group(s) other than $m$ $R^{1b}$s, each of the $m$ $R^{1b}$s independently represents a hydrocarbon group having 1 to 18 carbon atoms, an alkoxy group having 1 to 18 carbon atoms or a hydroxy group, the hydrocarbon group and alkoxy group represented by $R^{1b}$ may each have hydrogen atoms of carbon chains therein substituted by, base ends of the carbon chains therein interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, $m$ represents an integer of 0 to 5;

[Chemical formula 12]

$$PhBzT^{1c}-S-A^{1c}-S-PhBzT^{2c} \qquad (3)$$

wherein each of $PhBzT^{1c}$ and $PhBzT^{2c}$ independently represents a substituted or unsubstituted 2-phenylbenzotriazole skeleton bonded to a thioaryl ring group or thioalkylene group ($-S-A^{1c}-S-$), $A^{1c}$ represents a group expressed by the following formula, a phenyl ring residue, a naphthyl ring residue or a linear or branched alkylene group that has 1 to 22 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom,

[Chemical formula 13]

$$-[X^{1c}-(R^{1c})_n]-(A^{2c})_q-[X^{2c}-(R^{2c})_p]-$$

wherein each of $X^{1c}$ and $X^{2c}$ independently represents a residue of a phenyl or naphthyl ring, $X^{1c}$ and $X^{2c}$ may have substituent groups other than $n$ $R^{1c}$s and $p$ $R^{2c}$s, each of the $n$ $R^{1c}$s and $p$ $R^{2c}$s independently represents a hydrocarbon group having 1 to 18 carbon atoms, an alkoxy group having 1 to 18 carbon atoms or a hydroxy group, the hydrocarbon groups and alkoxy groups represented by $R^{1c}$ and $R^{2c}$ may each have hydrogen atoms of carbon chains therein substituted by, base ends of the carbon chains therein interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, each of $n$ and $p$ represents an integer of 0 to 4, $A^{2c}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, a divalent aromatic group or a sulfide group $-S-$, $q$ represents an integer of 0 or 1;

[Chemical formula 14]

$$(R^{1d})_r-X^{1d}-S-PhBzT^{1d}-A^{1d}-PhBzT^{2d}-S-X^{2d}-(R^{2d}), \qquad (4)$$

wherein each of $PhBzT^{1d}$ and $PhBzT^{2d}$ independently represents a substituted or unsubstituted 2-phenylbenzotriazole skeleton that has a thioaryl ring group ($-S-X^{1d}- \ldots$ or $-S-X^{2d}- \ldots$ ) bonded to a phenyl moiety of a benzotriazole skeleton and $A^{1d}$ bonded to a position-2 phenyl skeleton Ph, each of $X^{1d}$ and $X^{2d}$ independently represents a residue of a phenyl or naphthyl ring, $X^{1d}$ and $X^{2d}$ may have substituent groups other than $r$ $R^{1d}$s and $s$ $R^{2d}$s, each of the $r$ $R^{1d}$s and $s$ $R^{2d}$s independently represents a hydrocarbon group having 1 to 18 carbon atoms, an alkoxy group having 1 to 18 carbon atoms or a hydroxy group, the hydrocarbon groups and alkoxy groups represented by $R^{1d}$ and $R^{2d}$ may each have hydrogen atoms of carbon chains therein substituted by, base ends of the carbon chains therein interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, each of r and s represents an integer of 0 to 5, $A^{1d}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom;

[Chemical formula 15]

$$PhBzT^{1e}\text{---}S\text{---}Y^{1e} \qquad (5)$$

wherein $PhBzT^{1e}$ represents a substituted or unsubstituted 2-phenylbenzotriazole skeleton bonded to a thioalkyl group ($\text{---}S\text{---}Y^{1e}$). $Y^{1e}$ represents a linear or branched alkyl group that has 1 to 22 carbon atoms and may have hydrogen atoms therein substituted by, base ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom;

[Chemical formula 16]

$$Y^{1f}\text{---}S\text{---}PhBzT^{1f}\text{---}A^{1f}\text{---}PhBzT^{2f}\text{---}S\text{---}Y^{2f} \qquad (6)$$

wherein each of $PhBzT^{1f}$ and $PhBzT^{2f}$ independently represents a substituted or unsubstituted 2-phenylbenzotriazole skeleton that has a thioalkyl group ($\text{---}S\text{---}Y^{1f}$ or $\text{---}S\text{---}Y^{2f}$) bonded to a phenyl moiety of a benzotriazole skeleton and $A^{1f}$ bonded to a position-2 phenyl skeleton Ph, each of $Y^{1f}$ and $Y^{2f}$ independently represents a linear or branched alkyl group that has 1 to 22 carbon atoms and may have hydrogen atoms therein substituted by, base ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, $A^{1f}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom.

Effects of the Invention

In the case of the ultraviolet absorber of the present invention, the ultraviolet absorber is capable of minimizing the impact of harmful lights by efficiently absorbing harmful lights in the wavelength region of 380 to 400 nm and suppressing the absorption of lights having a wavelength of not shorter than 400 nm which constitutes the cause of early-stage yellowing; and has a favorable affinity with organic materials and inorganic materials such as glass so that a member having a superior appearance can be produced therewith. Further, as a result of introducing an aryl group into a 2-phenylbenzotriazole skeleton via a thioether group, a stabilization effect of the intermolecular interaction of a x-conjugated system or a hydrocarbon group introduced into such aryl group imparts a superior light resistance or heat resistance, or a superior light resistance and heat resistance, that is, a superior durability to the ultraviolet absorber of the present invention. The ultraviolet absorber-containing organic material composition is such that the ultraviolet absorber therein will not bleed out, the composition has an excellent affinity with the ultraviolet absorber so that the appearance of the composition can be maintained in a superior manner, and especially when the appearance thereof is transparent, such transparency can be maintained in a superior manner by suppressing yellowing. Further, due to the aforementioned properties of the ultraviolet absorber and prevention of organic material deterioration, a superior light resistance and heat resistance, that is, a superior durability can be achieved in a way such that, for example, a discoloration, deterioration in ultraviolet absorption capability and deterioration in transparency will not occur over a long period of use. In addition, the ultraviolet absorber of the present invention can be used to produce an organic material composition of such kind.

MODE FOR CARRYING OUT THE INVENTION

Figure 1:
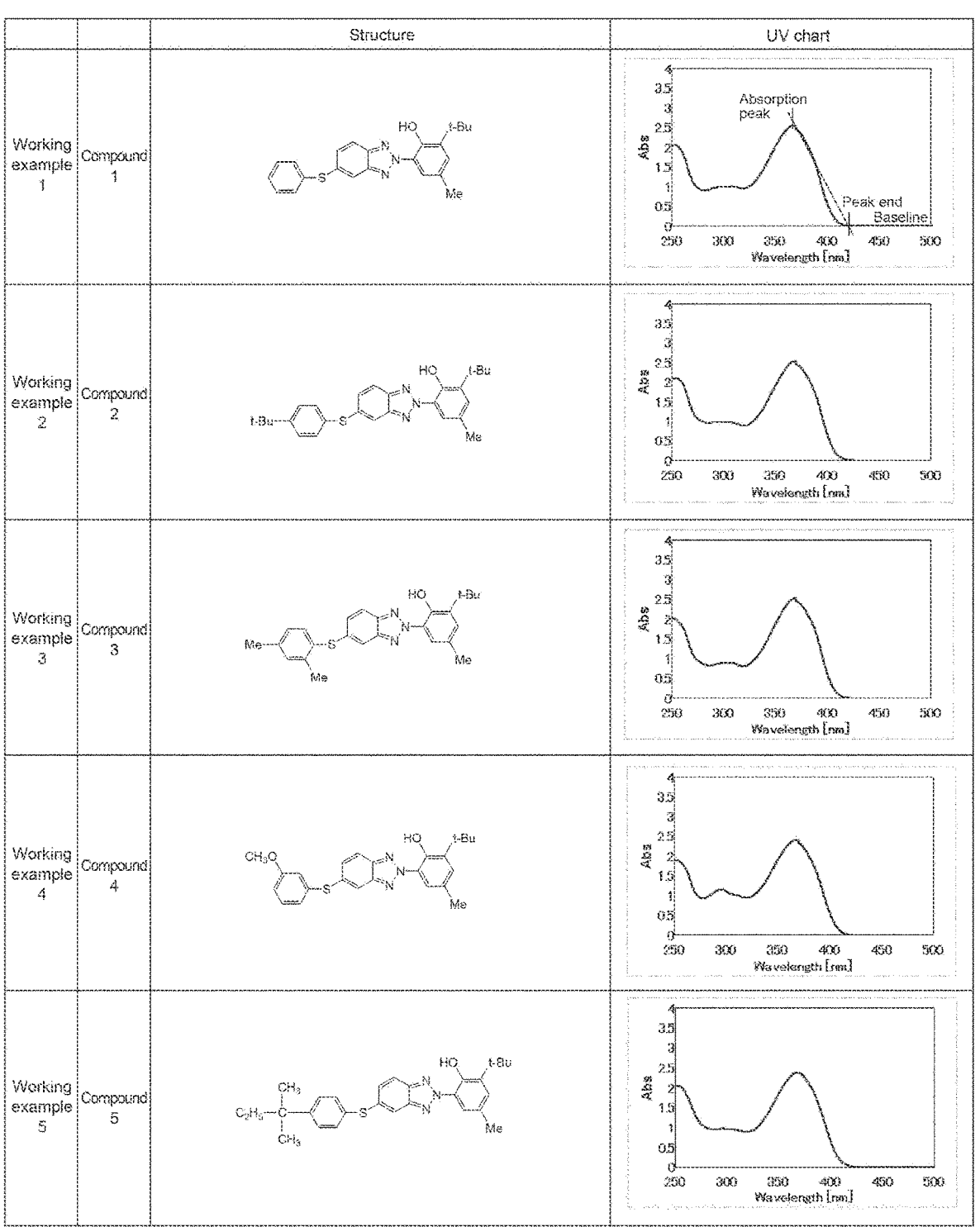
FIG. 1 is a set of ultraviolet-visible absorption spectra (UV charts) of compounds 1 to produced in working examples.
Figure 2:
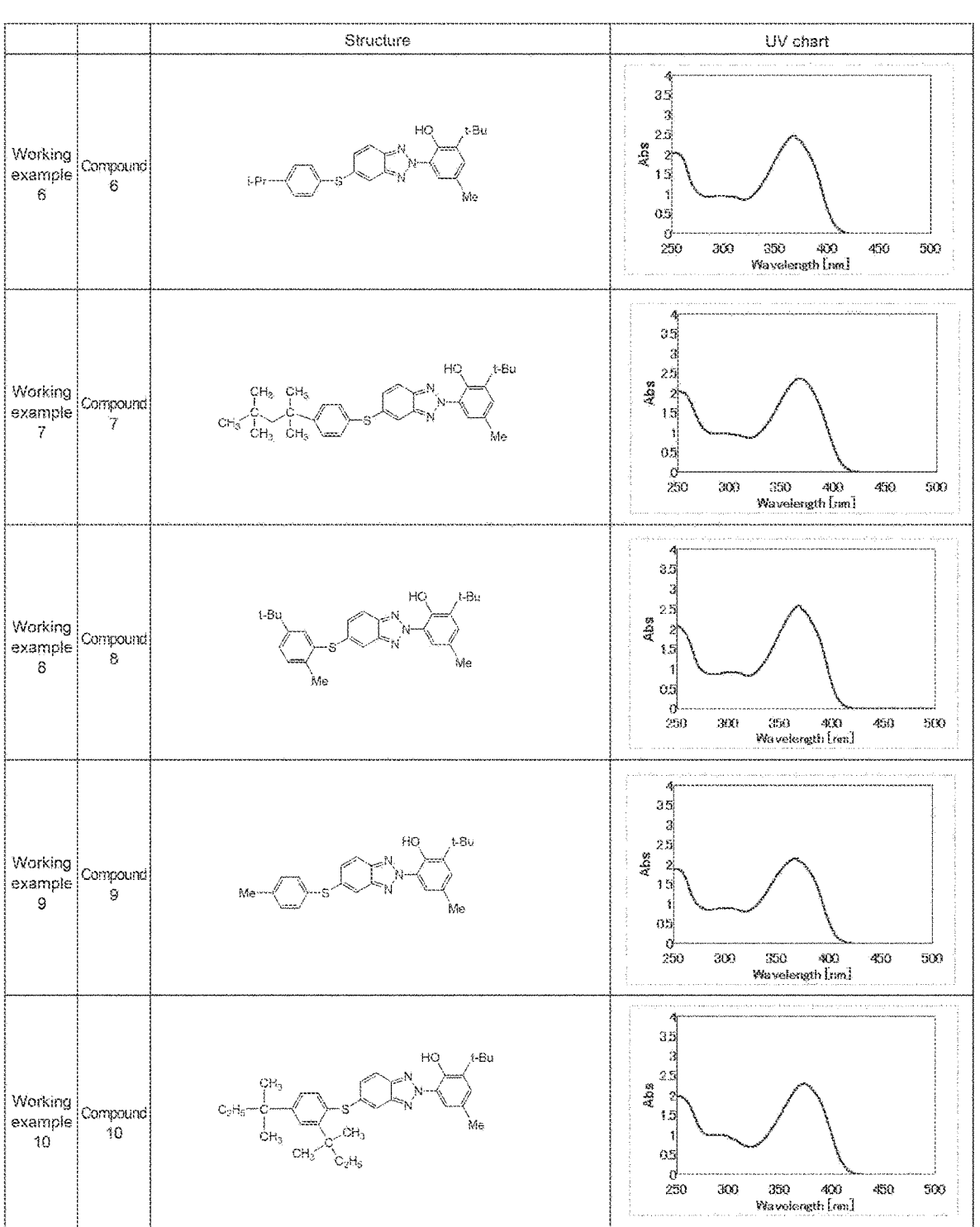
FIG. 2 is a set of ultraviolet-visible absorption spectra (UV charts) of compounds 6 to produced in working examples.
Figure 3:
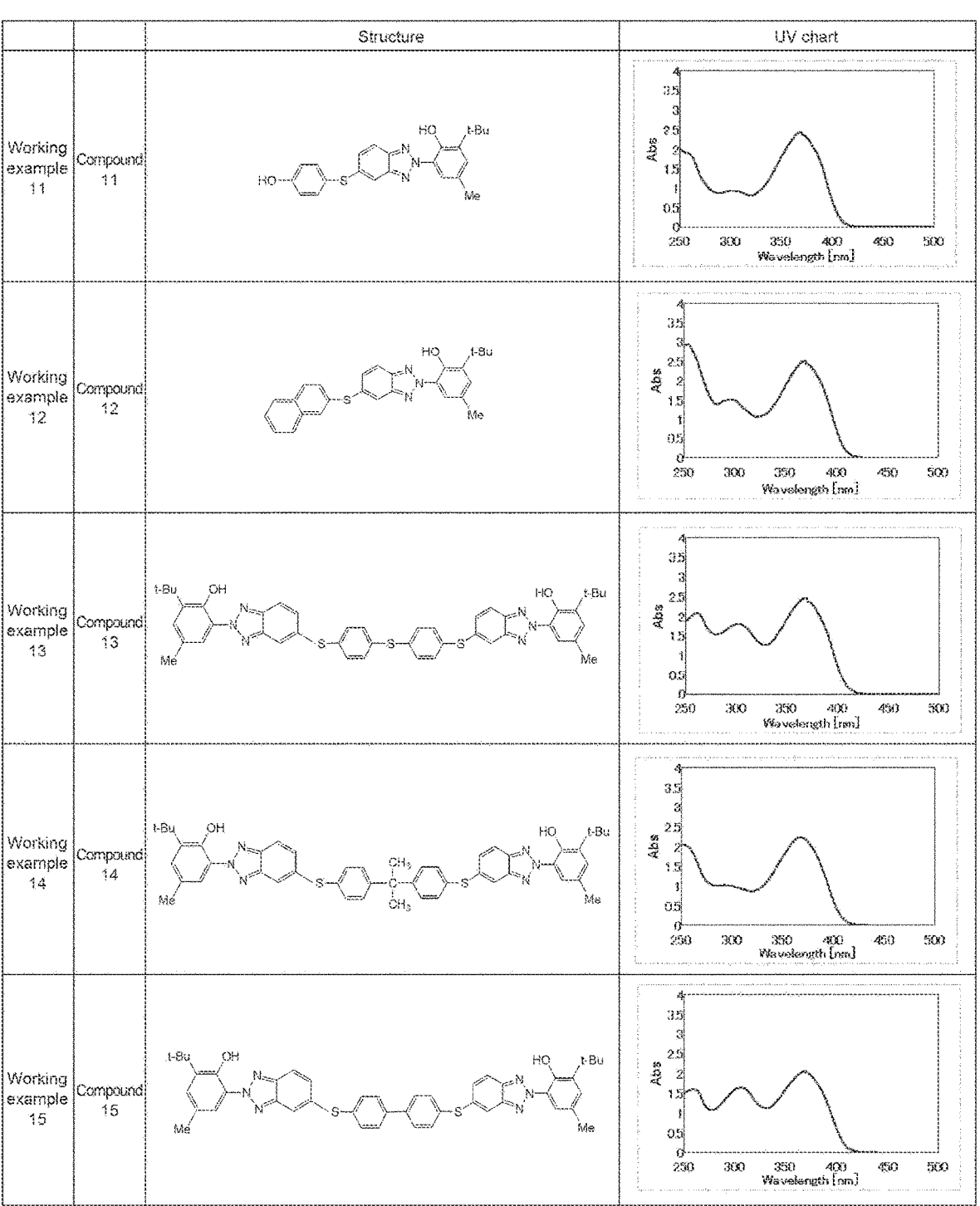
FIG. 3 is a set of ultraviolet-visible absorption spectra (UV charts) of compounds 11 to produced in working examples.
Figure 4:
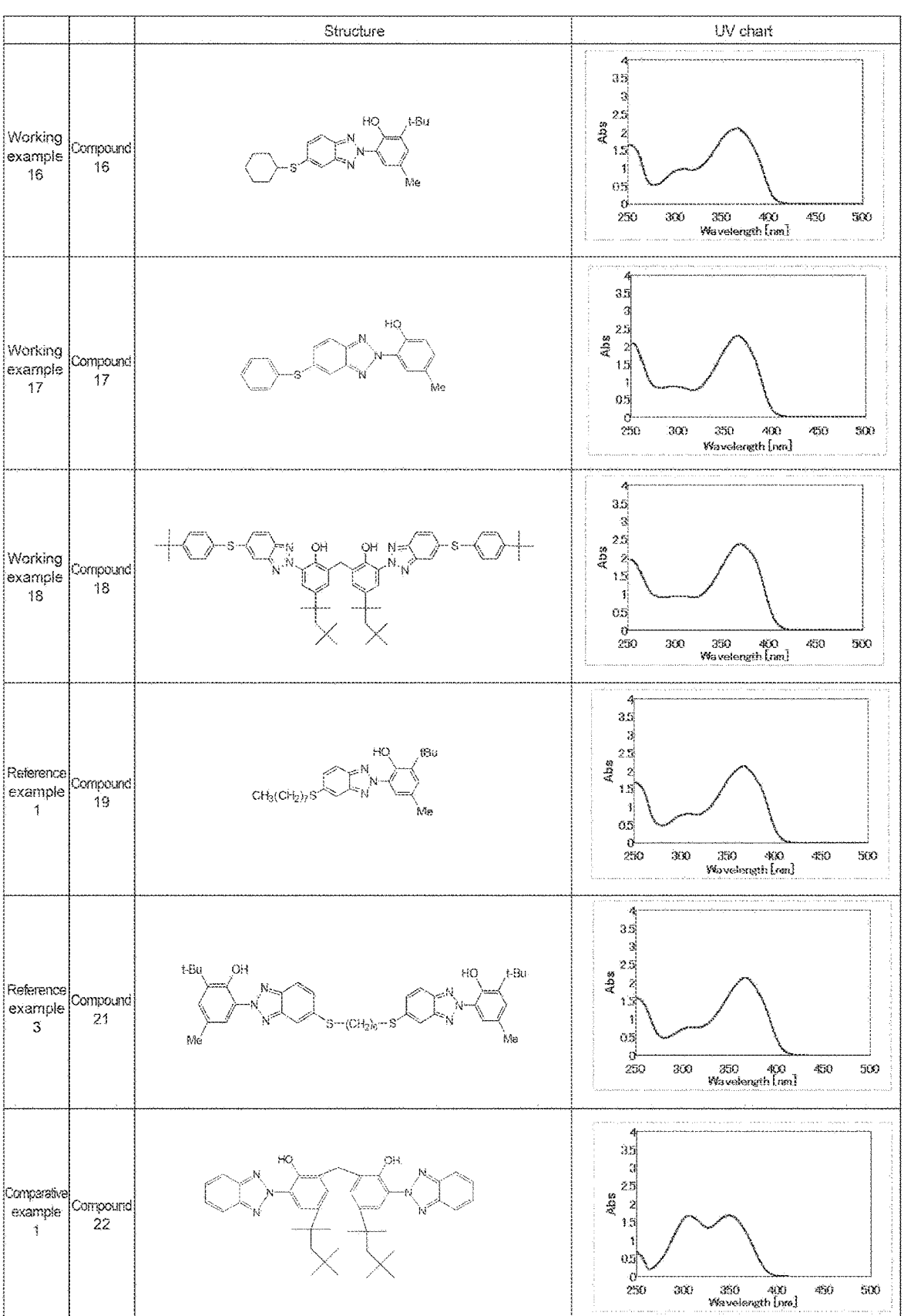
FIG. 4 is a set of ultraviolet-visible absorption spectra (UV charts) of compounds 16 to 18 produced in working examples, compounds 19 and 21 produced in reference examples, and a compound 22 produced in a comparative example.

The present invention is described in detail hereunder.

In this specification, when referred to as "ultraviolet absorber of the present invention," it means at least one of [I] a highly light-resistant ultraviolet absorber. [II] a heat-resistant ultraviolet absorber. [III] a durable ultraviolet absorber, and [IV] an ultraviolet absorber used in an ultraviolet shielding film for glass or in a composition for forming an ultraviolet shielding film for glass.

Although not limited, the term "highly light-resistant ultraviolet absorber" in this specification is mainly intended as that showing differences in transmittance (ΔTuv) at wavelengths of 380, 390 and 400 nm that belong to ranges disclosed in this specification as preferable examples.

Although not limited, the term "heat-resistant ultraviolet absorber" in this specification refers to that exhibiting a rate of change in weight after heating and/or a change in color that belong to the ranges disclosed in this specification as preferable examples.

Although not limited, the term "durable ultraviolet absorber" in this specification mainly refers to that in addition to having the heat resistance as mentioned above, showing differences in transmittance ($\Delta$Tuv) at wavelengths of 380, 390 and 400 nm that belong to ranges disclosed in this specification as preferable examples.

The descriptions hereunder regarding a 2-phenylbenzotriazole skeleton represented by a formula (A) and specific embodiments as well as preferable examples of subsequent 2-phenylbenzotriazole derivatives represented by formulae (1) to (4), are directed to all the ultraviolet absorbers of the present invention unless otherwise noted; while the descriptions are mainly focused on a highly light-resistant ultraviolet absorber, they also include specific embodiments as well as preferable examples of a heat-resistant ultraviolet absorber, a durable ultraviolet absorber, an ultraviolet absorber used in an organic resin composition, an ultraviolet shielding film for glass or a composition for forming an ultraviolet shielding film for glass, based on results in a later-described section of working examples.

The ultraviolet absorbers of the present invention, particularly a highly light-resistant ultraviolet absorber, a heat-resistant ultraviolet absorber and a durable ultraviolet absorber are each comprised of a 2-phenylbenzotriazole derivative that contains a thioaryl ring group or thiocyclohexyl ring group. This 2-phenylbenzotriazole derivative is represented by any one of the above formulae (1) to (4). Further, the ultraviolet absorber used in an ultraviolet shielding film for glass or in a composition for forming an ultraviolet shielding film for glass is comprised of a 2-phenylbenzotriazole derivative that contains a thioaryl ring group, thiocyclohexyl ring group, thioalkyl group or thioalkylene group. This 2-phenylbenzotriazole derivative is represented by any one of the above formulae (1) to (6).

(2-phenylbenzotriazole Skeleton of 2-phenylbenzotriazole Derivative)

2-phenylbenzotriazole skeletons as represented by PhBzT$^{1a}$ in the formula (1), PhBzT$^{1b}$ in the formula (2), PhBzT$^{1c}$ and PhBzT$^{2c}$ in the formula (3), PhBzT$^{1d}$ and PhBzT$^{2d}$ in the formula (4), PhBzT$^{1e}$ in the formula(S), and PhBzT$^{1f}$ and PhBzT$^{2f}$ in the formula (6), are each represented by the following formula (A).

[Chemical formula 17]

(A)

In the formula (A), at least one of R$^1$ to R$^9$ independently represents a thioaryl ring group, a thiocyclohexyl ring group, a thioalkyl group or a thioalkylene group, whereas the rest of them each represent a hydrogen atom or a substituent group.

In the formula (A), there are no particular limitations on the substitution position of the thioaryl ring group, thiocyclohexyl ring group, thioalkyl group or thioalkylene group;

unless otherwise specified in the above formulae (1) to (6), the substitution position(s) may be any one of R$^1$ to R$^9$, and it is preferred that the substitution position(s) be R$^6$ to R$^9$, more preferably R$^7$ and R$^8$. While there are also no particular limitations on the substitution number of the thioaryl ring group, thiocyclohexyl ring group, thioalkyl group or thioalkylene group unless otherwise specified in the above formulae (1) to (6), the substitution number may be 1 to 2, preferably 1.

Examples of the abovementioned substituent group include the following monovalent or divalent groups selected from a hydrocarbon group, an aromatic group, an unsaturated group, a nitrogen-containing group, an oxygen-containing group, a phosphorus-containing group, an alicyclic group and a halogen atom. When the substituent group is a divalent group, any two (preferably any adjacent two) of R$^1$ to R$^9$ together form a ring. These substituent groups may also have the hydrogen atoms therein substituted by, at least one of the two ends thereof interrupted by, or the carbon-carbon bonds therein interrupted by a monovalent or divalent group(s) selected from an aromatic group, an unsaturated group, a nitrogen-containing group, an oxygen-containing group, a phosphorus-containing group, an alicyclic group and a halogen atom, as exemplified hereunder.

Examples of the hydrocarbon group include linear or branched alkyl groups, linear or branched alkenyl groups, linear or branched alkynyl groups; and benzene rings, naphthalene rings and anthracene rings of which hydrogen atoms may be substituted by alkyl groups. It is preferred that such hydrocarbon group has 1 to 18, more preferably 1 to 10 carbon atoms. Although not particularly limited, specific examples of the linear or branched alkyl groups include a methyl group, benzyl group, $\alpha,\alpha$-dimethylbenzyl group, ethane-1-yl group, propane-1-yl group, 1-methylethane-1-yl group, butane-1-yl group, butane-2-yl group, 2-methylpropane-1-yl group, 2-methylpropane-2-yl group, pentane-1-yl group, pentane-2-yl group, hexane-1-yl group, heptane-1-yl group, octane-1-yl group, 1,1,3,3-tetramethylbutane-1-yl group, nonane-1-yl group, decane-1-yl group, undecane-1-yl group, dodecane-1-yl group, tridecane-1-yl group, tetradecane-1-yl group, pentadecane-1-yl group, hexadecane-1-yl group, heptadecane-1-yl group and octadecane-1-yl group, Examples of the linear or branched alkenyl groups include a vinyl group, prop-1-en-1-yl group, allyl group, an isopropenyl group, but-1-en-1-yl group, but-2-en-1-yl group, a but-3-en-1-yl group, 2-methylprop-2-en-1-yl group, 1-methylprop-2-en-1-yl group, pent-1-en-1-yl group, pent-2-en-1-yl group, pent-3-en-1-yl group, pent-4-en-1-yl group, 3-methylbut-2-en-1-yl group, 3-methylbut-3-en-1-yl group, hex-1-en-1-yl group, hex-2-en-1-yl group, hex-3-en-1-yl group, hex-4-en-1-yl group, hex-5-en-1-yl group, 4-methylpent-3-en-1-yl group, 4-methylpent-3-en-1-yl group, hept-1-en-1-yl group, hept-6-en-1-yl group, oct-1-en-1-yl group, oct-7-en-1-yl group, non-1-en-1-yl group, non-8-en-1-yl group, dec-1-en-1-yl group, dec-9-en-1-yl group, undec-1-en-1-yl group, undec-10-en-1-yl group, dodec-1-en-1-yl group, dodec-11-en-1-yl group, tridec-1-en-1-yl group, tridec-12-en-1-yl group, tetradec-1-en-1-yl group, tetradec-13-en-1-yl group, pentadec-1-en-1-yl group, pentadec-14-en-1-yl group, hexadec-1-en-1-yl group, hexadec-15-en-1-yl group, heptadec-1-en-1-yl group, heptadec-16-en-1-yl group, octadec-1-en-1-yl group, octadec-9-en-1-yl group and octadec-17-en-1-yl group, Examples of the linear or branched alkynyl groups include ethynyl, prop-1-yne-1-yl group, prop-2-yne-1-yl group, but-1-yne-1-yl group, but-3-yne-1-yl group, 1-methylprop-2-yne-1-yl group, pent-1- yne-1-yl group, pent-4-yne-1-yl group, hex-1-yne-1-yl group, hex-5-yne-1-yl group, hept-1-yne-1-yl group, hept-6-yne-1-yl group, oct-1-yne-1-yl group, oct-7-yne-1-yl group, non-1-yne-1-yl group, non-8-yne-1-yl group, dec-1-yne-1-yl group, dec-9-yne-1-yl group, undec-1-yne-1-yl group, undec-10-yne-1-yl group, dodec-1-yne-1-yl group, dodec-11-yne-1-yl group, tridec-1-yne-1-yl group, tridec-12-yne-1-yl group, tetradec-1-yne-1-yl group, tetradec-13-yne-1-yl group, pentadec-1-yne-1-yl group, pentadec-14-yne-1-yl group, hexadec-1-yne-1-yl group, hexadec-15-yne-1-yl group, heptadec-1-yne-1-yl group, heptadec-16-yne-1-yl group, octadec-1-yne-1-yl group and octadec-17-yne-1-yl group. Among these examples, preferred are linear or branched alkyl groups each having 1 to 18 carbon atoms; more preferred are linear or branched alkyl groups each having 1 to 10 carbon atoms. Further, the hydrogen atoms in those hydrocarbon groups may be substituted by halogen atoms such as fluorine, chlorine, bromine and iodine atoms.

The aromatic group has an aromatic ring such as a benzene ring, a naphthalene ring and an anthracene ring; and preferably has 6 to 18, more preferably 6 to 14 carbon atoms. Although not particularly limited, examples of a monovalent aromatic group include a phenyl group, 2-methylphenyl group, 3-methylphenyl group, 4-methylphenyl group, 2,4-dimethylphenyl group, 2,5-dimethylphenyl group, 3,4-dimethylphenyl group, 3,5-dimethylphenyl group, 2,4,5-trimethylphenyl group, 2,4,6-trimethylphenyl group, 4-biphenyl group, 2-methoxyphenyl group, 3-methoxyphenyl group, 4-methoxyphenyl group, 2-ethoxyphenyl group, 3-ethoxyphenyl group, 4-ethoxyphenyl group, 2-chlorophenyl group, 2-fluorophenyl group, 4-fluorophenyl group, 2-trifluoromethylphenyl group, 4-trifluoromethylphenyl group, 1-naphthyl group, 2-naphthyl group, 1-anthracenyl group, 2-anthracenyl group and 9-anthracenyl group. Although not particularly limited, examples of a divalent aromatic group include 1,4-phenylene group, 1,3-phenylene group, 1,2-phenylene group, 1,8-naphthylene group, 2,7-naphthylene group, 2,6-naphthylene group, 1,4-naphthylene group, 1,3-naphthylene group, 9,10-anthracenylene group, 1,8-anthracenylene group, 2,7-anthracenylene group, 2,6-anthracenylene group, 1,4-anthracenylene group and 1,3-anthracenylene group.

The unsaturated group has an unsaturated bond(s) of carbon-carbon or carbon-hetero atom bonds such as a carbon-carbon double bond, a carbon-carbon triple bond, a carbon-oxygen double bond (e.g. carbonyl group, aldehyde group, ester group, carboxy group, carbamate group, urea group, amido group, imide group, carbamoyl group and urethane group), a carbon-nitrogen double bond (e.g. isocyanate group) and a carbon-nitrogen triple bond (e.g. cyano group and cyanato group); and preferably has 1 to 10, more preferably 1 to 8 carbon atoms. Although not particularly limited, examples of the unsaturated group include an acryloyl group, methacryloyl group, maleic acid monoester group, styryl group, allyl group, vinyl group, alkenyl group, alkynyl group, carbonyl group, aldehyde group, ester group, carboxy group, carbamate group, urea group, amide group, imide group, carbamoyl group, cyano group, cyanato group, isocyanate group and urethane group.

The nitrogen-containing group has a cyano group, a nitro group or a primary to tertiary amino group; and preferably has 0 to 10 carbon atoms. Although not particularly limited, examples of the nitrogen-containing group include a cyano group, cyanato group, isocyanate group, nitro group, nitroalkyl group, carbamate group, urea group, amide group, imide group, carbamoyl group and urethane group; as well as an imide group, amino group, primary amino group, secondary amino group, tertiary amino group, aminoalkyl group, 3,4,5,6-tetrahydrophthalimidylmethyl group and 2-[6-(2H-benzotriazole-2-yl-)-4-(1,1,3,3-tetramethylbutyl) phenol-yl]-methyl group.

If containing an aromatic ring group or an alicyclic group, the oxygen-containing group preferably has 6 to 18, more preferably 6 to 14, even more preferably 6 to 12 carbon atoms; if containing no aromatic ring group or alicyclic group, the oxygen-containing group preferably has 0 to 18 carbon atoms. Although not particularly limited, examples of the oxygen-containing group include a hydroxy group, alkoxy group, methoxy group, ethoxy group, n-propoxy group, isopropoxy group, n-butoxy group, sec-butoxy group, iso-butoxy group, t-butoxy group, sec-pentyloxy group, iso-pentyloxy group, t-pentyloxy group, 1-hexyloxy group, 2-hexyloxy group, 3-hexyloxy group, 1-heptyloxy group, 2-heptyloxy group, 3-heptyloxy group, 4-heptyloxy group, 1-octyloxy group, 2-octyloxy group, 3-octyloxy group, 4-octyloxy group, 1-nonyloxy group, 2-nonyloxy group, 3-nonyloxy group, 4-nonyloxy group, 5-nonyloxy group, 1-decyloxy group, 2-decyloxy group, 3-decyloxy group, 4-decyloxy group, S-decyloxy group, 1-undecyloxy group, 1-dodecyloxy group, 1-tridecyloxy group, 1-tetradecyloxy group, I-pentadecyloxy group, 1-hexadecyloxy group, 1-heptadecyloxy group, 1-octadecyloxy group, phenoxy group, methylphenoxy group, dimethylphenoxy group, naphthoxy group, phenylmethoxy group, phenylethoxy group, acetoxy group, acetyl group, aldehyde group, carboxy group, urea group, urethane group, amide group, imide group, ether group, carbonyl group, ester group, oxazole group, morpholin group, carbamate group, carbamoyl group and polyoxyethylene group. Among these examples, preferred are a hydroxy group, an alkoxy group having 1 to 18 carbon atoms, an ether group having 1 to 18 carbon atoms, an ester group having 1 to 18 carbon atoms, and a polyoxyethylene group having 1 to 20 carbon atoms.

The phosphorus-containing group has a phosphine group, phosphite group, phosphonic acid group, phosphinic acid group, phosphoric acid group or phosphoester group; and preferably has 6 to 22 carbon atoms if containing an aromatic ring group or an alicyclic group, 0 to 18 carbon atoms if containing no aromatic ring group or alicyclic group. Although not particularly limited, examples of the phosphorus-containing group include a trimethylphosphine group, triethylphosphine group, tripropylphosphine group, tributylphosphine group, tripentylphosphine group, trihexylphosphine group, tricyclohexylphosphine group, triphenylphosphine group, tritrylphosphine group, methylphosphite group, ethylphosphite group, phenylphosphite group, phosphonic acid group, phosphinic acid group, phosphoric acid group and phosphoester group, The alicyclic group preferably has 3 to 10, more preferably 3 to 8 carbon atoms. Although not particularly limited, examples of such alicyclic group include a cyclopropyl group, cyclobutyl group, cyclopentyl group, cyclohexyl group, cycloheptyl group and cyclooctyl group.

Examples of the halogen atom include a fluorine atom, chlorine atom, bromine atom and iodine atom.

From the perspective of improving light resistance, the following combinations of substituent groups are preferred.

As for the following a to o, in terms of a combination of the ultraviolet absorber of the present invention and an organic material including an organic resin(s), preferable examples of combinations of $R^6$, $R^7$, $R^8$ and $R^9$ in the formula (A) are as follows.

a-1: at least one of $R^6$, $R^7$, $R^8$ and $R^9$ in each formula (1), (3) and (4) is a thioaryl ring group; at least one of $R^6$, $R^7$, $R^8$ and $R^9$ in the formula (2) is a thiocyclohexyl ring group; in [IV], at least one of $R^6$, $R^7$, $R^8$ and $R^9$ in the formula (3) is a thioalkylene group; at least one of $R^6$, $R^7$, $R^8$ and $R^9$ in the formulae (5), (6) is a thioalkyl group.

a-2: in a-1, $X^{1a}$, $X^{1c}$, $X^{2c}$, $X^{1d}$ and $X^{2d}$ in the thioaryl ring groups are residues of phenyl rings or naphthyl rings.

a-3: in a-1, a-2, one thioaryl ring group or thiocyclohexyl ring group is bonded to $PhBzT^{1a}$, $PhBzT^{1b}$, $PhBzT^{1c}$, $PhBzT^{2c}$, $PhBzT^{1d}$, $PhBzT^{2d}$; in [IV], one thioalkylene group is bonded to $PhBzT^{1c}$, $PhBzT^{2c}$; one thioalkyl group is bonded to $PhBzT^{1e}$, $PhBzT^{1f}$, $PhBzT^{2f}$.

a-4: in any one of a-1 to a-3, one thioaryl ring group or thiocyclohexyl ring group is bonded to $R^7$ or $R^8$; in [IV], one thioalkylene group, one thioalkyl group are bonded to $R^7$ or $R^8$.

a-5: in any one of a-1 to a-4, $R^6$ to $R^9$ other than those representing thioaryl ring groups or thiocyclohexyl ring groups are all hydrogen atoms; in [IV], $R^6$ to $R^9$ other than those representing thioalkylene groups or thioalkyl groups are all hydrogen atoms.

a-6: in any one of a-1 to a-5, $X^{1a}$, $X^{1c}$, $X^{2c}$, $X^{1d}$ and $X^{2d}$ in the thioaryl ring groups are residues of phenyl rings.

a-7: in any one of a-1 to a-5, $X^{1a}$, $X^{1c}$, $X^{2c}$, $X^{1d}$ and $X^{2d}$ in the thioaryl ring groups are residues of naphthyl rings.

As for the formulae (1) to (3) and (5), preferable examples of combinations of $R^1$, $R^2$, $R^3$, $R^4$ and $R^5$ in the formula (A) are as follows, $R^1$, $R^2$, $R^3$, $R^4$ and $R^5$ in $PhBzT^{1c}$ and $PhBzT^{2c}$ in the formula (3) may be independently different from or identical to one another.

i-1: Containing at least one substituent group selected from a hydrocarbon group having 1 to 18 carbon atoms (including hydrocarbon groups having 2 to 18 carbon atoms, such as an alkenyl group and an alkynyl group); a hydroxy group; an aromatic group having 6 to 18 carbon atoms; an ether group having 1 to 18 carbon atoms; an alkoxy group having 1 to 18 carbon atoms; an ester group having 1 to 18 carbon atoms; a (meth)acryloyloxy group and/or a polyoxyethylene group having 1 to 20 carbon atoms; or a hydrocarbon group that has 1 to 18 carbon atoms that may have the hydrogen atoms therein substituted by, the base end(s) thereof interrupted by, or the carbon-carbon bonds therein interrupted by these substituent groups.

i-2: in i-1, the substituent group is at least one kind selected from a hydrocarbon group having 1 to 10 carbon atoms and a hydroxy group.

i-3: in i-2, the substituent group is at least one kind selected from a hydrocarbon group having 1 to 8 carbon atoms and a hydroxy group.

i-4: in any one of i-1 to i-3, a hydrocarbon group as the substituent group is a linear or branched alkyl group.

i-5: in i-4, the substituent group is at least one kind selected from a methyl group, a t-butyl group and a hydroxy group.

i-6: in i-5, the substituent group is at least one kind selected from a methyl group, a t-butyl group and a hydroxy group, where the number of the hydroxy groups is not larger than 1.

i-7: in any one of i-1 to i-6, the number of the substituent groups is 1 to 4.

i-8: in any one of i-1 to i-7, the substituent group is present at any position of $R^1$ to $R^4$, whereas the rest of $R^1$ to $R^5$ are hydrogen atoms.

i-9: in any one of i-1 to i-8, the substituent group is present at any position of $R^1$, $R^2$ and $R^4$, whereas the rest of $R^1$ to $R^5$ are hydrogen atoms.

i-10: in i-9, $R^1$ is a hydroxy group; $R^1$ is a t-butyl group; $R^4$ is a methyl group; $R^3$ and $R^5$ are hydrogen atoms.

i-11: in any one of i-1 to i-9, the substituent group is present at any position of $R^1$ and $R^4$, whereas the rest of $R^1$ to $R^5$ are hydrogen atoms.

i-12: in i-11, $R^1$ is a hydroxy group; $R^4$ is a methyl group; $R^2$, $R^3$ and $R^5$ are hydrogen atoms.

As for the formulae (4) and (6), preferable examples of combinations of $R^1$, $R^2$, $R^3$, $R^4$ and $R^5$ in the formula (A) are as follows, $R^1$, $R^2$, $R^3$, $R^4$ and $R^5$ in $PhBzT^{1d}$ and $PhBzT^{2d}$ in the formula (4) as well as $PhBzT^{1f}$ and $PhBzT^{2f}$ in the formula (6) may be independently different from or identical to one another.

i-13: $R^2$ in each of $PhBzT^{1d}$ and $PhBzT^{2d}$ is-$A^{1d}$-; $R^2$ in each of $PhBzT^{1f}$ and $PhBzT^{2f}$ is -$A^{1f}$-.

i-14: in i-13, -$A^{1d}$- and -$A^{1f}$- each represent a divalent hydrocarbon group having 1 to 8 carbon atoms.

i-15: in i-13, -$A^{1d}$- and -$A^{1f}$- each represent a divalent hydrocarbon group having 1 to 4 carbon atoms.

i-16: in i-13, -$A^{1d}$- and -$A^{1f}$- each represent a divalent hydrocarbon group having 1 to 2 carbon atoms.

i-17: in any one of i-14 to i-16, -$A^{1d}$- and -$A^{1f}$- each represent a linear or branched alkyl group.

i-18: in i-17, -$A^{1d}$- and -$A^{1f}$- each represent a methylene group or an ethylene group.

i-19: in any one of i-13 to i-18, those of $R^1$, $R^2$, $R^3$, $R^4$ and $R^5$ that do not represent -$A^{1d}$- and -$A^{1f}$- have at least one substituent group selected from a hydrocarbon group having 1 to 18 carbon atoms (including hydrocarbon groups having 2 to 18 carbon atoms, such as an alkenyl group and an alkynyl group); a hydroxy group, an aromatic group having 6 to 18 carbon atoms; an ether group having 1 to 18 carbon atoms; an alkoxy group having 1 to 18 carbon atoms; an ester group having 1 to 18 carbon atoms; a (meth)acryloyloxy group; a polyoxyethylene group; or a hydrocarbon group that has 1 to 18 carbon atoms, and may have the hydrogen atoms therein substituted by, the terminal end(s) thereof interrupted by, or the carbon-carbon bonds therein interrupted by these substituent groups.

i-20: in i-19, the substituent group is at least one kind selected from a hydrocarbon group having 1 to 10 carbon atoms and a hydroxy group.

i-21: in i-20, the substituent group is at least one kind selected from a hydrocarbon group having 1 to 8 carbon atoms and a hydroxy group.

i-22: in any one of i-19 to i-21, a hydrocarbon group as the substituent group is a linear or branched alkyl group.

i-23: in i-22, the substituent group is at least one kind selected from a methyl group, t-butyl group, 1,1,3,3-tetramethylbutyl group and hydroxy group.

i-24: in i-23, the substituent group is at least one kind selected from a methyl group, t-butyl group, 1,1,3,3-tetramethylbutyl group and hydroxy group, where the number of the hydroxy groups is not larger than 1.

i-25: in any one of i-19 to i-24, the number of the substituent groups is 1 to 4.

i-26: in any one of i-19 to i-25, the substituent group is present at any position of $R^1$, $R^3$ and $R^4$, whereas the rest of $R^1$, $R^3$, $R^4$ and $R^5$ are hydrogen atoms.

i-27: in any one of i-19 to i-26, the substituent group is present at any position of $R^1$ and $R^4$, whereas $R^3$ and $R^5$ are hydrogen atoms.

i-28: in i-27, $R^1$ is a hydroxy group; $R^4$ is 1,1,3,3-tetramethylbutyl group; $R^3$ and $R^5$ are hydrogen atoms.

(2-phenylbenzotriazole derivatives that contain a thioaryl ring group ($-S-X^{1a}-$ . . . , $-S-X^{1d}-$ . . . or $-S-X^{2d}-$ . . . ) and are represented by the formulae (1) and (4))

Preferable examples of combinations of l $R^{1a}$s and $X^{1a}$, r $R^{1d}$s and $X^{1d}$ as well as s $R^{2d}$s and $X^{2d}$ in each formula (1), (4) are as follows.

u-1: $X^{1a}$, $X^{1d}$ and $X^{2d}$ are residues of phenyl rings.

u-2: in u-1, l, r, s=0; substituent groups $R^{1a}$, $R^{1d}$ and $R^{2d}$ are not present at $X^{1a}$, $X^{1d}$ and $X^{2d}$, moieties of $X^{1a}$, $X^{1d}$ and $X^{2d}$ that are substitutable by $R^{1a}$, $R^{1d}$ and $R^{2d}$ are all hydrogen atoms.

u-3: in u-1, each of the l $R^{1d}$s, r $R^{1d}$s and s $R^{2d}$s independently represents a hydrocarbon group having 1 to 18 carbon atoms; this hydrocarbon group is preferably a linear or branched alkyl group having 1 to 18 carbon atoms; l, r, s=1 to 5.

u-4: in u-3, l, r, s=1 to 3.

u-5: in u-4, at least one of $R^{1a}$, $R^{1d}$ and $R^{2d}$ independently represents a branched alkyl group having 3 to 8 carbon atoms.

u-6: in u-4, l, r, s=1; each of $R^{1a}$, $R^{1d}$ and $R^{2d}$ independently represents a linear or branched alkyl group having 1 to 18 (preferably 1 to 10) carbon atoms.

u-7: in u-6, l, r, s=1; each of $R^{1a}$, $R^{1d}$ and $R^{2d}$ independently represents a linear or branched alkyl group having 1 to 10 carbon atoms; this alkyl group preferably has 1 to 8, more preferably 2 to 8, even more preferably 3 to 8, particularly preferably 3 to 5, more particularly preferably 4 to 5, even more particularly preferably 4 carbon atoms.

u-8: in any one of u-3 to u-7, with respect to $PhBzT^{1a}$-S—, $PhBzT^{1d}$-S— and $PhBzT^{2d}$-S—, at least one of $R^{1a}$, $R^{1d}$ and $R^{2d}$ is in the para position.

u-9: in u-4, l, r, s=2; each of $R^{1a}$, $R^{1d}$ and $R^{2d}$ independently represents a linear or branched alkyl group having 1 to 18 (preferably 1 to 10) carbon atoms.

u-10: in u-9, l, r, s=2; each of $R^{1a}$, $R^{1d}$ and $R^{2d}$ independently represents a linear or branched alkyl group having 1 to 10 carbon atoms; each of these alkyl groups preferably has 1 to 5, more preferably 1 to 4, even more preferably 1 carbon atom(s); and/or a total number of the carbon atoms in these alkyl groups is preferably 2 to 12, more preferably 2 to 10, even more preferably 2 to 5, particularly preferably 2.

u-11: in any one of u-9 and u-10, with respect to $PhBzT^{1a}$-S—, $PhBzT^{1d}$-S— and $PhBzT^{2d}$-S—, $R^{1a}$, $R^{1d}$ and $R^{2d}$, when l, r, s=2, are each in the ortho, para positions or the ortho, meta positions.

u-12: in any one of u-3 to u-11, each of $R^{1a}$, $R^{1d}$ and $R^{2d}$ independently represents a tertiary and/or quaternary carbon-containing hydrocarbon group, preferably an alkyl group.

u-13: in u-1, each of the l $R^{1a}$s, r $R^{1d}$s and s $R^{2d}$s independently represents an alkoxy group possessing a linear or branched alkyl group having 1 to 18 carbon atoms, preferably an alkoxy group possessing a linear alkyl group having 1 to 8 carbon atoms, more preferably an alkoxy group possessing a linear alkyl group having 1 to 4 carbon atoms; preferably l, r, s=1 to 3, more preferably l, r, s=1 to 2, particularly preferably l, r, s=1.

u-14: in u-13, l, r, s=1, the alkoxy group is in the meta position with respect to $PhBzT^{1a}$-S—, $PhBzT^{1d}$-S— and $PhBzT^{2d}$-S—.

u-15: in u-1, the l $R^{1a}$s, r $R^{1d}$s and s $R^{2d}$s are hydroxy groups; preferably l, r, s=1 to 3, more preferably l, r, s=1 to 2, particularly preferably l, r, s=1.

u-16: in u-15, l, r, s=1, the hydroxy group(s) is in the para position with respect to $PhBzT^{1a}$-S—, $PhBzT^{1d}$-S— and $PhBzT^{2d}$-S—.

u-17: $X^{1a}$, $X^{1d}$ and $X^{2d}$ are residues of naphthyl rings; preferably l, r, s=0

Although not particularly limited, examples of the 2-phenylbenzotriazole derivative represented by the formula (1) include 5-phenylthio-2-(2-hydroxy-3-tert-butyl-5-methylphenyl)-2H-benzotriazole, 5-(4-tert-butyl-phenylthio)-2-(2-hydroxy-3-tert-butyl-5-methylphenyl)-2H-benzotriazole, 5-(2,4-dimethyl-phenylthio)-2-(2-hydroxy-3-tert-butyl-5-methylphenyl)-2H-benzotriazole, 5-(3-methoxy-phenylthio)-2-(2-hydroxy-3-tert-butyl-5-methylphenyl)-2H-benzotriazole, 5-(4-(1,1-dimethyl-propyl)-phenylthio)-2-(2-hydroxy-3-tert-butyl-5-methylphenyl)-2H-benzotriazole, 5-(4-isopropyl-phenylthio)-2-(2-hydroxy-3-tert-butyl-5-methylphenyl)-2H-benzotriazole, 5-(4-(1,1,3,3-tetramethyl-butyl)-phenylthio)-2-(2-hydroxy-3-tert-butyl-5-methylphenyl)-2H-benzotriazole, 5-(2-methyl-5-tert-butyl-phenylthio)-2-(2-hydroxy-3-tert-butyl-5-methylphenyl)-2H-benzotriazole, 5-(4-methyl-phenylthio)-2-(2-hydroxy-3-tert-butyl-5-methylphenyl)-2H-benzotriazole, 5-(2,4-di(1,1-dimethylpropyl)-phenylthio)-2-(2-hydroxy-3-tert-butyl-5-methylphenyl)-2H-benzotriazole, 5-(4-hydroxy-phenylthio)-2-(2-hydroxy-3-tert-butyl-5-methylphenyl)-2H-benzotriazole, 5-naphthylthio-2-(2-hydroxy-3-tert-butyl-5-methylphenyl)-2H-benzotriazole and 5-phenylthio-2-(2-hydroxy-5-methylphenyl)-2H-benzotriazole.

(2-phenylbenzotriazole Derivative that Contains a thiocyclohexyl Ring Group ($-S-Cy-$ . . . ) and is Represented by the Formula (2))

Preferable examples of combinations of the m $R^{1b}$s in the formula (2) are as follows.

e-1: m=0; no substituent group $R^{1b}$ is present at Cy, moieties of Cy that are substitutable by $R^{1b}$ are all hydrogen atoms.

e-2: each of the m $R^{1b}$s independently represents a hydrocarbon group having 1 to 18 carbon atoms; the hydrocarbon group is preferably a linear or branched alkyl group having 1 to 18 carbon atoms; m=1 to 5.

e-3: in e-2, m=1 to 3.

e-4: in e-3, at least one $R^{1b}$ independently represents a branched alkyl group having 3 to 8 carbon atoms.

e-5: in e-3, m=1; $R^{16}$ represents a linear or branched alkyl group having 1 to 18 (preferably 1 to 10) carbon atoms.

e-6: in e-5, m=1; $R^{16}$ represents a linear or branched alkyl group having 1 to 10 carbon atoms; this alkyl group preferably has 1 to 8, more preferably 2 to 8, even more preferably 3 to 8, particularly preferably 3 to 5, more particularly preferably 4 to 5, even more particularly preferably 4 carbon atoms.

e-7: in any one of e-2 to e-6, with respect to $PhBzT^{1b}$-S—, at least one $R^{1b}$ is in the para position.

e-8: in e-3, m=2; each $R^{1b}$ independently represents a linear or branched alkyl group having 1 to 18 (preferably 1 to 10) carbon atoms.

e-9: in e-8, m=2; each $R^{1b}$ independently represents a linear or branched alkyl group having 1 to 10 carbon atoms; each alkyl group preferably has 1 to 5, more preferably 1 to 4, even more preferably 1 carbon atom(s); and/or a total number of the carbon atoms in these alkyl groups is preferably 2 to 12, more preferably 2 to 10, even more preferably 2 to 5, particularly preferably 2.

e-10: in any one of e-8 and e-9, with respect to $PhBzT^{1b}$-S—, $R^{1b}$, when m=2, is in the ortho, para or ortho, meta position.

e-11: in any one of e-2 to e-10, $R^{1b}$ represents a tertiary and/or quaternary carbon-containing hydrocarbon group, preferably a branched alkyl group.

e-12: in e-1, each of the m $R^{1b}$s independently represents an alkoxy group possessing a linear or branched alkyl group having 1 to 18 carbon atoms, preferably an alkoxy group possessing a linear alkyl group having 1 to 8 carbon atoms, more preferably an alkoxy group possessing a linear alkyl group having 1 to 4 carbon atoms; preferably m=1 to 3, more preferably m=1 to 2, particularly preferably m=1.

e-13: in e-12, m=1; with respect to $PhBzT^{1b}$-S—, the alkoxy group is in the meta position.

e-14: in e-1, the m $R^{1b}$s are hydroxy groups; preferably m=1 to 3, more preferably m=1 to 2, particularly preferably m=1.

e-15: in e-14, m=1; with respect to $PhBzT^{1b}$-S—, the hydroxy group is in the para position.

Although not particularly limited, examples of the 2-phenylbenzotriazole derivative represented by the formula (2) include 5-cyclohexylthio-2-(2-hydroxy-3-tert-butyl-5-methylphenyl)-2H-benzotriazole, 5-(4-methyl-cyclohexyl)-thio-2-(2-hydroxy-3-tert-butyl-5-methylphenyl)-2H-benzotriazole, 5-(4-methoxy-cyclohexyl)-thio-2-(2-hydroxy-3-tert-butyl-5-methylphenyl)-2H-benzotriazole and 5-(4-isopropyl-cyclohexyl)-thio-2-(2-hydroxy-3-tert-butyl-5-methylphenyl)-2H-benzotriazole.

(2-phenylbenzotriazole Derivative that Contains a Thioaryl Ring Group (—S-$A^{1c}$-S—) and is Represented by the Formula (3))

In the formula (3), $A^{2c}$ represents a divalent hydrocarbon group that has 1 to 20 carbon atoms and may have the hydrogen atoms therein substituted by, at least one of the two ends thereof interrupted by, or the carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom; a divalent aromatic group; or a sulfide group —S—.

Examples of the divalent hydrocarbon group having 1 to 20 carbon atoms, as represented by $A^{2c}$, include an aliphatic hydrocarbon group, an alicyclic hydrocarbon group and an aromatic hydrocarbon group. Among them, an aliphatic hydrocarbon group is preferred, examples of which include a linear or branched alkylene group, a linear or branched alkenylene group, and a linear or branched alkynylene group. Although not particularly limited, specific examples of such divalent hydrocarbon group include a methylene group, 1,1-dimethyl-methylene group, ethane-1,2-diyl group, propane-1,3-diyl group, propane-2,2-diyl group, 1-methylethane-1,2-diyl group, butane-1,4-diyl group, butane-1,3-diyl group, 2-methylpropane-1,3-diyl group, pentane-1,5-diyl group, pentane-1,4-diyl group, hexane-1,6-diyl group, heptane-1,7-diyl group, octane-1,8-diyl group, nonane-1,9-diyl group, decane-1,10-diyl group, undecane-1,11-diyl group, dodecane-1,12-diyl group, tridecane-1,13-diyl group, tetradecane-1,14-diyl group, pentadecane-1,15-diyl group, hexadecane-1,16-diyl group, heptadecane-1,17-diyl group, octadecane-1,18-diyl group, nonadecane-1,19-diyl group and eicosane-1,20-diyl group. Among these examples, linear or branched alkylene groups are preferred, and branched alkylene groups are more preferred.

When the divalent hydrocarbon group is such a group with the hydrogen atoms therein substituted by, at least one of the two ends thereof interrupted by, or the carbon-carbon bonds therein interrupted by the monovalent or divalent group(s), there are no particular limitations on the number of the monovalent or divalent groups; for example, the number of such groups may be not larger than two, or not larger than one.

Specific examples of the aromatic group, unsaturated group, nitrogen-containing group, sulfur-containing group, oxygen-containing group, phosphorus-containing group, alicyclic group and halogen atom as the monovalent or divalent groups include those similar to the monovalent or divalent groups listed as the substituent groups of $R^1$ to $R^9$ in the 2-phenylbenzotriazole skeleton represented by the formula (A) to which the descriptions thereof are referred.

The divalent aromatic group represented by $A^{2c}$ has an aromatic ring such as a benzene ring, a naphthalene ring and an anthracene ring, and preferably has 6 to 18, more preferably 6 to 14 carbon atoms. Although not particularly limited, examples of such divalent aromatic group include a 1,4-phenylene group, 1,3-phenylene group, 1,2-phenylene group, 1,8-naphthylene group, 2,7-naphthylene group, 2,6-naphthylene group, 1,4-naphthylene group, 1,3-naphthylene group, 9,10-anthracenylene group, 1,8-anthracenylene group, 2,7-anthracenylene group, 2,6-anthracenylene group, 1,4-anthracenylene group and 1,3-anthracenylene group.

As for the formula (3), preferable examples of combinations of the n $R^{1c}$s and $X^{1c}$, p $R^{2c}$s and $X^{2c}$, and q $A^{2c}$s are as follows.

o-1: $X^{1c}$ and $X^{2c}$ are residues of phenyl rings.

o-2: in o-1, n, p=0; substituent groups $R^{1c}$ and $R^{2c}$ are not present at $X^{1c}$ and $X^{2c}$; moieties of X's and $X^{2c}$ that are substitutable by $R^{1c}$ and $R^{2c}$ are all hydrogen atoms.

o-3: in o-1, each of the n $R^{1c}$s and p $R^{2c}$s independently represents a hydrocarbon group having 1 to 18 carbon atoms; the hydrocarbon group is preferably a linear or branched alkyl group having 1 to 18 carbon atoms; n, p=1 to 5.

o-4: in o-3, n, p=1 to 3.

o-5: in o-4, at least one of $R^{1c}$ and $R^{2c}$ independently represents a branched alkyl group having 3 to 8 carbon atoms.

o-6: in o-4, n, p=1; each of $R^{1c}$ and $R^{2c}$ independently represents a linear or branched alkyl group having 1 to 18 (preferably 1 to 10) carbon atoms.

o-7: in o-6, n, p=1; each of $R^{1c}$ and $R^{2c}$ independently represents a linear or branched alkyl group having 1 to 10 carbon atoms; this alkyl group preferably has 1 to 8, more preferably 2 to 8, even more preferably 3 to 8, particularly preferably 3 to 5, more particularly preferably 4 to 5, even more particularly preferably 4 carbon atoms.

o-8: in o-4, n, p=2; each of $R^{1c}$ and $R^{2c}$ independently represents a linear or branched alkyl group having 1 to 18 (preferably 1 to 10) carbon atoms.

o-9: in o-8, n, p=2; each of $R^{1c}$ and $R^{2c}$ independently represents a linear or branched alkyl group having 1 to 10 carbon atoms; each alkyl group preferably has 1 to 5, more preferably 1 to 4, even more preferably 1 carbon atom(s); and/or a total number of the carbon atoms in these alkyl groups is preferably 2 to 12, more preferably 2 to 10, even more preferably 2 to 5, particularly preferably 2.

o-10: in any one of o-3 to o-9, each of $R^{1c}$ and $R^{2c}$ independently represents a tertiary and/or quaternary carbon-containing hydrocarbon group, preferably an alkyl group.

o-11: in o-1, each of the n $R^{1c}$s and p $R^{2c}$s independently represents an alkoxy group possessing a linear or branched alkyl group having 1 to 18 carbon atoms, preferably an alkoxy group possessing a linear alkyl group having 1 to 8 carbon atoms, more preferably an alkoxy group possessing a linear alkyl group having 1 to 4 carbon atoms; preferably n, p=1 to 3, more preferably n, p=1 to 2, particularly preferably n, p=1.

o-12: in o-1, the n $R^{1c}$s and p $R^{2c}$s are hydroxy groups; preferably n, p=1 to 3, more preferably n, p=1 to 2, particularly preferably n, p=1.

o-13: $X^{1c}$ and $X^{2c}$ are residues of naphthyl rings; preferably n, p=0.

o-14: in any one of o-1 to o-13, q=1, $A^{2c}$ is a sulfide group; preferably n, p=0, substituent groups $R^{1c}$ and $R^{2c}$ are not present at $X^{1c}$ and $X^{2c}$, moieties of $X^{1c}$ and $X^{2c}$ that are substitutable by $R^{1c}$ and $R^{2c}$ are all hydrogen atoms.

o-15: in any one of o-1 to o-13, q=1, $A^{2c}$ is a hydrocarbon group having 1 to 8 (preferably 1 to 4) carbon atoms (preferably a linear or branched alkylene group); preferably n, p=0, substituent groups $R^{1c}$ and $R^{2c}$ are not present at $X^{1c}$ and $X^{2c}$, moieties of $X^{1c}$ and $X^{2c}$ that are substitutable by $R^{1c}$ and $R^{2c}$ are all hydrogen atoms.

o-16: in any one of o-1 to o-13, q=0; preferably n, p=0, substituent groups $R^{1c}$ and $R^{2c}$ are not present at $X^{1c}$ and $X^{2c}$, moieties of $X^{1c}$ and $X^{2c}$ that are substitutable by $R^{1c}$ and $R^{2c}$ are all hydrogen atoms.

o-17: in any one of o-1 to o-16, with respect to $PhBzT^{1c}$-S—, $PhBzT^{2c}$-S—, $-(A^{1c})_q$- is in the para position.

Although not particularly limited, examples of the 2-phenylbenzotriazole derivative represented by the formula (3) include 4,4'-thiobis [(2-hydroxy-3-tert-butyl-5-methylphenyl)-2H-benzotriazole-5-yl-thiobenzene], 4,4-propane-2,2-diyl-bis [(2-hydroxy-3-tert-butyl-5-methylphenyl)-2H-benzotriazole-5-yl-thiobenzene] and 4,4'-biphenyl-bis [(2-hydroxy-3-tert-butyl-5-methylphenyl)-2H-benzotriazole-5-yl-thio].

(2-phenylbenzotriazole Derivative Having Thioaryl Ring Group (—S—$X^{1d}$— . . . Or —S—$X^{2d}$— . . . ) at Position-5, as Represented by the Formula (4))

In the formula (4), $A^{1d}$ represents a divalent hydrocarbon group that has 1 to 20 carbon atoms and may have the hydrogen atoms therein substituted by, at least one of the two ends thereof interrupted by, or the carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom.

The divalent hydrocarbon group having 1 to 20 carbon atoms, as represented by $A^{1d}$, is similar to the above divalent hydrocarbon group having 1 to 20 carbon atoms, as represented by $A^{2c}$ in the formula (3) to which the descriptions thereof are referred. As for the monovalent or divalent group(s) selected from an aromatic group, an unsaturated group, a nitrogen-containing group, a sulfur-containing group, an oxygen-containing group, a phosphorus-containing group, an alicyclic group and a halogen atom to which the descriptions thereof are referred.

A divalent aromatic group represented by $A^{1d}$ is similar to the divalent aromatic group represented by $A^{2c}$ in the formula (3) to which the descriptions thereof are referred.

Although not particularly limited, examples of the 2-phenylbenzotriazole derivative having the thioaryl ring group (—S—$X^{1d}$— . . . or —S—$X^{2d}$— . . . ) at the position-5, as represented by the formula (4), include 2,2'-methylenebis [6-(2H-benzotriazole-5-yl-(4-tert-butyl-thiophenyl))-4-(4-(1,1,3,3-tetramethyl-butyl) phenol] and 2,2'-methylenebis [6-(2H-benzotriazole-5-yl-(4-tert-butyl-thiophenyl))-4-(2-hydroxyethyl) phenol].

While the examples of the ultraviolet absorber of the present invention have been described so far, preferable embodiments of a highly light-resistant ultraviolet absorber in particular are further shown below.

The 2-phenylbenzotriazole derivative is represented by any one of the formulae (1), (3) and (4) in [I]; $X^{1a}$, $X^{1c}$, $X^{2c}$, $X^{1d}$ and $X^{2d}$ in the formulae (1), (3) and (4) represent residues of phenyl rings; l, n, p, r and s represent 0.

Particularly, the 2-phenylbenzotriazole derivative is represented by any one of the formulae (1) and (3); $X^{1a}$, $X^{1c}$ and $X^{2c}$ in the formulae (1) and (3) represent residues of phenyl rings; l, n and p represent 0; a hydroxy group is present at $R^1$, and a methyl group is present at $R^4$, in the 2-phenylbenzotriazole skeleton.

The 2-phenylbenzotriazole derivative is represented by any one of the formulae (1), (3) and (4) in [I]; $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a hydrocarbon group having 1 to 18 carbon atoms; l, n, p, r and s each represent an integer of 1 to 5.

Particularly, $X^{1a}$, $X^{1c}$, $X^{2c}$, $X^{1d}$ and $X^{2d}$ in the formulae (1), (3) and (4) represent residues of phenyl rings; at least one of the l $R^{1a}$s, n $R^{1c}$s, p $R^{2c}$s, r $R^{1d}$s and s $R^{2d}$s independently represents a branched alkyl group having 3 to 8 carbon atoms; l, n, p, r and s each represent an integer of 1 to 3.

Alternatively, $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 1 to 18 carbon atoms; l, n, p, r and s each represent an integer of 1.

Alternatively, $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 1 to 18 carbon atoms; l, n, p, r and s each represent an integer of 2.

Alternatively, $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a tertiary and/or quaternary carbon-containing hydrocarbon group having 1 to 18 carbon atoms; l, n, p, r and s each represent an integer of 1 to 5.

The 2-phenylbenzotriazole derivative is represented by any one of the formulae (1), (3) and (4) in [I]; $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents an alkoxy group possessing a linear or branched alkyl group having 1 to 18 carbon atoms.

The 2-phenylbenzotriazole derivative is represented by any one of the formulae (1), (3) and (4) in [I]; $X^{1a}$, $X^{1c}$, $X^{2c}$, $X^{1d}$ and $X^{2d}$ in the formulae (1), (3) and (4) represent residues of phenyl rings; the l $R^{1a}$s, n $R^{1c}$s, p $R^{2c}$s, r $R^{1d}$s and s $R^{2d}$s represent hydroxy groups.

The 2-phenylbenzotriazole derivative is represented by any one of the formulae (1), (3) and (4) in [I]; $X^{1a}$, $X^{1c}$, $X^{2c}$, $X^{1d}$ and $X^{2d}$ in the formulae (1), (3) and (4) represent residues of naphthyl rings.

The 2-phenylbenzotriazole derivative is represented by the formula (2) in [I]; in the formula (2), m represents 0.

The 2-phenylbenzotriazole derivative is represented by the formula (2) in [I]; in the formula (2), each $R^{1b}$ independently represents a hydrocarbon group having 1 to 18 carbon atoms.

The 2-phenylbenzotriazole derivative is represented by the formula (3) in [I]; in the formula (3), $X^{1c}$ and $X^{2c}$ represent residues of phenyl rings, q represents 1, and $A^{2c}$ represents a sulfide group —S—.

The 2-phenylbenzotriazole derivative is represented by the formula (3) in [I]; in the formula (3), $X^{1c}$ and $X^{2c}$ represent residues of phenyl rings, q represents 1, and $A^{2c}$ represents a hydrocarbon group having 1 to 8 carbon atoms.

The 2-phenylbenzotriazole derivative is represented by the formula (3) in [I]; in the formula (3), $X^{1c}$ and $X^{2c}$ represent residues of phenyl rings, and q represents 0.

Further, preferable embodiments of a heat-resistant ultraviolet absorber are shown below.

The 2-phenylbenzotriazole derivative is represented by the formulae (1), (3) and (4) in [II]; $X^{1a}$, $X^{1c}$, $X^{2c}$, $X^{1d}$ and $X^{2d}$ in the formulae (1), (3) and (4) represent residues of phenyl rings.

The 2-phenylbenzotriazole derivative is represented by the formulae (1), (3) and (4) in [II]; $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 1 to 18 (preferably 1 to 10) carbon atoms; l, n, p, r and s each represent an integer of 0 to 3.

The 2-phenylbenzotriazole derivative is represented by the formulae (1), (3) and (4) in [II]; $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 1 to 18 (preferably 1 to 10) carbon atoms; l, n, p, r and s each represent an integer of 1 to 3.

The 2-phenylbenzotriazole derivative is represented by the formulae (1), (3) and (4) in [II]; $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 2 to 8 carbon atoms; l, n, p, r and s each represent an integer of 1 to 3.

The 2-phenylbenzotriazole derivative is represented by the formulae (1), (3) and (4) in [II]; $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 4 to 8 carbon atoms; l, n, p, r and s each represent an integer of 1 to 3.

(Ultraviolet Absorber)

The ultraviolet absorber of the present invention with a thioaryl ring group being introduced into benzotriazole is disclosed in Patent document 2 (WO2016/021664); the ultraviolet absorber is superior in absorbing long-wavelength ultraviolet rays and has an excellent molar extinction coefficient, where members using such ultraviolet absorber can be suppressed from turning yellow. Further, the ultraviolet absorber of the present invention has a high light resistance, exhibits a small change in transmittance (difference in transmittance) caused by the deterioration (decomposition) of the ultraviolet absorber over a long period of time, and is capable of maintaining an ultraviolet absorbing effect through the long-wavelength region; as a preferable embodiment of the highly light-resistant ultraviolet absorber of the present invention, under the following measurement conditions, a difference in transmittance at any one of long wavelengths of 380, 390 and 400 nm is not larger than 6% after irradiating a member with an ultraviolet of a wavelength of 300 to 400 nm for 70 hours. Particularly, an ultraviolet absorber with an even higher light resistance exhibits a difference in transmittance of not lager than 6%, more preferably not larger than 4%, even more preferably not larger than 2%, at each of the wavelengths of 380, 390 and 400 nm. Further, the ultraviolet absorber of the present invention has a high heat resistance such that after adding the ultraviolet absorber to an organic or inorganic material, when heating and processing such organic or inorganic material or when actually using these materials under a high-temperature condition, deterioration in the ultraviolet absorbing effect and discoloration owing to thermal decomposition, for example, can be suppressed. As a preferable embodiment of the heat-resistant ultraviolet absorber of the present invention, it is preferred that discoloration does not occur when heated at 120° C., for 48 hours, more preferably when heated at 160° C., for 6 hours, even more preferably when heated at 160° C., for 12 hours, particularly preferably when heated at 160° C., for 24 hours. And/or, it is preferred that a rate of change in weight due to, for example, the thermal decomposition of the ultraviolet absorber under a long-period heating environment (given temperature for given period of time) be lower than 0.03% by weight after being heated at 120° C., for 48 hours, more preferably lower than 0.20% by weight after being heated at 160° C., for 6 hours, even more preferably lower than 0.08% by weight after being heated at 160° C., for 12 hours, particularly preferably lower than 0.04% by weight after being heated at 160° C., for 24 hours.

Further, since the ultraviolet absorber of the present invention has both a heat resistance and the abovementioned light resistance, it has a high durability and is superior in ultraviolet absorption and discoloration resistance from the production thereof to the point of use. Such preferable embodiment of the durable ultraviolet absorber of the present invention satisfies both of the above preferable embodiments with respect to a high light resistance and a heat resistance.

Further, also from a perspective that the ultraviolet absorber of the present invention is to be contained in an organic or inorganic material before use, the ultraviolet absorber exhibits a superior heat resistance and light resistance, and an excellent affinity to the organic or inorganic material, thereby contributing to the maintenance of an ultraviolet absorption capability of the organic or inorganic material, a discoloration resistance thereof and a superior appearance thereof. Particularly, when a resin is used as an organic material, the ultraviolet absorber is superior in that it is capable of suppressing the deterioration of the resin without causing bleed-out; when glass is used as an inorganic material, the ultraviolet absorber is superior in that it is capable of maintaining the ultraviolet absorption capability of the glass.

<Condition for Measuring Difference in Transmittance (ΔTuv)>

A sample prepared by applying to a soda glass an acrylic resin and the ultraviolet absorber at a mass ratio of 0.6 to 3.4:0.1 and at a film thickness of 2 to 50 µm is irradiated with an ultraviolet for 70, 140 hours under a condition(s) of wavelength 300 to 400 nm, irradiance 42 W/m², black panel temperature 63° C. Based on a transmittance by UV-Vis transmission spectrum before irradiation ($T_1$uv) and a transmittance by UV-Vis transmission spectrum after irradiation ($T_2$uv), calculation is performed using the following formula.

$$\text{Difference in transmittance } (\Delta Tuv) = T_1uv - T_2uv \ (\%) \quad \text{[Formula 1]}$$

The light resistance of the ultraviolet absorber of the present invention is affected by $X^{1a}$ in the formula (1), Cy in the formula (2), $X^{1c}$ and $X^{2c}$ in the formula (3), and $X^{1d}$ and $X^{2d}$ in the formula (4); further, the light resistance can be improved depending on whether a substituent group(s) are present at each of $X^{1a}$, Cy, $X^{1c}$, $X^{2c}$, $X^{1d}$ and $X^{2d}$ or by selecting appropriate substituent groups $R^{1a}$, $R^{1b}$, $R^{1c}$ and $R^{2c}$ as well as $R^{1d}$ and $R^{2d}$. For example, as for $X^{1a}$, $X^{1c}$, $X^{2c}$, $X^{1d}$ and $X^{2d}$ in the formulae (1), (3) and (4), residues of phenyl rings are more preferable than residues of naphthyl rings, and as for $R^{1a}$, $R^{1c}$, $R^{2c}$, $R^{1d}$ and $R^{2d}$, hydrocarbon groups and alkoxy groups are more preferable than hydroxy groups, and a linear or branched alkyl group is preferred even among hydrocarbon groups, which brings about a high light resistance.

Further, in the formula (1), it is preferred that $X^{1a}$ represent a residue of a phenyl ring, l=1 to 3, and least one $R^{1a}$ represent a branched alkyl group having 3 to 8 carbon atoms; differences in transmittance at each of the wavelengths of 380, 390 and 400 nm are all not larger than 6.0 after irradiation for 70 hours.

When $X^{1a}$ is a residue of a phenyl ring, l=1, and $R^{1a}$ is a linear or branched alkyl group, it is preferred that the alkyl group have 1 to 18 carbon atoms; differences in transmittance at each of the wavelengths of 380, 390 and 400 nm are all not larger than 6.0 after irradiation for 70 hours.

it is preferred that the alkyl group have 1 to 10 carbon atoms; differences in transmittance at each of the wavelengths of 380, 390 and 400 nm are all not larger than 6.0 after irradiation for 70 hours.

it is preferred that the alkyl group have 1 to 8 carbon atoms; differences in transmittance at each of the wavelengths of 380, 390 and 400 nm are all not larger than 6.0 after irradiation for 70 hours.

it is more preferred that the alkyl group have 2 to 8 carbon atoms; differences in transmittance at each of the wavelengths of 380, 390 and 400 nm are all not larger than 4.0 after irradiation for 70 hours, and differences in transmittance at two of the wavelengths of 380, 390 and 400 nm are not larger than 6.0 after irradiation for 140 hours.

it is even more preferred that the alkyl group have 3 to 8 carbon atoms; differences in transmittance at each of the wavelengths of 380, 390 and 400 nm are all not larger than 4.0 after irradiation for 70 hours, and differences in transmittance at two of the wavelengths of 380, 390 and 400 nm are not larger than 6.0 after irradiation for 140 hours.

it is particularly preferred that the alkyl group have 3 to 5 carbon atoms; differences in transmittance at each of the wavelengths of 380, 390 and 400 nm are all not larger than 4.0 after irradiation for 70 hours, and differences in transmittance at each of the wavelengths of 380, 390 and 400 nm are all not larger than 6.0 after irradiation for 140 hours.

it is more particularly preferred that the alkyl group have 4 to 5 carbon atoms; differences in transmittance at each of the wavelengths of 380, 390 and 400 nm are all not larger than 4.0 after irradiation for 70 hours, a difference in transmittance at one of the wavelengths of 380, 390 and 400 nm is not larger than 6.0 after irradiation for 140 hours, and differences in transmittance at two of the wavelengths of 380, 390 and 400 nm are not larger than 4.0 after irradiation for 140 hours.

it is even more particularly preferred that the alkyl group have 4 carbon atoms; differences in transmittance at each of the wavelengths of 380, 390 and 400 nm are all not larger than 2.0 after irradiation for 70 hours, and differences in transmittance at each of the wavelengths of 380, 390 and 400 nm are all not larger than 4.0 after irradiation for 140 hours.

it is preferred that $R^{1a}$ represent a tertiary and/or quaternary carbon-containing alkyl group; differences in transmittance at each of the wavelengths of 380, 390 and 400 nm are all not larger than 4.0 after irradiation for 70 hours.

When $X^{1a}$ is a residue of a phenyl ring, l=2, and $R^{1a}$ is a linear or branched alkyl group, it is preferred that each alkyl group have 1 to 18 carbon atoms; differences in transmittance at each of the wavelengths of 380, 390 and 400 nm are all not larger than 6.0 after irradiation for 70 hours.

it is preferred that each alkyl group have 1 to 10 carbon atoms; differences in transmittance at each of the wavelengths of 380, 390 and 400 nm are all not larger than 6.0 after irradiation for 70 hours.

it is preferred that each alkyl group have 1 to 5 carbon atoms; differences in transmittance at each of the wavelengths of 380, 390 and 400 nm are all not larger than 6.0 after irradiation for 70 hours.

it is more preferred that each alkyl group have 1 to 4 carbon atoms; differences in transmittance at each of the wavelengths of 380, 390 and 400 nm are all not larger than 4.0 after irradiation for 70 hours.

it is even more preferred that each alkyl group have 1 carbon atom; differences in transmittance at each of the wavelengths of 380, 390 and 400 nm are all not larger than 2.0 after irradiation for 70 hours.

it is preferred that the total number of the carbon atoms in the alkyl groups be 2 to 12; differences in transmittance at each of the wavelengths of 380, 390 and 400 nm are all not larger than 6.0 after irradiation for 70 hours.

it is more preferred that the total number of the carbon atoms in the alkyl groups be 2 to 10; differences in transmittance at each of the wavelengths of 380, 390 and 400 nm are all not larger than 6.0 after irradiation for 70 hours.

it is even more preferred that the total number of the carbon atoms in the alkyl groups be 2 to 5; differences in transmittance at each of the wavelengths of 380, 390 and 400 nm are all not larger than 4.0 after irradiation for 70 hours.

it is particularly preferred that the total number of the carbon atoms in the alkyl groups be 2; differences in transmittance at each of the wavelengths of 380, 390 and 400 nm are all not larger than 2.0 after irradiation for 70 hours.

Further, it is preferred that l=0 i.e. the substituent groups at $X^{1a}$ are all hydrogen atoms; differences in transmittance at each of the wavelengths of 380, 390 and 400 nm are all not larger than 2.0 after irradiation for 70, 140 hours.

Meanwhile, in the formula (3), it is more preferred that q=1, and $A^{2c}$ be a sulfide group; differences in transmittance at each of the wavelengths of 380, 390 and 400 nm are all not larger than 2.0 after irradiation for 70 hours.

it is preferred that q=1, and $A^{2c}$ have 1 to 8 carbon atoms; differences in transmittance at each of the wavelengths of 380, 390 and 400 nm are all not larger than 2.0 after irradiation for 70 hours, and differences in transmittance at each of the wavelengths of 380, 390 and 400 nm are all not larger than 4.0 after irradiation for 140 hours.

it is preferred that q=0; differences in transmittance at each of the wavelengths of 380, 390 and 400 nm are all not larger than 6.0 after irradiation for 70 hours.

In general, if an ultraviolet absorber is to be added to a resin as a material, a compound with a low melting point will exhibit a time-course bleed-out of the ultraviolet absorber early; meanwhile, for example, bleed-out or decomposition will occur when processing and molding an inorganic material such as a thermoplastic resin and glass via heating, thus failing to sufficiently exert the ultraviolet absorbing effect, or causing blocking or the like. When pulverizing (microparticulating), dispersing an ultraviolet absorber before use, an ultraviolet absorber with a low melting point will agglutinate due to a heat generated during these step(s), which makes it difficult for the ultraviolet absorber to be used; an ultraviolet absorber with a high melting point is thus rather desired, and a light absorbing property can be maintained if the ultraviolet absorber also has a light resistance. From these perspectives, the highly light-resistant ultraviolet absorber of the present invention preferably has a melting point of not lower than 100° C., more preferably not lower than 130° C., even more preferably not lower than 140° C., particularly preferably not lower than 145° C., more particularly preferably not lower than 150° C. In terms of melting point, it is preferred that $X^{1a}$ in the formula (1) be a naphthyl ring. When $X^{1a}$ is a residue of a phenyl ring, it is preferred that $R^{1a}$ be a hydroxy group; when $R^{1a}$ is a linear or branched alkyl group, it is preferred that l=1 rather than l=0. When l=1, it is preferred that the alkyl group has 2 to 8 carbon atoms, more preferably 3 to 8 carbon atoms, even more preferably 3 to 4 carbon atoms. In the formula (3), when q=1, it is preferred that $A^{2c}$ be a hydrocarbon group (preferably a linear or branched alkylene group). It is more preferred that q=0.

As mentioned above, after adding an ultraviolet absorber to an organic or inorganic material, when heating and processing such organic or inorganic material to which the ultraviolet absorber has been added and when using these materials under a high-temperature condition, not only the ultraviolet absorbing effect cannot be fully exhibited as the ultraviolet absorber decomposes, but the ultraviolet absorber-containing material(s) will discolor due to a discoloration owing to the thermal decomposition of the ultraviolet absorber. Therefore, a heat resistance is required for an ultraviolet absorber, and desired is a type of ultraviolet absorber exhibiting a small degree of discoloration and loss in weight owing to thermal decomposition when heated. The thermal decomposition of an ultraviolet absorber under a long-period heating (production, usage) environment (given temperature for given period of time) causes a loss in weight and discoloration; the smaller the degree of discoloration is, the lower the rate of change in weight is.

In terms of discoloration, it is desired that a small degree of discoloration be observed when the material has been heated at a higher temperature for a longer period of time; for example, yellow is preferred rather than black, light yellow is more preferred, and it is even more preferred that discoloration does not occur.

As described above, the ultraviolet absorber of the present invention is superior in light resistance, heat resistance and durability; when used in a resin as an organic material, the ultraviolet absorber of the invention is capable of preventing the deterioration of the resin composition, and maintaining the ultraviolet absorption capability and appearance of the resin composition for a long period of time.

For example, as an index of discoloration of an ultraviolet absorber that has been left to stand still in a thermostatic device under a heating environment where heating is performed at a given temperature for a given period of time, it is preferred that the ultraviolet absorber does not discolor after being heated at 120° C., for 48 hours, more preferably at 160° C., for 6 hours, even more preferably at 160° C., for 12 hours, particularly preferably at 160° C., for 24 hours.

In terms of rate of loss in weight, it is desired that a low rate of loss in weight be observed when the material has been heated at a higher temperature for a longer period of time; for example, it is preferred that the rate of loss in weight be lower than 0.20% by weight, more preferably lower than 0.08% by weight, even more preferably lower than 0.04% by weight, particularly preferably lower than 0.03% by weight.

For example, as an index of the rate of change in weight owing to, for example, the thermal decomposition of the ultraviolet absorber after being left to stand still in a thermostatic device under a heating environment where heating is performed at a given temperature for a given period of time, it is preferred that the rate of change in weight be lower than 0.03% by weight after being heated at 120° C., for 48 hours, more preferably lower than 0.20% by weight after being heated at 160° C., for 6 hours, even more preferably lower than 0.08% by weight after being heated at 160° C., for 12 hours, particularly preferably lower than 0.04% by weight after being heated at 160° C., for 24 hours.

In terms of heat resistance under a long-period heating environment (given temperature for given period of time), it is desired that the ultraviolet absorber satisfies the above index of discoloration or the above index of rate of change in weight, and it is more desired that the ultraviolet absorber satisfies a condition combining both of these indexes.

From such perspective of heat resistance, preferred is a compound where $X^{1a}$, $X^{1c}$, $X^{2c}$, $X^{1d}$ and $X^{2d}$ in the formulae (1), (3) and (4) are residues of phenyl rings; more preferred is a compound where $X^{1a}$, $X^{1c}$, $X^{2c}$, $X^{1d}$ and $X^{2d}$ in the formulae (1), (3) and (4) are residues of phenyl rings, each of the l $R^{1a}$s, n $R^{1c}$s, p $R^{2c}$s, r $R^{1d}$s and s $R^{2d}$s independently represents a linear or branched alkyl group having 1 to 18 (preferably 1 to 10) carbon atoms, each of l, n, p, r and s represents an integer of 0 to 3; even more preferred is a compound where each of the l $R^{1a}$s, n $R^{1c}$s, p $R^{2c}$s, r $R^{1d}$s and s $R^{2d}$s in the formulae (1), (3) and (4) independently represents a linear or branched alkyl group having 1 to 18 (preferably 1 to 10) carbon atoms, each of l, n, p, r and s represents an integer of 1 to 3; particularly preferred is a compound where each of the l $R^{1a}$s, n $R^{1c}$s, p $R^{2c}$s, r $R^{1d}$s and s $R^{2d}$s independently represents a linear or branched alkyl group having 2 to 8 carbon atoms, each of l, n, p, r and s represents an integer of 1 to 3; more particularly preferred is a compound where each of the l $R^{1a}$s, n $R^{1c}$s, p $R^{2c}$s, r $R^{1d}$s and s $R^{2d}$s independently represents a linear or branched alkyl group having 4 to 8 carbon atoms, each of l, n, p, r and s represents an integer of 1 to 3.

The inventive ultraviolet absorber may be suitably used for the one of superior durability having desired levels of a change in color and a reduction in weight in terms of heat resistance as mentioned above, in combination with light resistance exhibiting a difference in transmittance of not lager than 6% for at least one of the wavelengths of 380, 390 and 400 nm, and more preferably not larger than 4% for each of the wavelengths of 380, 390 and 400 nm, even more preferably not larger than 2% for each of the wavelengths of 380, 390 and 400 nm. The inventive ultraviolet absorber according to an embodiment of the present invention including the above-noted examples has high light resistance and is rarely deteriorated after being exposed to ultraviolet ray for a long period of use, exhibits ultraviolet absorption capability for a long period of time, and suppresses deterioration of an organic resin. Further, when producing, processing, pulverizing (microparticulating), or dispersing an organic or inorganic material to which the inventive ultraviolet absorber has been added, or when actually using it after being processed, the material undergoes small weight reduction or small color deterioration even when placed under a high-temperature environment for a long period of time (given temperature for given period of time). As shown, in an embodiment of the present invention, there is provided an ultraviolet absorber that provides an organic or inorganic material, from the production thereof to the point of use, which does not cause bleed-out to thereby maintain ultraviolet absorption capability; exhibits a superior light resistance, heat resistance and durability; and exhibits an excellent affinity (adherence) to the organic and inorganic material to thereby obtain a member and the organic and inorganic material which presents favorable appearance.

(Composition)

The term "composition" as used herein may be in any form such as solid, fluid, gel or sol, and includes a composition containing the inventive ultraviolet absorber. The term may also include a member as well as other material for manufacturing such member.

The term "member" as used herein may include, but be not limited to, any substantial matter having any form. The use of the member containing the inventive ultraviolet absorber in respect of the composition may include, for example, those to be described later.

The material of the composition containing the inventive ultraviolet absorber may, for example, be an organic or inorganic material. The inventive ultraviolet absorber has an excellent affinity, compatibility and adherence to a variety of organic or inorganic materials, and is capable of producing homogeneous compositions or members when the inventive ultraviolet absorber is mixed, dissolved, applied or coated thereto. Particularly, the inventive ultraviolet absorber may provide a member superior in transparency when a transparent member is utilized.

The composition containing the inventive ultraviolet absorber includes an organic or inorganic material composition. The form of the organic or inorganic material composition is not particularly limited but may, for example, be in the form of a coating layer, a covered layer, a film stack, a film, a sheet, a plate, a powder, a grain, a pellet, a tablet, or a molded article.

In the organic or inorganic material containing the inventive ultraviolet absorber, the inventive ultraviolet absorber does not cause any bleed-out, and is capable of being used to provide an organic or inorganic material that exhibits not only a superior light resistance but also a superior heat resistance where, for example, there will not be observed a discoloration, deterioration in ultraviolet absorption capability and deterioration in transparency over a long period of use, to thereby suppress a deterioration therein. Further, the inventive ultraviolet absorber has a favorable affinity with organic materials and inorganic materials, and particularly with organic materials.

Due to the above-noted properties of the inventive ultraviolet absorber, the organic materials and inorganic materials, containing it therein, sufficiently absorb harmful lights in a range of 380 to 400 nm while suppressing yellowing, are excellent in appearance, do not cause the ultraviolet absorber to be bleed out, and provide an organic or inorganic material that exhibits not only a superior light resistance but also an excellent heat resistance where, for example, there will not be observed a discoloration, deterioration in ultraviolet absorption capability and deterioration in transparency over a long period of use.

The organic material composition contains an organic material in the amount not smaller than 50 wt. % based on the total material amount exclusive of water, solvent and the inventive ultraviolet absorber. The inorganic material composition contains an inorganic material in the amount not smaller than 50 wt. % based on the total material amount exclusive of water, solvent and the inventive ultraviolet absorber.

The composition containing the inventive ultraviolet absorber may be an organic/inorganic material composition. The organic/inorganic material compositions as used herein refer to the above-mentioned organic material compositions that contain, as a material excluding organic materials, an inorganic material. The organic/inorganic material compositions as used herein refer to the above-mentioned inorganic material compositions that contain, as a material excluding inorganic materials, an organic material. The composition containing the inventive ultraviolet absorber may be a composition, where the raw materials for eventually forming an organic material, inorganic material or a member or the like is added or mixed with. The composition containing the inventive ultraviolet absorber may be a composition, where an organic material composition, an inorganic material composition or an organic/inorganic material composition, respectively containing the inventive ultraviolet absorber, is dispersed, dissolved, or mixed with a liquid such as water or an organic solvent.

The organic material is not particularly limited to but may, for example, be an organic resin, a material of plant/animal origin, a crude oil-derived material, or an organic compound. The organic resin composition as used herein is an organic composition containing the inventive ultraviolet absorber and an organic resin, and is included in the organic material composition.

The organic resin is not particularly limited to but conventionally-known resin, such as thermoplastic resin or thermo-setting resin, may be widely utilized, and these resins include respective polymers that contain one type of repeated unit, or include respective copolymers that contain plural types of repeated units.

In the specific types of resin as described hereunder, the terms thermoplastic resin (polymer or copolymer) and thermosetting resin (polymer or copolymer) as used herein may refer to those including resins that contain not only repeated units as used in normal terminology in the resin but also other repeated units in an amount of not lager than 20 wt %, preferably not larger than 15 wt %, more preferably not larger than 10 wt %, even more preferably not larger than 5 wt %, still more preferably not larger than 2 wt % based on the total amount of the resin. The term may also refer to those including a mixture of the specific types of resins and other resin, whereby the amount of the other resin is not lager than 20 wt %, preferably not larger than 15 wt %, more preferably not larger than 10 wt %, even more preferably not larger than 5 wt %, still more preferably not larger than 2 wt % based on the total amount of the mixture.

Examples of the thermoplastic resin include, but are not limited to, polymers such as a (meth)acryl-based resin, olefin-based resin, styrene-based resin, ester-based resin, ether-based resin, vinyl chloride-based resin, fluorocarbon-based resin, vinyl-based resin, polycarbonate-based resin, polyamide-based resin, polyimide-based resin, polyamide-imide-based resin, polymaleimide-based resin, polyvinylpyrrolidone-based resin, polyurethane-based resin and polysulfone-based resin; and copolymers such as a butadiene-styrene-based copolymer, acrylonitrile-styrene-based copolymer, acrylonitrile-butadiene-styrene-based copolymer, styrene-isoprene-based copolymer, styrene-acrylic acid-based copolymer and vinyl chloride-vinylidene chloride-acrylonitrile-based copolymer. These may be used individually by a single one type or in combination with two or more types.

Examples of the polymers as the thermoplastic resin will be described below, but shall not limited to those.

Examples of the (meth)acryl-based resins include, but are not limited to, poly(meth)acrylate, polymethyl (meth)acrylate, poly(ethyl (meth)acrylate), poly(butyl (meth)acrylate), and poly((meth)acrylonitrile).

Examples of the olefin-based resin include, but are not limited to, polyethylene, polypropylene, polybutene, polybutadiene, polyisoprene, poly (2,3-dimethyl butadiene), poly (cyclohexadiene), poly (cyclopentadiene), poly (dicyclopentadiene), polychloroprene, polynorbornene.

Examples of the styrene-based resin include, but are not limited to, polystyrene.

Examples of the ester-based resin include, but are not limited to, polyethylene terephthalate, polybutylene terephthalate, polycyclohexylenedimethylene terephthalate, polyethylene naphthalate, polybutylene naphthalate, polycaprolactone, poly(ethylene succinate), polylactate, poly(malic acid) and polyglycolic acid.

Examples of the ether-based resin include, but are not limited to, polyacetal, polyphenylene ether, polyetherketone, polyetheretherketone, polyetherketoneketone, polyetheretherketoneketone, polyether sulfone, and polyetherimide.

Examples of the vinyl chloride-based resin include, but are not limited to, polyvinyl chloride and poly vinylidene chloride.

Examples of the fluorocarbon-based resin include, but are not limited to, polytetrafluoroethylene, polyvinyl fluoride and polyvinylidene fluoride.

Examples of the vinyl-based resin include, but are not limited to, polyvinyl acetate, polyvinyl alcohol, poly (vinyl sulfonic acid) and its salt.

Examples of the polycarbonate-based resin include, but are not limited to, polycarbonate.

Examples of the polyamide-based resin include, but are not limited to, polyamide, nylon 6, nylon 66, nylon 11 and nylon 12.

Examples of the polyimide-based resin include, but are not limited to, polyimide.

Examples of the polyamideimide-based resin include, but are not limited to, polyamide imide.

Examples of the polymaleimide-based resin include, but are not limited to, polymaleimide, poly (N-phenylmaleimide).

Examples of the polyvinylpyrrolidone-based resin include, but are not limited to, polyvinylpyrrolidone.

Examples of the polyurethane-based resin include, but are not limited to, polyurethane.

Examples of the polysulfone-based resin include, but are not limited to, polysulfone.

Copolymers of thermoplastic resins are not particularly limited to but include those that contain a multiple of raw monomers of the above-mentioned polymers. The examples of which are as described below.

Examples of the butadiene-styrene-based copolymer include, but are not particularly limited to, butadiene-styrene copolymer.

Examples of the acrylonitrile-styrene-based copolymer include, but are not particularly limited to, acrylonitrile-styrene copolymer.

Examples of the acrylonitrile-butadiene-styrene-based copolymer include, but are not particularly limited to, acrylonitrile-butadiene-styrene copolymer.

Examples of the styrene-isoprene-based copolymer include, but are not particularly limited to, a styrene-isoprene copolymer.

Examples of the styrene-acrylic acid-based copolymers include, but are not particularly limited to, a styrene-acrylic acid copolymer.

Examples of the vinyl chloride-vinylidene chloride-acrylonitrile-based copolymers include, but are not particularly limited to, vinyl chloride-vinylidene chloride-acrylonitrile copolymer.

Examples of the thermosetting resin include, but are not particularly limited to, polymers such as a phenol-based resin, urea-based resin, melamine-based resin, unsaturated polyester-based resin, alkyd-based resin, epoxy-based resin and episulfide-based resin; and copolymers such as an acrylic melamine-based resin and acrylic urethane-based resin. These may be used individually by a single one type or in combination with two or more types.

Polymers of the thermosetting resin include, but are not particularly limited to, the followings.

Examples of the phenol-based resin include, but are not particularly limited to, a phenol resin.

Examples of the urea-based resin include, but are not particularly limited to, a urea-formaldehyde resin.

Examples of the melamine-based resin include, but are not particularly limited to, a melamine resin.

Examples of the unsaturated polyester-based resin include, but are not particularly limited to, an unsaturated polyester resin.

Examples of the alkyd-based resin include, but are not particularly limited to, an alkyd resin.

Examples of the epoxy-based resin include, but are not particularly limited to, an epoxy resin.

Examples of the episulfide-based resin include, but are not particularly limited to, an episulfide resin.

Copolymers of the thermosetting resin include, but are not particularly limited to, the followings.

Examples of the acrylic melamine-based resin include, but are not particularly limited to, an acrylic melamine resin.

Examples of the acrylic urethane-based resin include, but are not particularly limited to, an acrylic urethane resin.

From the perspective of compatibility of the organic resin with the inventive ultraviolet absorber, and the transparency in the organic resin composition containing the ultraviolet absorber, it is preferable that thermoplastic resins (polymers or copolymers) and thermosetting resins (polymers or copolymers) are utilized. Further, among the polymers of thermoplastic resins, preferred are a (meth)acryl-based resin (polymethyl methacrylate resin), ester-based resin (polyethylene terephthalate), polycarbonate-based resin (polycarbonate) and styrene-based resin (polystyrene). Among the copolymers of thermoplastic resins, preferred is an acrylonitrile-butadiene-styrene-based copolymer (acrylonitrile-butadiene-styrene copolymer). Among the polymers of thermosetting resins, preferred are a urea-based resin (urea-formaldehyde resin) and a melamine-based resin (melamine resin). Among the copolymers of thermosetting resins, preferred is an acrylic melamine-based resin (acrylic melamine resin).

From the perspective of compound dispersion, thermal processing, and suppression of elution such as bleed-out from the resin, preferably thermoplastic resins (polymers or copolymers) and thermosetting resins (polymers or copolymers), more preferably thermoplastic polymers and copolymers, and thermosetting polymers may be utilized. Among the polymers for thermoplastic resin, preferred are a (meth) acryl-based resin (polymethyl methacrylate resin), ester-based resin (polyethylene terephthalate), polycarbonate-based resin (polycarbonate) and styrene-based resin (polystyrene), and more preferred are a (meth)acryl-based resin, ester-based resin, polycarbonate-based resin. Among the copolymers for thermoplastic resin, preferred is an acrylonitrile-butadiene-styrene-based copolymer (acrylonitrile-butadiene-styrene copolymer). Among the polymers for thermosetting resin, preferred are a urea-based resin (urea-formaldehyde resin) and melamine-based resin (melamine resin), and a urea-based resin is more preferable.

From the perspective of heat resistance of the organic resin composition containing the inventive ultraviolet absorber, that is, the decrease in transparency over a long-period heating (for given temperature for given period of time), preferred organic resins are thermoplastic resins (polymers or copolymers) and thermosetting resins (polymers or copolymers). Although not particularly limited, among the polymers for thermoplastic resin, preferred are, for example, a (meth)acryl-based resin (polymethyl methacrylate resin), ester-based resin (polyethylene terephthalate), polycarbonate-based resin (polycarbonate) and styrene-based resin (polystyrene). Among the copolymers for thermoplastic resin, preferred is an acrylonitrile-butadiene-styrene-based copolymer (acrylonitrile-butadiene-styrene copolymer). Among the polymers for thermosetting resin, preferred are a urea-based resin (urea-formaldehyde resin) and a melamine-based resin (melamine resin). Examples of the copolymers for thermosetting resins include an acrylic melamine-based resin (acrylic melamine resin). More preferably, polymers for thermoplastic resin and copolymers for thermosetting resin may be utilized. Particularly preferred are thermoplastic resins for which a polycarbonate-based resin (polycarbonate) and (meth)acryl-based resin (polymethyl methacrylate resin) may, for example, be utilized.

Among the inventive ultraviolet absorber, in light of obtaining an organic resin composition excellent in heat resistance, there may be utilized an ultraviolet absorber satisfying the above-mentioned heat resistance conditions in which a preferred is a compound where $X^{1a}$, $X^{1c}$, $X^{2c}$, $X^{1d}$ and $X^{2d}$ in the formulae (1), (3) and (4) are residues of phenyl rings; a more preferred is a compound where $X^{1a}$, $X^{1c}$, $X^{2c}$, $X^{1d}$ and $X^{2d}$ in the formulae (1), (3) and (4) are residues of phenyl rings, each of the $R^{1a}$, $R^{1c}$, $R^{2c}$, $R^{1d}$s and $R^{2d}$, respectively provided in the number of l, n, p, r, and s, independently represents a linear or branched alkyl group having 1 to 18 (preferably 1 to 10) carbon atoms, each of l, n, p, r and s represents an integer of 1 to 3. Even more preferred is a compound where $R^{1a}$, Ric, $R^{2c}$, $R^{1d}$, and $R^{2d}$, respectively provided in the number of l, n, p, r, and s, in the formulae (1), (3) and (4) independently represents a linear or branched alkyl group having 1 to 18 (preferably 1 to 10) carbon atoms, each of l, n, p, r and s represents an integer of 1 to 3. Particularly preferred is a compound where $R^{1a}$, $R^{1c}$, $R^{2c}$, $R^{1d}$ and $R^{2d}$, respectively provided in the number of l, n, p, r, and s, independently represents a linear or branched alkyl group having 2 to 8 carbon atoms, each of l, n, p, r and s represents an integer of 1 to 3. Still more preferred is a compound where $R^{1a}$, $R^{1c}$, $R^{2c}$, $R^{1d}$, and $R^{2d}$, respectively provided in the number of l, n, p, r, and s, independently represents a linear or branched alkyl group having 4 to 8 carbon atoms, each of l, n, p, r and s represents an integer of 1 to 3.

The organic resin composition contains an organic resin in the amount preferably not smaller than 0.001 wt. %, more preferably not smaller than 0.01 wt. %, and even more preferably not smaller than 0.1 wt % based on the total material amount exclusive of the inventive ultraviolet absorber. The organic resin composition may be a composition, where the inventive ultraviolet absorber and the organic resin are dispersed, dissolved, or mixed with each other, or alternatively where the ultraviolet absorber is, dispersed, dissolved, or mixed with the organic resin. To the organic resin composition may be added an inorganic compound, such as the one used as a filler, silane coupling agent or primer.

The examples of the inorganic compound include, but not limited to, a siliceous material by a sol-gel method, glass, liquid glass, low-melting glass, quartz, silicone resin, alkoxysilane, silane coupling agent, metal, metallic oxide, mineral, and other such inorganic compounds. Examples of the glass include, but are not particularly limited to, a silicon oxide, an alkali-free glass and a soda glass.

Examples of the liquid glass include, but are not particularly limited to, an aqueous solution of a water-soluble alkali metal salt such as sodium silicate and potassium silicate. Examples of the low-melting glass include, but are not particularly limited to, glasses containing lead oxide (PbO) and boric anhydride ($B_2O_3$) as major components. Examples of the silicone resin include, but are not particularly limited to, a methyl silicone resin, a methylphenyl silicone resin, and an organic resin-modified silicon resin that has been modified with an epoxy resin, an alkyd resin, a polyester resin or the like. Examples of the alkoxysilane include, for example, dimethoxydimethylsilane, methyphenyldimethoxysilane, methylvinyldimethoxysilane, 3-mercaptopropylmethyldimethoxysilane, 3,3,3-trifluoropropylmethyldimethoxysilane, methyltrimethoxysilane, vinyltrimethoxysilane, and 3-mercaptopropyltrimethoxysilane. Examples of the silane coupling agent include, but are not particularly limited to: 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, 3-glycidoxypropyltriethoxysilane, 3-methacryloxypropylmethyldimethoxysilane, 3-methacryloxypropyltrimethoxysilane, 3-isocyanatepropyltriethoxysilane, N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, 3-aminopropylt- riethoxysilane, 3-triethoxysilyl-N-(1,3-dimethyl-butyl-idene) propylamine, N-phenyl-3-aminopropyltrimethoxysilane, 3-mercaptopropylmethyldimethoxysilane, 3-mercaptopropyltrimethoxysilane, bis(triethoxysilylpropyl) tetrasulfide and 3-isocyanatepropyl ethoxysilane. Examples of the metal include, but are not particularly limited to, Zn, Fe, Cu, Ni, Ag, Si, Ta, Nb, Ti, Zr, Al, Ge, B, Na, Ga, Ce, V, Ta, P, and Sb. Examples of the metallic oxide include, but are not particularly limited to, zinc oxide, titanic oxide, cerium oxide, ferric oxide, tin oxide, indium oxide, and antimony oxide. Examples of the minerals include, but are not particularly limited to, a smectite, bentonite, hectorite and montmorillonite.

Form of the Member

The member is not limited to a specific form but may be in any form, such as, for example, in a form of a coating, an adhesive, a pressure sensitive adhesive, a member in a form of film having bendability or flexibility or of a rigid plate (board), a member in a form of powder, grain, pellet or tablet (pill), a masterbatch and a molded article.

[1] Coating

Examples of the application include a coating to a surface of a member such as resin or glass. Examples of the coating method include, but not particularly limited to, a method for applying, spraying or film-forming, on a surface of the member, a resin, paint, silica material, glass or solvent dispersion liquid to which the inventive ultraviolet absorber is mixed, dissolved or dispersed. The methods also include a method for forming a coated layer containing the inventive ultraviolet absorber.

[2] Adhesive

Examples of the application include, but not particularly limited to, an adhesive in which the inventive ultraviolet absorber is mixed with, dissolved or dispersed in an organic adhesive (such as an organic resin, synthetic rubber, starch or hide glue) or an inorganic adhesive (such as silica, ceramics, cement, solder paste, liquid glass) which are used in various materials or members.

[3] Pressure Sensitive Adhesive

Examples of the application include, but not particularly limited to, a pressure sensitive adhesive in which the inventive ultraviolet absorber is mixed with, dissolved or dispersed in a pressure sensitive adhesive (such as an organic resin, organic oligomer, rubber-based pressure sensitive adhesive, starch, gelatin, silicone-based pressure sensitive adhesive, or a pressure sensitive adhesive based on a silane coupling agent) which is used in various materials or members.

[4] Film

Examples of the application include, but not particularly limited to, a member in which the inventive ultraviolet absorber is mixed with, dissolved or dispersed in a resin, glass or silicon oxide precursor in a form of film having bendability or flexibility. The film may be a monolayer film or a multi-layer film in which one or more layers respectively having suitable functionalities are provided on a base film or basal plate, or be a basal plate provided with film(s). The inventive ultraviolet absorber is contained in at least one of these layers if a plurality of films are provided. A resin or glass in a form of film containing the inventive ultraviolet absorber may be used for an intermediate layer sandwiched between glasses.

[5] Plate

Examples of the plates include, but not particularly limited to, a member in which the inventive ultraviolet absorber is mixed with, dissolved or dispersed in a resin or glass in a form of plate (or board).

[6] Powder, Grain, Pellet, or Tablet (Pill).

Examples of the application include, but not particularly limited to, a member in which the inventive ultraviolet absorber is mixed with, dissolved or dispersed in a resin or glass in a form of powder, grain, pellet or tablet (pill).

[7] Masterbatch

Examples of the application include, but not particularly limited to, a resin composition in a form of powder, grain, pellet or tablet (pill) in which the inventive ultraviolet absorber and, if desired, a coloring agent such as paint are mixed with, dissolved or dispersed in a resin or such. These are used to be melt-mixed with other resins to color or to control the coloring.

[8] Molded Article

Examples of the application include, but not particularly limited to, an article in which the inventive ultraviolet absorber is mixed with, dissolved or dispersed in a resin or glass to mold the article.

Additive

The composition or member having the inventive ultraviolet absorber may contain, but not particularly be limited to, various additives such as antioxidizing agents, heat stabilizers, weather stabilizers, light stabilizers, pigments, dyes, fillers, plasticizers, antistatic agents, nucleating agents, wetting agents, preservatives, fungicides, antifoaming agents, stabilizing agents, antioxidants, chelating agents as long as the composition or the member is not deteriorated in its functionality.

The inventive ultraviolet absorber may be used in a field where an excellent light resistance, heat resistance and durability are required, but the type, form or use of the composition or member is not limited thereto.

The composition or member containing the inventive ultraviolet absorber may be an ultraviolet absorber containing composition that exhibits not only a superior light resistance and heat resistance where, for example, there will not be observed a discoloration, deterioration in ultraviolet absorption capability and deterioration in transparency over a long period of use. For example, in a coating layer, film or the like for a transparent resin or transparent glass, such a coating layer, film or the like can be obtained in which yellowing, discoloration deterioration of ultraviolet absorption and deterioration of transparency do not occur for a long period of time from the production thereof to the point of use.

The inventive ultraviolet absorber is not particularly limited to a specific intended use, but may preferably be used for applications in which exposure to the light having the wavelength of 380 to 400 nm, particularly 380 to 420 nm is expected, or sunlight or the light containing ultraviolet rays is expected.

Though not particularly limited, the applications may include articles or members used in houses, facilities, transportation equipment, displays or the like; interior/exterior materials for houses, facilities, transportation equipment or the like; interior/exterior paints for houses, facilities, transportation equipment or the like and coating layers, adhesive or pressure sensitive adhesive causing to form by the paints; films or members for shielding, for example, electromagnetic waves generated from precision machines, electrical and electronic equipments or various displays; containers or packaging materials for foods, agents, chemicals and cosmetics or the like; sheets or film materials for agricultural and industrial uses; discoloration inhibitors for printed materials, dyed materials, dyes/pigments or the like; protective films for resin members or various devices; glass interlayers; cosmetics; clothing textile products or textile; interior articles for household use such as curtains, carpets and wallpapers; optical lenses such as plastic lenses, contact lenses, medical instruments such as artificial eyes optical pickup lenses, camera lenses and lenticular lenses; optical articles such as optical filters, backlight display films, prisms, mirrors, photograph materials and displays as well as protective films for these optical articles; optical materials; films having a functional optical layer(s) (protective films for various optical disk substrates, reflective films, anti-reflective films, alignment films, polarizing films, polarizing layer protective films, retardation films, light diffusion films, viewing angle improving films, electromagnetic wave shield films, anti-glare films, light shielding films and brightness improving films) and members, adhesives or pressure sensitive adhesive for use thereof; optical molded products such as optical fibers and information recording substrates; surface protection films for solar cells; stationery products; sign boards, indicators or the like as well as surface coating materials thereof; glass substitutes and surface coating materials thereof; glasses and glass coating materials for houses, facilities, transportation equipments or the like; daylight glasses; members for those such as fluorescent lamps, mercury lamps, halogen bulbs. LED lights or the like; coating materials for members for light source and light source protective glasses, window glasses, window films and intermediate films for laminated glasses for houses, facilities, transportation equipments or the like.

The inventive ultraviolet absorber may be suitably used because it causes small discoloration and weight reduction under a long-period heating environment (given temperature for given period of time) when producing or processing the organic or inorganic material that contains the ultraviolet absorber. In order for the inventive ultraviolet absorber to exhibit small discoloration by heat when producing or processing the organic resin composition in combination of the organic resin, it is preferred that the inventive ultraviolet absorber exhibit no discoloration after being heated at 120° C., for 48 hours, preferably 120° C., for 6 hours, more preferably 160° C., for 12 hours, particularly preferably 160° C., for 24 hours. In addition or alternatively, in respect of a rate of change in weight due to the thermal decomposition of the ultraviolet absorber, it is preferred that the rate of loss in weight be lower than 0.03% by weight after being heated at 120° C., for 48 hours, more preferably lower than 0.20% by weight after being heated at 160° C., for 6 hours, even more preferably lower than 0.08% by weight after being heated at 160° C., for 12 hours, particularly preferably lower than 0.04% by weight after being heated at 160° C., for 24 hours. A preferred ultraviolet absorber is the one exhibiting either small discoloration or rate of change in weight, preferably that exhibiting both small discoloration and small rate of change in weight. Examples of the organic resins to be combined with the inventive ultraviolet absorber include, but not particularly limited to, the above-mentioned thermoplastic resin (polymer or copolymer) and thermosetting resin (polymer or copolymer). Among the organic resins, combinations with thermoplastic resins are preferable in that the hot forming and processing are widely used for them. As for the thermoplastic resin, for example, a (meth) acryl-based resin (polymethyl methacrylate resin), ester-based resin (polyethylene terephthalate), polycarbonate-based resin (polycarbonate) and styrene-based resin (polystyrene) are preferably used among the thermoplastic resin polymers. Further, among the copolymers of thermoplastic resins, an acrylonitrile-butadiene-styrene-based copolymer (acrylonitrile-butadiene-styrene copolymer) is preferably used.

These are combined with the inventive ultraviolet absorber to provide an organic resin composition that efficiently and sufficiently absorbs lights having a wavelength in the range of 380 to 400 nm, and suppresses yellowing. In respect of the light resistance, heat resistance and durability of the inventive ultraviolet absorber, as well as the compatibility and affinity to the organic resin, the organic resin composition containing the inventive ultraviolet absorber has a superior appearance, exhibit no discoloration, maintains transparency, suppresses yellowing and causes no bleed-out of the ultraviolet absorber under an environment subjected to heating and/or high-temperature and UV-ray exposure when producing or processing the same.

(Yellowing Suppression in Early Stage and Absorption of Harmful Light at 250 to 420 nm)

The inventive ultraviolet absorber can sufficiently absorb lights in a wavelength region of 250 to 400 nm due to its optical properties. The ultraviolet absorber can also absorb lights in a wavelength region of 400 to 420 nm depending on an additive amount of the same. This ultraviolet absorber has a high ultraviolet absorption effect (molar extinction coefficient) so that the lights in a wavelength region of 250 to 400 nm can be efficiently absorbed even when the ultraviolet absorber is added in a small amount, and exhibits an absorption peak gradient that is larger than that exhibited by a conventional ultraviolet absorber so that yellowing of a member can be suppressed.

Further, in order to obtain a resin member that absorbs harmful lights having a wavelength up to 400 (420) nm which may have negative influence to the human body, for example, a disorder in an ocular tissue; suppresses absorption of light in a wavelength not smaller than 400 (420) nm which constitutes the cause of yellowing in the member; and is superior in appearance by suppressing the yellowing, it is preferable that the absorption peak of light in the chloroform solution of 50 to 100 μM be in the range of 350 to 390 nm, more preferably of 360 to 380 nm, particularly preferably of 360 to 375 nm. It is also preferable that the absorption peaks in these wavelength regions are maximum absorption wavelength ($\lambda_{max}$). Further, it is more preferred that the absorption spectrum on the side of longer wavelength is sharp (having greater tangent in absolute value.) for suppressing absorption of light having a wavelength larger than 400 nm to suppress the yellowing, and it is preferred that the gradient of the absorption peak on the longer wavelength side (or the absolute value of the gradient of the line between the absorption peak and the peak end of the absorption spectrum on the longer wavelength side) for the compounds (1) to (2) and (3) to (4) respectively in the chloroform solutions of 100 μM and 50 μM be not smaller than 0.025, more preferably not smaller than 0.030, even more preferably not smaller than 0.040 and still more preferably not smaller than 0.042. Further, in order to provide an effective absorption with small amount of dose, it is preferred that molar extinction coefficient (or the maximum molar extinction coefficient: $\varepsilon\lambda_{max}$) of the absorption peak at 350 to 390 nm be not smaller than 17,000 L/(mol·cm), more preferably not smaller than 18,000 L/(mol·cm), even more preferably not smaller than 20.000 L/(mol·cm), and still more preferably not smaller than 40,000 L/(mol-cm).

The use of these ultraviolet absorbers allows organic material composition (organic resin composition) and inorganic material composition to suppress the yellowing to provide a good transparent appearance.

(Ultraviolet Absorber for Use in Ultraviolet Shielding Film for Glass or in Composition for Forming the Ultraviolet Shielding Film)

The ultraviolet absorber for the above-mentioned [IV] will be described hereunder. The ultraviolet absorber of [IV] is an ultraviolet absorber for use in an ultraviolet shielding film for glass or in a composition for forming an ultraviolet shielding film for glass, wherein the ultraviolet absorber comprises a 2-phenylbenzotriazole derivative that contains a thioaryl ring group, thiocyclohexyl ring group, thioalkyl group or thioalkylene group as represented by any one of the formulae (1) to (6) shown above.

Examples of the substituent group for $X^{1a}$, Cy, $X^{1c}$, $X^{2c}$, $X^{1d}$, $X^{2d}$ in formulae (1), (2), (3), (4) in the above-mentioned [IV], save for $R^{1a}$, $R^{1b}$, $R^{1c}$, $R^{26}$, $R^{1d}$ and $R^{2d}$, include those represented as substituents for $R^1$ to $R^9$ in the formula (A).

The ultraviolet absorber of [IV] efficiently absorbs harmful lights having a wavelength in the range of 380 to 400 nm and suppresses the absorption of lights having a wavelength of not shorter than 400 nm which constitutes the cause of early-stage yellowing to thereby provide a member having a superior appearance with a minimum impact of such harmful lights, which is superior in either light or heat resistance, or in both light and heat resistances, that is, durability. The absorber particularly provides a glass formed with an ultraviolet shielding film suitable for suppressing transmittance of the lights having a wavelength in the vicinity of 400 nm for a long period of time while suppressing a significant yellow coloring, and also an ultraviolet shielding film suitable for a glass having high visible-light transmittance, as well as a composition and dispersion liquid for ultraviolet shielding film. The ultraviolet absorber of [IV] is excellent in heat resistance and capable of preventing deterioration in ultraviolet shielding effects owing to thermal decomposition when forming the ultraviolet shielding film of the glass and under heat processing for the secondary processing or such, and further under usage environment. From the perspective of heat resistance, the inventive ultraviolet absorber in formulae (1), (3) and (4) preferably has structures:

wherein the 2-phenylbenzotriazole derivative is represented by the formulae (1), (3) or (4) in [II], and $X^{1a}$, $X^{1c}$, $X^{2c}$, $X^{1d}$ and $X^{2d}$ in the formulae (1), (3) and (4) represent residues of phenyl rings;

wherein the 2-phenylbenzotriazole derivative is represented by the formulae (1), (3) and (4) in [II], $X^{1a}$, $X^{1c}$, $X^{2c}$, $X^{1d}$ and $X^{2d}$ in the formulae (1), (3) and (4) represent residues of phenyl rings, each of the l $R^{1a}$s, n $R^{1c}$s, p $R^{2c}$s, r $R^{1d}$s and s $R^{2d}$s independently represents a linear or branched alkyl group having 1 to 18 (preferably 1 to 10) carbon atoms, and l, n, p, r and s each represent an integer of 0 to 3;

wherein the 2-phenylbenzotriazole derivative is represented by the formulae (1), (3) and (4) in [II], $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 1 to 18 (preferably 1 to 10) carbon atoms, and l, n, p, r and s each represent an integer of 1 to 3;

wherein the 2-phenylbenzotriazole derivative is represented by the formulae (1), (3) and (4) in [II], $X^{1a}$, $X^{1c}$, $X^{2c}$, $X^{1d}$ and $X^{2d}$ in the formulae (1), (3) and (4) represent residues of phenyl rings, each of the l $R^{1a}$s, n $R^{1c}$s, p $R^{2c}$s, r $R^{1d}$s and s $R^{2d}$s independently represents a linear or branched alkyl group having 2 to 8 carbon atoms, and l, n, p, r and s each represent an integer of 1 to 3; or wherein the 2-phenylbenzotriazole derivative is represented by the formulae (1), (3) and (4) in [II]; $X^{1a}$, $X^{1c}$, $X^{2c}$, $X^{1d}$ and $X^{2d}$ in the formulae (1), (3) and (4) represent residues of phenyl rings; each of the l $R^{1a}$s, n $R^{1c}$s, p $R^{2c}$s, r $R^{1d}$s and s $R^{2d}$s independently represents a linear or branched alkyl group having 4 to 8 carbon atoms; l, n, p, r and s each represent an integer of 1 to 3.

The inventive ultraviolet absorber is suitable for ultraviolet shielding film, has an optical property to effectively absorb harmful lights having a wavelength in the range of 380 to 400 nm as shown above and to suppress absorption of lights in a wavelength larger than 400 nm which causes an early-stage yellowing, and has a good compatibility to glass. For this reason, the ultraviolet shielding film containing the inventive ultraviolet absorber exhibits a good adherence to a glass, which exhibits high transparency and suppressed yellowing, and can maintain a prolonged ultraviolet shielding effect.

The inventive ultraviolet absorber may be utilized, for example, for the following glass compositions or applications.

As the ultraviolet absorber of [IV] has excellent affinity to glass owing to an affinity of hydroxyl groups present on the glass surface with thioether groups of the inventive ultraviolet absorber via hydrogen bonding, the ultraviolet shielding film has an excellent adherence to a glass to thereby provide a glass containing an ultraviolet shielding film that is excellent in transparency.

When the glass is utilized for an application in which a high refractive index is required, as the inventive ultraviolet absorber has a high refractive index owing to its structural properties, the glass containing the ultraviolet shielding film for which the ultraviolet absorber is utilized can also maintain such refractive index.

The ultraviolet shielding film may form, but not limited to, a part of one side surface of a glass, both side surfaces of a glass, or an intermediate film for laminated glass, or a part of laminated film of glass surface or intermediate film for glass. The examples of materials used for the compositions suitable for forming the ultraviolet shielding film include, but not limited to, an organic material, inorganic material, and organic/inorganic material. The ultraviolet shielding film is not particularly limited in its form but may, for example, be in the form of a coating layer, a covered layer, a film stack, a film, a sheet, a plate or a molded article (which are preferably a coating layer or a film), which may have adhesive or pressure sensitive adhesive layer(s) or have an sticky or adherence property. Examples of the materials of the ultraviolet shielding film include, but not particularly limited to, a resin, pater, fiber, glass, metal, mineral and the like. In the case of resin or glass, the materials may be of crystal, amorphous form or liquid crystal, which is suitable for a glass ultraviolet shielding film.

The ultraviolet absorber of [IV] may include the following ultraviolet absorber a or b <Ultraviolet Absorber a>

Ultraviolet absorber as outlined in either one of the following items (1) or (2):

(1) An ultraviolet absorber to be used for an ultraviolet shielding film for inorganic material composition such as glass in which the material of the ultraviolet shielding film includes, but not particularly limited to, for example, a siliceous material by a sol-gel method which is an ingredient of glass containing silicon oxide, glass, liquid glass, low-melting glass, quartz, silicone resin, alkoxysilane, and silane coupling agent, said ultraviolet absorber being for the above-mentioned [IV] and the ultraviolet shielding film. An example of the ultraviolet shielding film includes the one in which the ultraviolet shielding film is a coating film formed on a glass wherein the coating film is glassy and contains silicon oxide as a main component and the ultraviolet absorber for the above-mentioned [IV].

(2) An ultraviolet absorber to be used for a composition to form the ultraviolet shielding film, wherein said composition for forming the ultraviolet shielding film includes: ingredients used for materials of the ultraviolet shielding film including, but not particularly limited to, a silicon oxide precursor which is an ingredient of glass containing silicon oxide, alkoxysilane, silane coupling agent and the like; and the ultraviolet absorber for the above-mentioned [IV]. The ultraviolet absorber used for a composition to form the ultraviolet shielding film is not limited to any specific form and may be used by adding the same to a solvent, or alternatively by dispersing the ultraviolet absorber of powdery, granular or fine particulate form therein.

In the case of coating films or layers of glass containing silicon oxide as a main component in which the ultraviolet absorber is dispersed to utilize the same, it is preferred that the average particle size of the ultraviolet absorber fine particles be not larger than 150 nm, more preferably in a rage of 10 to 150 nm, even more preferably of 50 to 140 nm, still more preferably of 70 to 140 nm in respect of transparency and ultraviolet shielding effects. Particles having an average particle size which is too large may cause a decreased film transparency while too small diameter may deteriorate ultraviolet absorption capability or decrease its sustainability.

An example of the composition for forming the ultraviolet shielding film include the one containing a silicon oxide precursor and the ultraviolet absorber for the above-mentioned [IV], wherein the ultraviolet absorber for the above-mentioned [IV] is in a form of fine particle having an average particle size not larger than 150 nm.

<Ultraviolet Absorber b>
(1) An ultraviolet absorber to be used for an ultraviolet shielding film for glass, said ultraviolet absorber being used for the ultraviolet shielding film which is formed from an organic material composition that contains the ultraviolet absorber for the above-mentioned [IV].
(2) An ultraviolet absorber to be used for an ultraviolet shielding film for glass, said ultraviolet absorber being used for an organic material composition that contains the ultraviolet absorber for the above-mentioned [IV].

As the inventive ultraviolet absorber and the organic material composition has a high heat resistance, it is preferably used for a resin having a thermoforming or thermosetting temperature of not smaller than 80° C., more preferably of not smaller than 120° C., particularly preferably of not smaller than 160° C., or it is preferably produced and used at these temperatures.

In the above ultraviolet absorber a and b, the composition of (2) may contain, but not particularly limited to, additives such as antioxidizing agents, heat stabilizers, weather stabilizers, light stabilizers, pigments, dyes, fillers, plasticizers, antistatic agents, nucleating agents, wetting agents, preservatives, fungicides, antifoaming agents, stabilizing agents, antioxidants, and chelating agents, and solvents such as water or an organic solvent or the like as optional ingredients.

The organic material composition herein is a composition as discussed above. The organic material composition is preferably an organic resin composition containing an organic resin and the ultraviolet absorber for the above-mentioned [IV].

In the ultraviolet absorber of [IV], the above descriptions of [I] to [III] will be referred regarding the formulae (1), (3) and (4). As for the formula (2), the above descriptions of [I] will be referred thereto.

In the case where the formula (3) contains a thioalkylene group, $A^{1c}$ is a phenyl ring residue, a naphthyl ring residue or a linear or branched alkylene group that has 1 to 22 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom. Although not particularly limited, the alkylene groups includes a methylene group, 1,1-dimethyl-methylene group, ethane-1,2-diyl group, propane-1,3-diyl group, propane-2,2-diyl group, 1-methylethane-1,2-diyl group, butane-1,4-diyl group, butane-1,3-diyl group, 2-methylpropane-1,3-diyl group, pentane-1,5-diyl group, pentane-1,4-diyl group, hexane-1,6-diyl group, heptane-1,7-diyl group, octane-1,8-diyl group, nonane-1,9-diyl group, decane-1,10-diyl group, undecane-1,11-diyl group, dodecane-1,12-diyl group, tridecane-1,13-diyl group, tetradecane-1,14-diyl group, pentadecane-1,15-diyl group, hexadecane-1,16-diyl group, heptadecane-1,17-diyl group, octadecane-1,18-diyl group, nonadecane-1,19-diyl group, eicosane-1,20-diyl group, heneicosane-1,21-diyl group, and docosane-1,22-diyl group. Among these examples, linear or branched alkylene groups are preferred, and linear alkylene groups are more preferred.

In the case where the alkylene group has hydrogen atoms substituted by, at least one of two ends thereof interrupted by, or carbon-carbon bonds interrupted by a monovalent or divalent group(s), the number of said monovalent or divalent group may be, although not particularly limited to, for example, not larger than two, or alternatively not larger than one.

Specific examples of the aromatic group, unsaturated group, nitrogen-containing group, sulfur-containing group, oxygen-containing group, phosphorus-containing group, alicyclic group and halogen atom as the monovalent or divalent groups include those similar to the monovalent or divalent groups listed as the substituent groups of $R^1$ to $R^9$ in the 2-phenylbenzotriazole skeleton represented by the formula (A) to which the descriptions thereof are referred.

In the formula (5), the $Y^{1e}$ in the thioalkyl group (—S—$Y^{1e}$) represents a linear or branched alkyl group that has 1 to 22 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom. Examples of these alkyl groups include, but not particularly limited to, a methyl group, ethane-1-yl group, propane-1-yl group, 1-methylethane-1-yl group, butane-1-yl group, butane-2-yl group, 2-methylpropane-1-yl group, 2-methylpropan-2-yl group, pentan-1-yl group, pentan-2-yl group, hexane-1-yl group, heptane-1-yl group, octane-1-yl group, 1,1,3,3-tetramethylbutane-1-yl group, nonan-1-yl group, decane-1-yl group, undecane-1-yl group, dodecane-1-yl group, tridecane-1-yl group, tetradecane-1-yl group, pentadecane-1-yl group, hexadecane-1-yl group, heptadecane-1-yl group, octadecane-1-yl group, nonadecan-1,19-diyl group, eicosan-1,20-diyl group, heneikosan-1,21-diyl group, docosan-1,22-diyl group, and benzyl group. Among these examples, preferred is a benzyl group or a linear or branched alkyl group having 1 to 18 carbon atoms, more preferably 1 to 10 carbon atoms.

In the formula (6), the $Y^{1f}$ and $Y^{2f}$ in the thioalkyl groups (—S—$Y^{1f}$, —S—$Y^{2f}$) independently represent a linear or branched alkyl group that has 1 to 22 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom. Examples of these alkyl groups include, but not particularly limited to, a methyl group, ethane-1-yl group, propane-1-yl group, 1-methyl-ethane-1-yl group, butane-1-yl group, butane-2-yl group, 2-methylpropane-1-yl group, 2-methylpropan-2-yl group, pentan-1-yl group, pentan-2-yl group, hexane-1-yl group, heptane-1-yl group, octane-1-yl group, 1,1,3,3-tetramethylbutane-1-yl group, nonan-1-yl group, decane-1-yl group, undecane-1-yl group, dodecane-1-yl group, tridecane-1-yl group, tetradecane-1-yl group, pentadecane-1-yl group, hexadecane-1-yl group, heptadecane-1-yl group, octadecane-1-yl group, nonadecan-1,19-diyl group, eicosan-1,20-diyl group, heneikosan-1,21-diyl group, and docosan-1,22-diyl group. Among these examples, preferred is a linear or branched alkylene group, more preferably a linear alkylene group. The number of carbon atoms of them are preferably 1 to 18, more preferably 1 to 10.

If the alkyl group is such a group with hydrogen atoms therein substituted by, or at least one of two ends thereof interrupted by, or carbon-carbon bonds therein interrupted by the monovalent or divalent group(s), although there are no particular limitations on the number of the monovalent or divalent groups, the number of such groups may, for example, be not larger than two, or not larger than one.

Specific examples of the aromatic group, unsaturated group, nitrogen-containing group, sulfur-containing group, oxygen-containing group, phosphorus-containing group, alicyclic group and halogen atom as the monovalent or divalent groups include those similar to the monovalent or divalent groups listed as the substituent groups of $R^1$ to $R^9$ in the 2-phenylbenzotriazole skeleton represented by the formula (A) to which the descriptions thereof are referred.

As for the combination of $R^6$, $R^7$, $R^8$ and $R^9$ in formulae (1) to (6) in [IV], the items as set forth in a-1 to a-7 are preferably referred to: as for the combination of $R^1$, $R^2$, $R^3$, $R^4$, $R^5$ in formulae (1) to (6) in [IV], the items as set forth in i-1 to i-28 are preferably refereed to; As for the combination of m $R^{1b}$s in formula (2), the items e-1 to e-15 are preferably refereed to; as for the n $R^{1c}$s and $X^{1c}$, p $R^{2c}$s and $X^{2c}$, and q $A^{2c}$s in formula (3), items o-1 to o-17 are preferably refereed to.

Preferable examples of combinations of l $R^{1a}$s and $X^{1a}$, r $R^{1d}$s and $X^{1d}$ as well as s $R^{2d}$s and $X^{2d}$ in each formula (1), (4) in [IV] are as follows:

u'-1: $X^{1a}$, $X^{1d}$ and $X^{2d}$ are residues of phenyl rings.

u'-2: in u'-1, l, r, s=0; substituent groups $R^{1a}$, $R^{1d}$ and $R^{2d}$ are not present at $X^{1a}$, $X^{1d}$ and $X^{2d}$, moieties of $X^{1a}$, $X^{1d}$ and $X^{2d}$ that are substitutable by $R^{1a}$, $R^{1d}$ and $R^{2d}$ are all hydrogen atoms.

u'-3: in u'-1, each of the l $R^{1a}$s, r $R^{1d}$s and s $R^{2d}$s independently represents a hydrocarbon group having 1 to 18 carbon atoms; this hydrocarbon group is a hydrocarbon group having 1 to 18 carbon atoms, preferably a linear or branched alkyl group having 1 to 18 carbon atoms; l, r, s=1 to 5.

u'-4: in u'-3, l, r, s=1 to 3.

u'-5: in u-4, at least one of $R^{1a}$, $R^{1d}$ and $R^{2d}$ independently represents a branched alkyl group having 3 to 8 carbon atoms.

u'-6: in u'-4, l, r, s=1; each of $R^{1a}$, $R^{1d}$ and $R^{2d}$ independently represents a linear or branched alkyl group having 1 to 18 (preferably 1 to 10) carbon atoms.

u'-7: in u'-6, l, r, s=1; each of $R^{1a}$, $R^{1d}$ and $R^{2d}$ independently represents a linear or branched alkyl group having 1 to 10 carbon atoms; this alkyl group preferably has 1 to 8, more preferably 2 to 8, even more preferably 3 to 8 carbon atoms.

u'-8: in any one of u'-3 to u'-7, with respect to PhBzT$^{1a}$-S—, PhBzT$^{1d}$-S— and PhBzT$^{2d}$-S—, at least one of $R^{1a}$, $R^{1d}$ and $R^{2d}$ is in the para position.

u'-9: in u'-4, l, r, s=2; each of $R^{1a}$, $R^{1d}$ and $R^{2d}$ independently represents a linear or branched alkyl group having 1 to 18 (preferably 1 to 10) carbon atoms.

u'-10: in u'-9, l, r, s=2; each of $R^{1a}$, $R^{1d}$ and $R^{2d}$ independently represents a linear or branched alkyl group having 1 to 10 carbon atoms; each of these alkyl groups preferably has 1 to 5, more preferably 1 to 4, even more preferably 1 carbon atom(s); and/or a total number of the carbon atoms in these alkyl groups is preferably 2 to 12, more preferably 2 to 10, even more preferably 2 to 5, particularly preferably 2.

u'-11: in any one of u'-9 and u'-10, with respect to PhBzT$^{1a}$-S—, PhBzT$^{1d}$-S— and PhBzT$^{2d}$-S—$R^{1a}$, $R^{1d}$ and $R^{2d}$, when l, r, s=2, are each in the ortho, para positions or the ortho, meta positions.

u'-12: in any one of u'-3 to u'-11, each of $R^{1a}$, $R^{1d}$ and $R^{2d}$ independently represents a tertiary and/or quaternary carbon-containing hydrocarbon group, preferably an alkyl group.

u'-13: in u'-1, each of the l $R^{1a}$s, r $R^{1d}$s and s $R^{2d}$s independently represents an alkoxy group possessing a linear or branched alkyl group having 1 to 18 carbon atoms, preferably an alkoxy group possessing a linear alkyl group having 1 to 8 carbon atoms, more preferably an alkoxy group possessing a linear alkyl group having 1 to 4 carbon atoms; preferably l, r, s=1 to 3, more preferably l, r, s=1 to 2, particularly preferably l, r, s=1.

u'-14: in u'-13, l, r, s=1, the alkoxy group is in the meta position with respect to PhBzT$^{1a}$-S—, PhBzT$^{1d}$-S— and PhBzT$^{2d}$-S—.

u'-15: in u'-1, the l $R^{1a}$s, r $R^{1d}$s and s $R^{2d}$s are hydroxy groups; preferably l, r, s=1 to 3, more preferably l, r, s=1 to 2, particularly preferably l, r, s=1.

u'-16: in u'-15, l, r, s=1, the hydroxy group(s) is in the para position with respect to PhBzT$^{1a}$. S—, PhBzT$^{1d}$-S— and PhBzT$^{2d}$-S—.

u'-17: $X^{1a}$, $X^{1d}$ and $X^{2d}$ are residues of naphthyl rings; preferably l, r, s=0

Preferable embodiments of the ultraviolet absorber in [IV] are further shown below:

ka-1: The ultraviolet absorber in [IV]

ka-2: in ka-1, the 2-phenylbenzotriazole derivative is represented by any one of the above formulae (1) to (4); $X^{1a}$, $X^{1c}$, $X^{2c}$, $X^{1d}$ and $X^{2d}$ in the formulae (1), (3) and (4) represent residues of phenyl rings; each of the l $R^{1a}$s, m $R^{1b}$s, n $R^{1c}$s, p $R^{2c}$s, r $R^{1d}$s and s $R^{2d}$s independently represents a linear or branched alkyl group having 1 to 18 carbon atoms; 1, m, n, p, r and s each represent an integer of 0 to 5.

ka-3: in ka-1 and ka-2, the 2-phenylbenzotriazole derivative is represented by any one of the above formulae (1) to (4); $X^{1a}$, $X^{1c}$, $X^{2c}$, $X^{1d}$ and $X^{2d}$ represent residues of phenyl rings, and the thioaryl or thiocyclohexyl ring group is bonded to the phenyl moiety of the benzotriazole skeleton in the formulae (1), (3), and (4).

ka-4: in ka-2 and ka-3, the 2-phenylbenzotriazole derivative is represented by any one of the above formulae (1), (3) and (4); $X^{1a}$, $X^{1c}$, $X^{2c}$, $X^{1d}$ and $X^{2d}$ in the formulae (1), (3) and (4) represent residues of phenyl rings; at least one of the 1 $R^{1a}$s, n $R^{1c}$s, p $R^{2c}$s, r $R^{1d}$s and s $R^{2d}$s independently represents a linear or branched alkyl group having 3 to 8 carbon atoms; l, n, p, r and s each represent an integer of 1 or 2.

ka-5: in ka-2 to ka-4, the 2-phenylbenzotriazole derivative is represented by any one of the above formulae (1), (3) and (4); $X^{1a}$, $X^{1c}$, $X^{2c}$, $X^{1d}$ and $X^{2d}$ in the formulae (1), (3) and (4) represent residues of phenyl rings; at least one of the 1 $R^{1a}$s, n $R^{1c}$s, p $R^{2c}$s, r $R^{1d}$s and s $R^{2d}$s independently represents a tertiary and/or quaternary carbon-containing alkyl group; l, n, p, r and s each represent an integer of 1 or 2.

ka-6: in ka-1, the 2-phenylbenzotriazole derivative is represented by any one of the above formulae (1), (3) and (4); $X^{1a}$, $X^{1c}$, $X^{2c}$, $X^{1d}$ and $X^{2d}$ in the formulae (1), (3) and (4) represent residues of phenyl rings; each of 1 $R^{1a}$s, n $R^{1c}$s, p $R^{2c}$s, r $R^{1d}$s and s $R^{2d}$s independently represents an alkoxy group possessing a linear or branched alkyl group having 1 to 18 carbon atoms, a hydroxy group or a halogen atom; l, n, p, r and s each represent an integer of 1 or 2.

ka-7: in ka-2 to ka-6, the 2-phenylbenzotriazole derivative is represented by any one of the formulae (1), (3) and (4); and a hydroxy group and a methyl group are present in a phenyl skeleton of the 2-phenylbenzotriazole skeleton in the formulae (1), (3) and (4).

ka-8: in ka-7, the 2-phenylbenzotriazole derivative is represented by any one of the formulae (1), (3) and (4); a thioaryl ring group is present at a phenyl moiety of a benzotriazole skeleton in the 2-phenylbenzotriazole skeleton, and a hydroxy group, a tert-butyl group and a methyl group are present at a position-2 phenyl skeleton Ph.

ka-9; in ka-1, the 2-phenylbenzotriazole derivative is represented by the formula (6); each of $Y^{1f}$ and $Y^{2f}$ independently represents a hydrocarbon group having 1 to 18 carbon atoms, an alkoxy group having 1 to 18 carbon atoms or a linear or branched alkyl group that has 1 to 22 carbon atoms and may have hydrogen atoms therein substituted by a hydroxy group.

<Ultraviolet Absorber a>

The ultraviolet absorber a in the ultraviolet absorber of [IV] will be described hereunder with reference to an example for use in a glass with a glassy coating film for a transportation equipment (including a vehicle).

A glass having the ultraviolet absorber a comprises a glass and an ultraviolet shielding film formed on the surface thereof. The ultraviolet shielding film contains silicon oxide and the ultraviolet absorber a. It is preferable that the ultraviolet shielding film contains a silicon oxide as a main component.

The ultraviolet shielding film may be of any material but preferably is glassy. The film herein is referred as to glassy when the matrix component of the film is of glass, as well as in a case where the film contains a crystalline component of, for example, an organic compound A, an organic compound B to be described later and ITO fine particles. The term "main component" as used herein refers to a component that made up of not smaller than 50%, preferably not smaller than 60% by weight thereof. Silicon oxide is a component that provides the film durability and hardness as required from the standpoint of practicality. The ultraviolet absorber a functions as an ultraviolet shielding component.

The ultraviolet shielding film may contain components other than silicon oxide and the ultraviolet absorber a. Examples of the optional component of the film include, but not limited to, an organic component B that is described later and is not fall under the category of the ultraviolet absorber a, and an organic component C which is a hydrophilic organic compound. The organic component C may be a polymer. The ultraviolet shielding film may contain a further component such as a structural unit that originates from a silane coupling agent. The structural unit that originates from a silane coupling agent is referred to as a silane coupling agent derivative that is produced when the silane coupling agent is reacted with the other organic and/or inorganic component.

The size or form of the ultraviolet absorber a to be added thereto is not particularly limited but the absorber is added as fine particles in order to enhance light transmission properties of the glass containing the ultraviolet shielding film. Addition of the absorber as fine particles enhances a sustainability of the ultraviolet shielding effects as compared to the case where the absorber is added as a solute. The average particle size of the fine particles is regulated to be not larger than 150 μm to suppress the haze value of film. An organic compound that is solid at room temperature is suitable as the ultraviolet absorber a. The term "room temperature" as used herein refers to 25° C.

As the organic compound that is solid at room temperature, there is known a polymer that is obtained by polymerizing an ultraviolet absorber. However, because such ultraviolet shielding component is produced by polymerizing an ultraviolet absorber that is introduced with a polymerizable group such as (meth)acrylic group, the ultraviolet shielding effects thereof per unit weight is inferior to a low molecular ultraviolet absorber.

The molecular weight of the organic compound A is preferably not larger than 5000, more preferably not larger than 3000, even preferably not larger than 2000, particularly preferably not larger than 1500, and depending on the cases, it may be not larger than 1300, particularly not larger than 1200, particularly not larger than 900, more particularly not larger than 800. The molecular weight of the organic compound A is preferably not smaller than 200, more preferably not smaller than 300. Preferably, the organic compound A does not contain any polymerizable carbon-carbon double bond. Such polymerizable carbon-carbon double bond includes a double bond contained in a polymerizable functional group such as a vinyl group, vinylene group and vinylidene group.

As for the examples as described above, the ultraviolet absorber a is preferably in a crystalline state in the composition for forming ultraviolet shielding film or the ultraviolet shielding film. Whether the ultraviolet absorber a in the film is in a crystalline state can be confirmed by X-ray diffraction. The ultraviolet absorber a may be pulverized using a commonly-known dry or wet pulverizer before being compounded in the composition for forming ultraviolet shielding film to be a predetermined average particle size. The time taken for the ultraviolet absorber a to be pulverized into particles having a predetermined average particle size depends on the type of the pulverizer, the amount of the ultraviolet absorber a put into the pulverizer, and pulverization conditions such as rotational speed. Accordingly, as for mass production, it is desirable that the time taken to achieve the predetermined average particle size be determined in advance by repeating the steps of, stopping pulverization with a pulverizer in an appropriate timing, and measuring the average particle sizeof the sample of the pulverized material. At the time of pulverization, a surfactant, a water-soluble resin, or the like, may be added as appropriate to the ultraviolet absorber a to be pulverized. It is desirable that the ultraviolet absorber a be dispersed in the film in the form of fine particles having an average particle size of 150 nm or less, preferably 10 nm to 150 nm, more preferably 50 nm to 140 nm, particularly preferably 70 nm to 140 nm. A too large average particle size of the fine particles results in decreasing the transparency of the film, whereas a too small average particle size may lead to deterioration in the ultraviolet absorption capability or to reduction in the sustainability of the ultraviolet absorption capability. The value of the "average particle size" is a numerical value based on measurement using a dynamic light scattering method which is a type of photon correlation method. The same applies to measurement values in the description of Examples given below. Specifically, the "average particle size" means a particle size that corresponds to a cumulative frequency of 50% in the distribution of equivalent spherical diameters based on the particle volumes. For example, the "average particle size" can be measured using "Microtrac Ultrafine Particle Analyzer 9340-UPA 150" manufactured by Nikkiso Co., Ltd. The presence of the fine particles of the ultraviolet absorber a dispersed in the film can be confirmed by observation using a scanning electron microscope (SEM) or a transmission electron microscope (TEM). An average value A of the top 10% of the respective maximum lengths of the fine particles present in a cross-section of the film observed with a SEM or a TEM is not below the value of the "average particle size" defined as above. Accordingly, when the average value A is 150 nm or less, the "average particle size" can be determined to be 150 nm or less. In addition, for the fine particles present in the cross-section of the film, an average value B of the bottom 10% of the lengths of the fine particles in directions orthogonal to directions along which the respective maximum lengths are defined, is not above the value of the "average particle size" defined as above. Accordingly, when the average value B is, for example, 50 nm or more, the "average particle size" can be determined to be 50 nm or more. The ultraviolet absorber a can be introduced into the film in the form of a solute dissolved in an organic solvent capable of dissolving the ultraviolet absorber a. Introduction of the absorber in form of a solute is a method that can be readily be implemented and also is desired for achieving more uniform distribution of the ultraviolet absorber a in the ultraviolet shielding film. However, by introducing the ultraviolet absorber a into the film in the form of fine particles, the sustainability of the ultraviolet shielding ability of the film is improved. In addition, it has been found that more preferable spectral absorption characteristics can be obtained by adding the ultraviolet absorber a in the form of fine particles than by adding the ultraviolet absorber a in the form of a solute. The absorption peak of the ultraviolet absorber a in a spectral absorbance curve can be shifted to a longer wavelength when the ultraviolet absorber a is added in the form of fine particles compared to a case where the ultraviolet absorber a is added as a solute. By taking advantage of this shift, it is possible to effectively shield against the light having a wavelength in the vicinity of 400 nm. However, as the absorption peak shifts toward the long-wavelength side, the ultraviolet shielding film shall be more significantly colored with a yellowish color; by taking such phenomenon into consideration, the organic compound A is suitable for sufficiently reducing the transmittance of a light near the wavelength of 400 nm while restricting the ultraviolet shielding film from being significantly colored with a yellowish color. The composition for forming an ultraviolet shielding film may be a film-forming solution containing a silicon oxide precursor and the ultraviolet absorber a. While there are no particular restrictions on a solvent composing the film-forming solution, and examples thereof may include water and organic solvents, water and lower alcohols are suitable, and water is the most suitable, in terms of dispersing the ultraviolet absorber in the form of fine particles as is the case with the above example. As lower alcohols, preferred are alcohols having 1 to 3 carbon atoms, such as methanol, ethanol and isopropanol. The composition for forming an ultraviolet shielding film may also contain components that can be added to an ultraviolet shielding film, such as the organic compound B and a silane coupling agent. If necessary, the composition for forming an ultraviolet shielding film may contain additives such as an antioxidant, a heat resistant stabilizer, a weather resistant stabilizer, a light stabilizer, a colorant, a dye, a filler, a plasticizer, an antistatic agent, a nucleating agent, a moisturizer, a preservative, an antifungal agent, an antifoaming agent and a stabilizer. There are no restrictions on the type of the silicon oxide precursor as long as it is capable of supplying silicon oxide to the ultraviolet shielding film. If forming an ultraviolet shielding film by a later-described sol-gel method, a preferable silicon oxide precursor shall be a hydrolyzable functional group-containing silicon compound, a typical example of which being silicon tetraalkoxide. Here, silicon oxide is also supplied from the silicon atoms contained in a silane coupling agent. Therefore, a silane coupling agent also serves as a silicon oxide precursor The silicon oxide in the ultraviolet shielding film may occupy the entire film by not less than 40% by mass, not less than 50% by mass (silicon oxide is the main component of the film in such case), or not less than 70% by mass in certain cases. Preferably, the ultraviolet shielding film has such a mode that the main component thereof is silicon oxide, and that the fine particles of the organic compound A and other components are dispersed in the network of the Si—O bonds. A film having such mode is suitable for outdoor use such as window glasses. It is preferred that the composition for forming an ultraviolet shielding film contain the silicon oxide precursor in a way such that the content ratio of the silicon oxide in the ultraviolet shielding film formed from the composition shall approximately fall into the above ranges. It is preferred that the ultraviolet absorber a be contained in an amount of 0.01 to 90%, more preferably 0.1 to 80%, even more preferably 1 to 80%, particularly preferably 5 to 60%, more particularly preferably 5 to 50%, even more particularly preferably 7 to 30%, in terms of % by mass with respect to the silicon oxide in the ultraviolet shielding film. In view of this, though not particularly limited, the ultraviolet absorber a shall preferably be added in an amount of, for example, 0.5 to 25%, more preferably 0.5 to 15%, also in terms of % by mass with respect to the amount of the film-forming solution. The organic compound B is an ultraviolet shielding component other than the ultraviolet absorber a. Although not particularly limited, examples of the organic compound B include ultraviolet absorbers containing benzotriazole, triazine, benzophenone or benzoate skeletons. Although not particularly limited, there may be listed, for example, an organic compound having a molecular structure where a 2-phenyl-benzotriazole skeleton is present, and where no sulfur atom-containing group is joined to the 2-phenyl-benzotriazole skeleton; and a benzophenone compound. As is the case with the ultraviolet absorber a, it is preferred that the organic compound B maintain a crystallized state in the composition for forming an ultraviolet shielding film and in the ultraviolet shielding film. Before being added to the composition for forming an ultraviolet shielding film, the organic compound B may be pulverized using a known dry-type or wet-type pulverizer so that a given average particle size will be achieved. A preferable average particle size of the organic compound B is defined as above in the description of the ultraviolet absorber a. It is preferred that the organic compound B be added in such an amount that a ratio of a total amount of the organic compound B and the ultraviolet absorber a will be the aforementioned ratio of the ultraviolet absorber a with respect to the silicon oxide in the ultraviolet shielding film. The organic compound B may be added in an amount smaller than the amount of the ultraviolet absorber a by mass, preferably smaller than 50% of the amount of the ultraviolet absorber a by mass.

The organic compound B may have two or more 2-phenylbenzotriazole skeletons. It is preferred that the two or more 2-phenylbenzotriazole skeletons be joined together by alkylene groups. One preferable example of an organic compound B having two 2-phenylbenzotriazole skeletons has a form where the two skeletons are bonded to each other via methylene groups that are bonded to $R^2$s in both skeletons. In this form, in each skeleton, $R^1$ may be a hydroxy group, $R^4$ may be a tert-butyl group, $R^3$ and $R^5$ may be hydrogen atoms. For example, there may be listed 2,2'-methylenebis [6-(benzotriazole-2-yl)-4-tert-octylphenol].

Another example of the organic compound B is a benzophenone compound. For example, there may be listed 2,2, 4,4-tetrahydroxy benzophenone, 2,4-dihydroxybenzophenone, 2-hydroxy-4-methoxy benzophenone, 2-hydroxy-4-octoxybenzophenone and 5,5'-methylenebis(2-hydroxy-4-methoxybenzophenone).

An organic compound C is a hydrophilic organic compound, and may be a polymer. The organic compound C is a component contributing to an improvement in dispersibility of the ultraviolet absorber a and the benzotriazole-based ultraviolet shielding component in the organic component B in the ultraviolet shielding film, improving the light ray shielding capability of the benzotriazole-based ultraviolet shielding component, and even suppressing the deterioration of this component. When forming an ultraviolet shielding film with a relatively large thickness (e g, a thickness of greater than 300 nm, or even a thickness of not smaller than 500 nm) by a liquid phase film-forming method such as a sol-gel method, cracks may occur as the liquid component contained in the film-forming solution evaporates. The organic compound C is also a component enabling the formation of a thick film while suppressing the occurrence of cracks. Preferably, the organic compound C is at least one selected from a polyether compound, a polyol compound, polyvinyl pyrrolidones and polyvinyl caprolactams. A polyether compound is a compound having two or more ether bonds. A polyol compound is a compound having two or more hydroxy groups. Polyvinyl pyrrolidones are polymers containing, as monomers, vinylpyrrolidone and a derivative thereof. Polyvinyl caprolactams are polymers containing, as monomers, vinylcaprolactam and a derivative thereof. Examples of the organic compound C include a polyether-type surfactant and a polyol compound generated by a reaction of epoxy groups in a polyepoxy compound. The organic compound C may also be a polymer. Examples of the organic compound C include polycaprolactone polyol, bisphenol A polyol, polyethylene glycol and polypropylene glycol. It is preferred that the organic compound C be added to the film by an amount of 0 to 75%, more preferably 0.05 to 50%, particularly preferably 0.1 to 40%, more particularly preferably 1 to 30%, not larger than 10% in certain cases, and not larger than 7% if necessary, in terms of % by mass with respect to the silicon oxide in the film. While there are no particular restrictions on the type of a silane coupling agent, an organic compound represented by $LSiM_3$ is preferred. Here, L is at least one selected from a vinyl group, a glycidoxy group, a methacryl group, an amino group and a mercapto group; M is a halogen element or an alkoxy group. A silane coupling agent is such that the L groups react with the organic components in the ultraviolet shielding film, and the X groups undergo hydrolyzation and react with the inorganic components in the film. Due to this reaction, a silane coupling agent brings about an effect of contributing to the improvement in dispersibility of the ultraviolet shielding component(s) which are the organic compound A or the organic compounds A and B in the film, and enabling the formation of a thick film while suppressing the occurrence of cracks. It is preferred that a silane coupling agent be added to the film in a way such that the silicon oxide supplied from the silane coupling agent will be in an amount of 0) to 30%, more preferably 0.1 to 20%, even more preferably 1 to 10%, in terms of mol % with respect to all the silicon oxides in the ultraviolet shielding film. Here, the silicon oxide supplied from the silane coupling agent is calculated in accordance with the number of the oxygen atoms bonded to the silicon atoms in the structural units derived from the silane coupling agent in the ultraviolet shielding film. For example, the silicon oxide supplied from the aforementioned silane coupling agent represented by $LSiM_3$ is expressed as $SiO_{1.5}$, since the silicon atom is bonded to three oxygen atoms. As another component that may be contained in the ultraviolet shielding film, there may be listed indium tin oxide (ITO) fine particles. ITO fine particles are a preferable component for near-infrared absorption. ITO fine particles may be dispersed in the film as fine particles having an average particle size of not larger than 200 nm, preferably 5 to 150 nm. As is the case with the fine particles of the ultraviolet absorber a, the transparency of the film will be impaired if the particle size thereof is excessively large, and an effect(s) by addition cannot be achieved in a sufficient manner if the particle size thereof is excessively small. A dispersion liquid of ITO fine particles may be prepared in advance as well, and then added to the film-forming solution. The ultraviolet shielding film may contain inorganic components other than silicon oxide and ITO fine particles. As such inorganic component, there may be listed a component derived from an acid catalyst used in a sol-gel method. The silicon oxide in the ultraviolet shielding film may occupy the entire film by not less than 30% by mass, preferably not less than 40% by mass, more preferably not less than 50% by mass (silicon oxide is the main component of the film in such case), or even not less than 70% by mass in certain cases. Preferably, the ultraviolet shielding film has such a mode that the main component thereof is silicon oxide, and that the fine particles of the ultraviolet absorber a and other components are dispersed in the network of the Si—O bonds. There are no particular restrictions on the type of glass having a film of such mode, examples of which may include glasses used in buildings and transportation equipments, specifically glasses used in vehicles such as automobiles and railway vehicles, ships and aircrafts etc., daylight glasses, and glasses used in fluorescent lights, mercury lamps, halogen light bulbs and LED lights etc. A glass having the film of the abovementioned mode is particularly suitable for outdoor use such as the use as a window glass.

Described hereunder is a preferable method for forming the ultraviolet shielding film of the above example by a sol-gel method. As an organic solvent used in a sol-gel method, a solvent having a high compatibility with silicon alkoxide and water is preferred; a lower alcohol having 1 to 3 carbon atoms is suitable. Examples of the silicon alkoxide as a silicon oxide precursor include silicon tetraalkoxides such as silicon tetramethoxide, silicon tetraethoxide (TEOS) and silicon tetraisopropoxide. A hydrolysate of the silicon alkoxide may also be used as a silicon oxide precursor. The concentration of the silicon alkoxide in a forming solution used in a sol-gel method is 3 to 15% by mass, particularly preferably 3 to 13% by mass, in terms of a silicon oxide concentration after converting the silicon alkoxide into silicon oxide. When this concentration is excessively high, cracks may occur in the film. With respect to the silicon alkoxide, and in terms of molar ratio, water is preferably in an amount of 4 times as large as the amount of the silicon alkoxide or even larger, specifically 4 to 40 times, preferably 4 to 35 times larger than the amount of the silicon alkoxide. As a hydrolysis catalyst, preferred is an acid catalyst, particularly a strong acid such as hydrochloric acid, nitric acid, sulfuric acid, trichloroacetic acid, trifluoroacetic acid, methanesulfonic acid or paratoluenesulfonic acid. Since an organic matter(s) derived from an acid catalyst may impair the hardness of the film, an inorganic acid is preferred as an acid catalyst. Hydrochloric acid is the most preferable acid catalyst because it has a high volatility and thus does not remain in the film easily. It is preferred that the concentration of the acid catalyst be in a range of 0.001 to 2 mol/kg in terms of molality of protons on the assumption that the protons have completely dissociated from the acid. By excessively adding water to the above extent, and by adding the acid catalyst in a way such that the above level of concentration will be achieved, a relatively thick film can be easily formed by a sol-gel method in a temperature range where the decomposition of an organic matter(s) can be prevented. By mixing the solution that contains the abovementioned components and is applicable in a sol-gel method with a dispersion liquid in which fine particles of the ultraviolet absorber a or the like are dispersed, and then, if necessary, by adding the organic compound C or the like, a film-forming solution of an ultraviolet shielding film will be able to be prepared. However, the method for preparing the film-forming solution shall not be limited to this method, the components required for film formation in a sol-gel method may be sequentially added to the dispersion liquid of the fine particles. The film-forming solution may also be prepared in a way such that the solution will contain, together with the fine particles of the ultraviolet absorber a or the like, components required for film formation in a method other than a sol-gel method, such as polysilazane. In a step of applying the film-forming solution, it is preferred that a relative humidity in an atmosphere be lower than 40%, more preferably be maintained at 30% or lower. By maintaining the relative humidity at a lower level, the film can be prevented from excessively absorbing water from the atmosphere. If absorbing a large amount of water from the atmosphere, the water that has entered the matrix of the film and remained therein may impair the strength of the film. As for a step of drying the film-forming solution, it is preferred that the step be carried out in a way such that the step incudes an air drying step under an application environment; and a heating and drying step involving heating. The air drying step may be performed by exposing the coating film of the forming solution to an atmosphere whose relative humidity is maintained at a value of lower than 40%, or even at a value of 30% or lower.

In the heating and drying step, a matrix of silicon oxide (network of Si—O bonds) grows as a polycondensation reaction of silanol groups that have been generated by hydrolyzation progresses, and as the removal of a liquid component(s) remaining in the film, particularly the removal of water, progresses. The heating and drying step may be performed by exposing the coating film to an atmosphere of not higher than 300° C., such as an atmosphere of 100 to 200° C. The heating and drying step may be performed in a way such that the coating film is exposed to and heated in an atmosphere of particularly not higher than 300° C., such as an atmosphere of 100 to 200° C. or even an atmosphere of 50 to 100° C., in certain cases. It is preferred that the heating temperature in the heating and drying step be not higher than the melting points of the ultraviolet absorber a added as fine particles and the organic compound B, particularly not higher than the melting point of the ultraviolet absorber a added as fine particles. It is preferred that the heating temperature for heating the film in the heating and drying step be selected from a range lower than the melting point of the ultraviolet absorber a added as fine particles. If adding the organic compound B as fine particles, it is preferred that the heating temperature be selected from a range(s) lower than the melting point of the ultraviolet absorber a and the melting point of the organic compound B. In this case, it is preferred that the melting point of each of the ultraviolet absorber a and the organic compound B be not lower than 65° C., particularly not lower than 100° C. or, for example, 120 to 240° C., and even 140 to 240° C.

A glass can be obtained by a liquid phase film-forming method, as a result of sequentially performing the series of the aforementioned steps which are (a) the step of preparing the film-forming solution of the ultraviolet shielding film that contains the fine particles of the ultraviolet absorber a and others. (b) the step of applying the film-forming solution to a glass, and (c) the step of drying the film-forming solution. This production method is a method for producing a glass article having an ultraviolet shielding film. The production method includes a step of preparing a film-forming solution of an ultraviolet shielding film that contains, as a solute, a silicon-containing compound such as silicon alkoxide, and contains, as fine particles having an average particle size of not larger than 150 nm, the organic compound A being solid at normal temperature and having an average molecular weight of not higher than 5,000; a step of applying such film-forming solution to a glass; and a step of forming an ultraviolet shielding film on the glass by drying the film-forming solution. This production method constitutes another aspect of the present invention. It is preferred that the ultraviolet shielding film have a film thickness of larger than 300 om but not larger than 15 μm, more preferably 500 nm to 10 μm, particularly preferably 1,000 nm to 5,000 nm. When the film is excessively thin, a sufficient ultraviolet shielding capability may not be achieved; when the film is excessively thick, the transparency of the glass may be impaired as the transmittance of the film decreases.

There are no particular restrictions on the glass; a soda-lime silicate glass may be used. Typical composition examples of this glass are shown below. In the following descriptions, the unit "%" indicating the content ratio of each component contained in the glass all represents % by mass. An alkali metal oxide ($R_2O$) specifically refers to a total amount of $Na_2O$ and $K_2O$. $T-Fe_2O_3$ is a total iron oxide expressed in terms of $Fe_2O_3$. Further, each composition example may also contain a minor component(s) not shown. For example, there may be used a general clear glass. One example of a glass composition thereof is shown below.

(Clear Glass)
    $SiO_2$: 70 to 73% by mass
    $Al_2O_3$: 0.6 to 2.4%
    CaO: 7 to 12%
    MgO: 1.0 to 4.5%
    $R_2O$: 13 to 15% (R is an alkali metal)
    Total iron oxide ($T-Fe_2O_3$) expressed in terms of $Fe_2O_3$:
      0.08 to 0.2%

Further, it is preferred that the concentration of the iron oxide be increased, and that there be used a soda-lime silicate glass having a composition containing, if necessary, other ultraviolet absorbing components such as titanium oxide and cerium oxide. As a soda-lime silicate glass, there may be used a glass having a glass composition containing iron oxide by an amount of greater than 0.2%, preferably not smaller than 0.4%, more preferably not smaller than 0.5%, for example, 0.5 to 1.3%; and having a light transmittance of not higher than 70%, preferably not higher than 50% at a wavelength of 380 nm, and a light transmittance of not lower than 75% at a wavelength of 550 nm. For example, there may be used a green glass, a heat-absorbing glass and a UV-cut green glass. Several composition examples of these glasses are provided below.

(Green Glass)
    $SiO_2$: 70 to 73% by mass
    $Al_2O_3$: 0.6 to 2.4%
    CaO: 7 to 12%
    MgO: 1.0 to 4.5%
    $R_2O$: 13 to 15% (R is an alkali metal)
    Total iron oxide ($T-Fe_2O_3$) expressed in terms of $Fe_2O_3$:
      0.4 to 0.6%

(Heat-Absorbing Glass)
    $SiO_2$: 70 to 73% by mass
    $Al_2O_3$: 0.6 to 2.4%
    CaO: 7 to 12%
    MgO: 1.0 to 4.5%
    $R_2O$: 13 to 15% (R is an alkali metal)
    Total iron oxide ($T-Fe_2O_3$) expressed in terms of $Fe_2O_3$:
      0.5 to 1.1%

(UV-Cut Green Glass)
    $SiO_2$: 70 to 73% by mass
    $Al_2O_3$: 0.6 to 2.4%
    CaO: 7 to 12%
    MgO: 1.0 to 4.5%
    $R_2O$: 13 to 15% (R is an alkali metal)
    Total iron oxide ($T-Fe_2O_3$) expressed in terms of $Fe_2O_3$:
      0.7 to 1.3%
    $CeO_2$: 0 to 2%
    $TiO_2$: 0 to 0.5%

Here, there may also be used a high transmittance glass whose iron oxide content is not larger than 0.1% by mass, preferably 0.01 to 0.06%. One example thereof is shown below.

(High Transmittance Glass)
    $SiO_2$: 70 to 73% by mass
    $Al_2O_3$: 0.6 to 2.4%
    CaO: 7 to 12%

MgO: 1.0 to 4.5%
    $R_2O$: 13 to 15% (R is an alkali metal)
    Total iron oxide ($T-Fe_2O_3$) expressed in terms of $Fe_2O_3$:
      0.01 to 0.06%

Here, in the above descriptions, the iron oxide concentration is a numerical value calculated by converting the total iron oxide contained in the glass into $Fe_2O_3$.

However, the glass is not limited to those described above, but may be that having a low light transmittance in the visible range. As such glass, there may be listed, for example, a glass that is produced as a glass for use in vehicles, and has a light transmittance of 20 to 60% at a wavelength of 550 nm. Since it is difficult to satisfactorily shield in particular lights in an ultraviolet region of a long-wavelength region with the components composing the glass alone, the usage of the aforementioned ultraviolet shielding film shall be effective even in the case of a glass having a low visible light transmittance.

As for the glass having the above ultraviolet shielding film, an ultraviolet transmittance $T_{uv}380$ thereof in accordance with ISO9050 (1990 edition) may be not higher than 2%, preferably not higher than 1%, more preferably not higher than 0.5%. Further, as for the glass having the above ultraviolet shielding film, an ultraviolet transmittance $T_{uv}400$ thereof that is calculated in accordance with ISO13837 (convention A) may be not higher than 2%, preferably not higher than 1.5%, particularly preferably not higher than 1%. As for the glass having the above ultraviolet shielding film, a visible light transmittance YA thereof that is measured using an A light source of CIE standard may be not lower than 70%. The glass having the above ultraviolet shielding film may have a Tu 400 of not higher than 2% and a YA of not lower than 70%.

As for a transmitted light from a C light source of CIE standard, the glass having the above ultraviolet shielding film may have a* of −15 to 0 and b* of not higher than 12 in the $L^*a^*b^*$color system. It may be that a* is −12 to −7, for example −9 to −8; b* is not higher than 10, for example 5 to 10. Further, as for the transmitted light from the C light source of CIE standard, a yellow index YI of the glass having the above ultraviolet shielding film, as provided in Japanese Industrial Standards (JIS) K7373:2006, may be not higher than 14. The yellow index YI may be not higher than 10, or even not higher than 8. Further, in the case of the glass having the above ultraviolet shielding film, a dominant wavelength of the transmitted light with regard to the C light source of CIE standard may be 560 nm or shorter. The dominant wavelength may be 555 nm or shorter, for example, in a range of 550 to 555 nm. As for the glass having the above ultraviolet shielding film, a blue light cut ratio calculated based on a blue light hazard function defined in JIS T7330 may be not higher than 41%, preferably not higher than 37%, particularly preferably not higher than 36%. Here, the blue light cut ratio can be defined as a value, expressed in percentage, of a ratio of a reduced effective radiation intensity of the blue light of sunlight that is associated with retinal damage after passing sunlight through the glass to an effective radiation intensity thereof before passing sunlight through the glass (referred to as effective radiation intensity of sunlight hereunder). Specifically, the blue light cut ratio can be obtained by the following method. The effective radiation intensity of sunlight is obtained by performing summation from wavelengths 380 to 550 nm with regard to a weighting function of the blue light disorder function described in an appendix A of JIS T7330: 2000. Next, the effective radiation intensity of the light that has passed through the glass (referred to as effective radiation intensity of transmitted light hereunder) is obtained by taking a sum of products of spectral transmittances of the glass and weighting functions at each wavelength in the above wavelength region. A ratio of the effective radiation intensity of the transmitted light to the effective radiation intensity of sunlight is taken, followed by subtracting such value from 1, and then converting the result obtained into a percentage.

As for the glass having the above ultraviolet shielding film, a difference $\Delta T_{uv}400$ may be not larger than 2%, or even not larger than 1%, particularly not larger than 0.5%, the difference $\Delta T_{uv}400$ being obtained by subtracting an ultraviolet transmittance $T_{uv}400$ before performing irradiation for 100 hours using an ultraviolet having a wavelength of 295 to 450 nm and an irradiance of 76 mW/cm$^2$ from an ultraviolet transmittance $T_{uv}400$ after performing irradiation in such manner. As for the glass having the above ultraviolet shielding film, a difference $\Delta YA$ may be not smaller than $-0.5\%$, particularly not smaller than $-0.2\%$, the difference $\Delta YA$ being obtained by subtracting a visible light transmittance YA before performing irradiation for 100 hours using an ultraviolet having a wavelength of 295 to 450 nm and an irradiance of 76 mW/cm$^2$ from a visible light transmittance YA after performing irradiation in such manner. The $\Delta YA$ may be $-0.5\%$ to 1%, or even $-0.2\%$ to 0.5%

WORKING EXAMPLES

The present invention is described in greater detail hereunder with reference to working examples. However, the invention is not limited to these working examples.

<Synthesis Example 1> Synthesis of Compound 1

[Chemical formula 18]

2-(2-hydroxy-3-tert-butyl-5-methylphenyl)-5-chlorobenzotriazole (25.0 g, 79.2 mmol), benzenethiol (17.4 g, 158.3 mmol), potassium carbonate (24.1 g, 174.2 mmol) and potassium iodide (0.9 g, 5.5 mmol) were reacted in 62.5 g of DMF at 125° C., for 12 hours. After completing the reaction, pH was adjusted, followed by performing filtration, MeOH washing, water washing, recrystallization and then column purification to obtain a compound 1.

FT-IR (KBr): 3,000 cm$^{-1}$: O—H stretching vibration 1,445, 1,390 cm$^{-1}$: triazole ring stretching vibration 665 cm$^{-1}$: C—S stretching vibration $^1$H-NMR (CDCl$_3$ 400 MHz): δ 1.48 (s, 9H, -Ph-OH—CH$_3$—C(CH$_3$)$_3$), 2.37 (s, 3H, -Ph-OH—CH$_3$—C(CH$_3$)$_3$), 7.16 (s, 1H), 7.38 (d, 4H), 7.48 (s, 2H), 7.68 (s, 1H), 7.83 (d, 1H), 8.03 (d, 1H), (insg.10arom. CH), 11.55 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 116.8, 118.0, 119.3, 128.3, 128.8, 129.6, 132.7 (CH$_{arom}$), 125.5, 141.2, 143.2 (CH$_{arom}$), 129.8 (C$_{arom}$—CH$_3$), 139.2 (C$_{arom}$—S), 139.2 (S—C$_{arom}$), 139.2 (C$_{arom}$—C(CH$_3$)$_3$), 146.7 (C$_{arom}$—OH)

<Synthesis Example 2> Synthesis of Compound 2

[Chemical formula 19]

2-(2-hydroxy-3-tert-butyl-5-methylphenyl)-5-chlorobenzotriazole (25.0 g, 79.2 mmol), 4-tert-butylbenzenethiol (26.3 g, 158.3 mmol), potassium carbonate (24.1 g, 174.2 mmol) and potassium iodide (0.9 g, 5.5 mmol) were reacted in 62.5 g of DMF at 125° C., for 12 hours. After completing the reaction, pH was adjusted, followed by performing filtration, MeOH washing, water washing, recrystallization and then column purification to obtain a compound 2.

FT-IR (KBr): 3,000 cm$^{-1}$: O—H stretching vibration 1,444, 1,390 cm$^{-1}$: triazole ring stretching vibration 668 cm$^{-1}$: C—S stretching vibration $^1$H-NMR (CDCl$_3$ 400 MHz): δ 1.36 (s, 9H, —S-Ph-C(CH$_3$)$_3$), 1.48 (s, 9H, -Ph-OH—CH$_3$—C(CH$_3$)$_3$), 2.37 (s, 3H, -Ph-OH—CH$_3$—C(CH$_3$)$_3$), 7.16 (s, 1H), 7.35 (d, 1H), 7.44 (s, 4H), 7.59 (s, 1H), 7.81 (d, 1H), 8.02 (d, 1H), (insg.9arom. CH), 11.58 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 31.3 (—S-Ph-C(CH$_3$)$_3$), 34.8 (—S-Ph-C(CH$_3$)$_3$), 35.4 (-Ph-OH—CH$_3$—C(CH$_3$)$_3$), 115.4, 117.8, 119.3, 126.8, 128.8, 129.2, 133.2 (CH$_{arom}$), 125.4, 141.5, 143.3 (C$_{arom}$), 128.3 (C$_{arom}$—CH$_3$), 138.5 (C$_{arom}$—S), 138.5 (S—C$_{arom}$), 139.1, 152.0 (C$_{arom}$—C(CH$_3$)$_3$), 146.7 (C$_{arom}$—OH)

<Synthesis Example 3> Synthesis of Compound 3

[Chemical formula 20]

2-(2-hydroxy-3-tert-butyl-5-methylphenyl)-5-chlorobenzotriazole (25.0 g, 79.2 mmol), 2,4-dimethylbenzenethiol (21.9 g, 158.3 mmol), potassium carbonate (24.1 g, 174.2 mmol) and potassium iodide (0.9 g, 5.5 mmol) were reacted in 62.5 g of DMF at 125° C., for 12 hours. After completing the reaction, pH was adjusted, followed by performing filtration, MeOH washing, water washing, recrystallization and then column purification to obtain a compound 3.

FT-IR (KBr): 3,000 cm$^{-1}$: O—H stretching vibration 1,447, 1,385 cm$^{-1}$: triazole ring stretching vibration 665 cm$^{-1}$: C—S stretching vibration $^1$H-NMR (CDCl$_3$ 400 MHz): δ 1.47 (s, 9H, -Ph-OH—CH$_3$—C(CH$_3$)$_3$), 2.38 (s, 9H, -Ph-OH—CH$_3$—C(CH$_3$)$_3$, -Ph-CH$_3$—CH$_3$), 7.08 (d, 1H), 7.15 (d, 2H), 7.30 (m, 2H), 7.43 (d, 1H), 7.77 (d, 1H), 8.01 (d, 1H), (insg.8arom. C$\underline{H}$), 11.57 (s, 1H, -Ph-O$\underline{H}$—CH$_3$—C(CH$_3$)$_3$)

$^{13}$C-NMR (CDCl$_3$ 100 MHz): δ 20.6 (-Ph-$\underline{C}$H$_3$—CH$_3$), 20.9 (-Ph-OH—$\underline{C}$H$_3$—C(CH$_3$)$_3$), 20.6 (-Ph-$\overline{C}$H$_3$—CH$_3$), 29.5 (-Ph-OH—$\overline{C}$H$_3$—C(C$\underline{H}_3$)$_3$), 35.4 (-Ph-OH—CH$_3$—$\underline{C}$ (CH$_3$)$_3$), 113.3, 117.7, 119.2, 128.0, 128.3, 128.6, 135.8 (CH$_{arom}$), 125.4, 141.3, 143.4, 152.0 (C$_{arom}$), 128.2, 132.0, 141.9 ($\underline{C}_{arom}$—CH$_3$), 138.8 ($\underline{C}_{arom}$—C(CH$_3$)$_3$), 139.1 ($\underline{C}_{arom}$—S), 139.9 (S—$\underline{C}_{arom}$), 146.6 ($\underline{C}_{arom}$—OH)

<Synthesis Example 4> Synthesis of Compound 4

[Chemical formula 21]

2-(2-hydroxy-3-tert-butyl-5-methylphenyl)-5-chlroben-zotriazole (25.0 g, 79.2 mmol), 3-methoxybenzenethiol (22.2 g, 158.3 mmol), potassium carbonate (24.1 g, 174.2 mmol) and potassium iodide (0.9 g, 5.5 mmol) were reacted in 62.5 g of DMF at 125° C., for 12 hours. After completing the reaction, pH was adjusted, followed by performing filtration, MeOH washing, water washing, recrystallization and then column purification to obtain a compound 4.

FT-IR (KBr): 3,000 cm$^{-1}$: O—H stretching vibration 1,450, 1,380 cm$^{-1}$: triazole ring stretching vibration 660 cm 1: C—S stretching vibration $^1$H-NMR (CDCl$_3$ 400 MHz): δ 1.48 (s, 9H, -Ph-OH—CH$_3$—C(C$\underline{H}_3$)$_3$), 2.38 (s, 3H, -Ph-OH—C$\underline{H}_3$—C(CH$_3$)$_3$), 3.79 (s, 3H, C$\underline{H}_3$O-Ph-S—), 6.90 (d, 1H), 7.$\overline{00}$ (s, 1H), 7.06 (d, 1H), 7.17 (s, 1H), 7.30 (s, 1H), 7.40 (d, 1H), 7.74 (s, 1H), 7.84 (s, 1H), 8.04 (s, 1H), (insg.9arom. C$\underline{H}$), 11.56 (s, 1H, -Ph-O$\underline{H}$—CH$_3$—C(CH$_3$)$_3$ $^{13}$C-NMR (CDCl$_3$ 100 MHz): δ 20.9 (-Ph-OH—$\underline{C}$H$_3$—C(CH$_3$)$_3$), 29.5 (-Ph-OH—CH$_3$—C(C$\underline{H}_3$)$_3$), 35.4 (-Ph-OH—CH$_3$—$\underline{C}$(CH$_3$)$_3$), 55.4 (—S-Ph-O—$\underline{C}$H$_3$), 114.1, 117.3, 117.5, 118.0, 119.3, 124.6, 128.9, 130.0, 130.4 (CH$_{arom}$), 125.4, 141.5, 143.3 (C$_{arom}$), 128.3 ($\underline{C}_{arom}$—CH$_3$), 138.5 ($\underline{C}_{arom}$—S), 138.5 (S—$\underline{C}_{arom}$), 139.1 ($\underline{C}_{arom}$—C(CH$_3$)$_3$), 146.7 ($\underline{C}_{arom}$—OH), 159.9 ($\underline{C}_{arom}$—OCH$_3$)

<Synthesis Example 5> Synthesis of Compound 5

[Chemical formula 22]

4-tert-amylphenol (25.0 g, 152.2 mmol), dimethylcar-bamoyl chloride (28.2 g, 228.3 mmol) and sodium hydride (7.3 g, 167.4 mmol) were reacted in 50 g of THF at 60° C., for four hours. After completing the reaction, toluene and water were added, followed by adding hydrochloric acid for acid treatment, and then distilling away a water-washed organic layer under a reduced pressure. A solid intermediate 5-1 was then obtained by performing column purification on the liquid obtained. The intermediate 5-1 obtained was then reacted in 50 g of sulfolane at 240° C., for four hours. After completing the reaction, toluene and water were added to carry out water washing, followed by performing distillation under a reduced pressure to obtain a liquid intermediate 5-2. The intermediate 5-2 obtained and potassium hydroxide were stirred in ethanol at 60° C., for three hours. After cooling, hydrochloric acid was added to perform stirring, followed by carrying out water washing, recrystallization and then column purification to obtain 4-tert-amylthiophe-nol.

2-(2-hydroxy-3-tert-butyl-5-methylphenyl)-5-chloroben-zotriazole (3.8 g, 12.0 mmol), 4-tert-amylthiophenol (2.8 g, 15.5 mmol), potassium carbonate (3.6 g, 26.4 mmol) and potassium iodide (0.1 g, 0.8 mmol) were reacted in 62.5 g of DMF at 125° C., for 12 hours. After completing the reaction, pH was adjusted, followed by performing filtration, MeOH washing, water washing, recrystallization and then column purification to obtain a compound 5.

FT-IR (KBr): 3,000 cm$^{-1}$: O—H stretching vibration 1,450, 1,380 cm$^{-1}$: triazole ring stretching vibration 660 cm$^{-1}$: C—S stretching vibration $^1$H-NMR (CDCl$_3$ 400 MHz): δ 0.72 (t, 3H, —S-Ph-CCH$_2$C$\underline{H}_3$), 1.31 (s, 6H, —S-Ph-C(C$\underline{H}_3$)$_2$), 1.48 (s, 9H, -Ph-OH—CH$_3$—C(C$\underline{H}_3$)$_3$), 1.66 (q, 2H, —S-Ph-CC$\underline{H}_2$CH$_3$), 2.37 (s, 3H, -Ph-OH—C$\underline{H}_3$—C(CH$_3$)$_3$), 7.16 (d, 1H), 7.36 (m, 3H), 7.44 (d, 2H), 7.60 (s, 1H), 7.81 (d, 1H), 8.02 (s, 1H), (insg.9arom. C$\underline{H}$), 11.58 (s, 1H, -Ph-O$\underline{H}$—CH$_3$—C(CH$_3$)$_3$)

$^{13}$C-NMR (CDCl$_3$ 100 MHz): δ 9.18 (—S-Ph-CC$\underline{H}_2$CH$_3$), 20.9 (-Ph-OH—$\underline{C}$H$_3$—C(CH$_3$)$_3$), 28.3 (—S-Ph-C(C$\underline{H}_3$)$_2$), 29.5 (-Ph-OH—CH$_3$—C(C$\underline{H}_3$)$_3$), 35.4 (-Ph-OH—CH$_3$—$\underline{C}$(CH$_3$)$_3$), 36.8 (—S-Ph-$\underline{C}$(CH$_3$)$_2$), 38.1 (—S-Ph-C$\underline{C}$H$_2$CH$_3$), 115.5, 117.8, 119.3, 127.4, 128.8, 129.3, 133.0 (CH$_{arom}$), 125.4, 141.5, 143.3 (C$_{arom}$), 128.3 ($\underline{C}_{arom}$—CH$_3$), 138.4 ($\underline{C}_{arom}$—S), 138.4 (S—$\underline{C}_{arom}$), 139.1 ($\underline{C}_{arom}$—C(CH$_3$)$_3$), 146.7 ($\underline{C}_{arom}$—OH), 150.4 ($\underline{C}_{arom}$—C(CH$_3$)$_2$)

<Synthesis Example 6> Synthesis of Compound 6

[Chemical formula 23]

2-(2-hydroxy-3-tert-butyl-5-methylphenyl)-5-chloroben-zotriazole (25.0 g, 79.2 mmol), 4-isopropylbenzenethiol (24.1 g, 158.3 mmol), potassium carbonate (24.1 g, 174.2 mmol) and potassium iodide (0.92 g, 5.54 mmol) were reacted in 62.5 g of DMF at 125° C., for 12 hours. After completing the reaction, pH was adjusted, followed by performing filtration, MeOH washing, water washing, recrystallization and then column purification to obtain a compound 6.

FT-IR (KBr): 3,000 cm$^{-1}$: O—H stretching vibration 1,446, 1,389 cm$^{-1}$: triazole ring stretching vibration 666 cm$^{-1}$: C—S stretching vibration $^1$H-NMR (CDCl$_3$ 400 MHz): δ 1.30 (d, 6H, (CH$_3$)$_2$CH-Ph-S—), 1.48 (s, 9H, -Ph-OH—CH$_3$—C(CH$_3$)$_3$), 2.37 (s, 3H, -Ph-OH—CH$_3$—C(CH$_3$)$_3$), 2.95 (m, 1H, (CH$_3$)$_2$CH-Ph-S—), 7.16 (s, 1H), 7.28 (s, 2H), 7.36 (d, 1H), 7.45 (s, 2H), 7.57 (s, 1H), 7.81 (d, 1H), 8.02 (d, 1H), (insg.9arom. CH), 11.58 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 23.9 ((CH$_3$)$_2$CH-Ph-S—), 29.5 (-Ph-OH—CH$_3$—C(CH$_3$)$_3$), 33.9 ((CH$_3$)$_2$CH-Ph-S—), 35.4 (-Ph-OH—CH$_3$—C(CH$_3$)$_3$), 115.3, 117.8, 119.3, 127.9, 128.7, 129.2, 129.6, 133.6 (CH$_{arom}$), 125.4, 141.4, 143.3 (C$_{arom}$), 128.3 (C$_{arom}$—CH$_3$), 138.5 (C$_{arom}$—S), 138.5 (S—C$_{arom}$), 139.1 (C$_{arom}$—C(CH$_3$)$_3$), 146.7 (C$_{arom}$—OH), 149.7 (C$_{arom}$—CH)

<Synthesis Example 7> Synthesis of Compound 7

[Chemical formula 24]

4-(1,1,3,3-tetramethylbutyl) phenol (25.0 g, 121.2 mmol), dimethylcarbamoyl chloride (22.5 g, 181.7 mmol) and sodium hydride (5.8 g, 133.3 mmol) were reacted in 50 g of THF at 60° C., for four hours. After completing the reaction, toluene and water were added, followed by adding hydrochloric acid for acid treatment, and then distilling away a water-washed organic layer under a reduced pressure. A solid intermediate 7-1 was then obtained by performing column purification on the liquid obtained. The intermediate 7-1 obtained was then reacted in 50 g of sulfolane at 240° C., for four hours. After completing the reaction, toluene and water were added to carry out water washing, followed by performing distillation under a reduced pressure to obtain a liquid intermediate 7-2. The intermediate 7-2 obtained and potassium hydroxide were stirred in ethanol at 60° C., for three hours. After cooling, hydrochloric acid was added to perform stirring, followed by carrying out water washing, recrystallization and then column purification to obtain 4-(1,1,3,3-tetramethylbutyl)thiophenol.

2-(2-hydroxy-3-tert-butyl-5-methylphenyl)-5-chloroben-zotriazole (5.5 g, 17.3 mmol), 4-(1,1,3,3-tetramethylbutyl) thiophenol (5.0 g, 22.5 mmol), potassium carbonate (5.3 g, 38.1 mmol) and potassium iodide (0.2 g, 1.2 mmol) were reacted in 60 g of DMF at 125° C., for 12 hours. After completing the reaction, pH was adjusted, followed by performing filtration, MeOH washing, water washing, recrystallization and then column purification to obtain a compound 7.

FT-IR (KBr): 3.000 cm$^{-1}$: O—H stretching vibration 1,450, 1,380 cm$^{-1}$: triazole ring stretching vibration 660 cm$^{-1}$: C—S stretching vibration $^1$H-NMR (CDCl$_3$ 400 MHz): δ 0.76 (s, 9H, —S-Ph-CCH$_2$C(CH$_3$)$_3$), 1.40 (s, 6H, —S-Ph-C(CH$_3$)$_2$), 1.48 (s, 9H, -Ph-OH—CH$_3$—C(CH$_3$)$_3$), 1.77 (s, 2H, —S-Ph-CCH$_2$), 2.37 (s, 3H, -Ph-OH—CH$_3$—C(CH$_3$)$_3$), 7.16 (d, 1H), 7.34 (m, 1H), 7.42 (s, 4H), 7.59 (s, 1H), 7.80 (d, 1H), 8.02 (s, 1H), (insg.9arom. CH), 11.58 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 31.8 (—S-Ph-

CCH$_2$C(CH$_3$)$_3$), 31.4 (—S-Ph-C(CH$_3$)$_2$), 32.5 (—S-Ph-C), 35.4 (-Ph-OH—CH$_3$—C(CH$_3$)$_3$), 38.6 (—S-Ph-CCH$_2$C(CH$_3$)$_3$), 57.0 (—S-Ph-CCH$_2$), 115.4, 117.8, 119.3, 127.6, 128.7, 129.2, 133.0 (CH$_{arom}$), 125.4, 141.5, 143.3 (C$_{arom}$), 128.3 (C$_{arom}$—CH$_3$), 138.5 (C$_{arom}$—S), 138.5 (S—C$_{arom}$), 139.1 (C$_{arom}$—C(CH$_3$)$_3$), 146.7 (C$_{arom}$—OH), 151.2 (C$_{arom}$—C(CH$_2$)$_2$)

<Synthesis Example 8> Synthesis of Compound 8

[Chemical formula 25]

2-(2-hydroxy-3-tert-butyl-5-methylphenyl)-5-chloroben-zotriazole (25.0 g, 79.2 mmol), 5-tert-butyl-2-methylben-zenethiol (28.5 g, 158.3 mmol), potassium carbonate (24.1 g, 174.2 mmol) and potassium iodide (0.92 g, 5.54 mmol) were reacted in 62.5 g of DMF at 125° C. for 12 hours. After completing the reaction, pH was adjusted, followed by performing filtration, MeOH washing, water washing, recrystallization and then column purification to obtain a compound 8.

FT-IR (KBr): 3,000 cm$^{-1}$: O—H stretching vibration 1,450, 1,385 cm$^{-1}$: triazole ring stretching vibration 665 cm 1: C—S stretching vibration $^1$H-NMR (CDCl$_3$ 400 MHz): δ 1.31 (s, 9H, —S-Ph-C(CH$_3$)$_3$), 1.48 (s, 9H, -Ph-OH—CH$_3$—C(CH$_3$)$_3$), 2.36 (s, 6H, -Ph-OH—CH$_3$—C(CH$_3$)$_3$, —S-Ph-CH$_3$), 7.15 (d, 1H), 7.34 (m, 4H), 7.56 (d, 1H), 7.80 (d, 1H), 8.01 (d, 1H), (insg.8arom. CH), 11.57 (s, 1H, -Ph-OH—CH$_3$—C(CH$_3$)$_3$)

$^{13}$C-NMR (CDCl$_3$ 100 MHz): δ 20.1 (-Ph-CH$_3$), 20.9 (-Ph-OH—CH$_3$—C(CH$_3$)$_3$), 29.5 (-Ph-OH—CH$_3$—C(CH$_3$)$_3$), 31.3 (-Ph-CH$_3$—C(CH$_3$)$_3$), 34.5 (-Ph-CH$_3$—C(CH$_3$)$_3$), 35.4 (-Ph-OH—CH$_3$—C(CH$_3$)$_3$), 113.6, 117.7, 119.2, 126.7, 128.7, 130.4, 130.8, 132.5 (CH$_{arom}$), 125.4, 141.3, 143.4, 152.0 (C$_{arom}$), 128.3, 128.4 (C$_{arom}$~CH$_3$), 138.5 (C$_{arom}$—S), 139.1 (S—C$_{arom}$), 138.8, 150.4 (C$_{arom}$—C(CH$_3$)$_3$), 146.6 (C$_{arom}$—OH)

<Synthesis Example 9> Synthesis of Compound 9

[Chemical formula 26]

2-(2-hydroxy-3-tert-butyl-5-methylphenyl)-5-chloroben-zotriazole (25.0 g, 79.2 mmol), p-toluenethiol (19.7 g, 158.3 mmol), potassium carbonate (24.1 g, 174.2 mmol) and potassium iodide (0.92 g, 5.54 mmol) were reacted in 62.5 g of DMF at 125° C., for 12 hours. After completing the reaction, pH was adjusted, followed by performing filtration, MeOH washing, water washing, recrystallization and then column purification to obtain a compound 9.

FT-IR (KBr): 3,000 cm$^{-1}$: O—H stretching vibration 1,444, 1,389 cm$^{-1}$: triazole ring stretching vibration 667 cm$^{-1}$: C—S stretching vibration $^1$H-NMR (CDCl$_3$ 400 MHz): δ 1.48 (s, 9H, -Ph-OH—CH$_3$—C(CH$_3$)$_3$), 2.37 (s, 3H, -Ph-OH—CH$_3$—C(CH$_3$)$_3$), 2.40 (s, 3H, CH$_3$-Ph-S—), 7.16 (s, 1H), 7.23 (s, 2H), 7.32 (d, 1H), 7.43 (s, 2H), 7.56 (s, 1H), 7.81 (d, 1H), 8.02 (d, 1H), (insg.9arom. CH), 11.56 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 21.2 (CH$_3$-Ph-S—), 29.5 (-Ph-OH—CH$_3$—C(CH$_3$)$_3$), 35.4 (-Ph-OH—CH$_3$—C(CH$_3$)$_3$), 115.3, 117.8, 119.3, 128.7, 129.3 130.5, 133.7 (CH$_{arom}$), 125.4, 141.2, 143.4 (C$_{arom}$), 128.3 (C$_{arom}$—CH$_3$), 138.9 (C$_{arom}$—S), 138.7 (S—C$_{arom}$), 139.1 (C$_{arom}$—C(CH$_3$)$_3$), 146.7 (C$_{arom}$—OH)

<Synthesis Example 10> Synthesis of Compound 10

[Chemical formula 27]

2,4-di-tert-amylphenol (25.0 g, 106.7 mmol), dimethyl-carbamoyl chloride (19.8 g, 160.0 mmol) and sodium hydride (5.1 g, 117.4 mmol) were reacted in 50 g of THF at 60° C., for four hours. After completing the reaction, toluene and water were added, followed by adding hydrochloric acid for acid treatment, and then distilling away a water-washed organic layer under a reduced pressure. A solid intermediate 10-1 was then obtained by performing column purification on the liquid obtained. The intermediate 10-1 obtained was then reacted in 50 g of sulfolane at 240° C., for four hours. After completing the reaction, toluene and water were added to carry out water washing, followed by performing distil-lation under a reduced pressure to obtain a liquid interme-diate 10-2. The intermediate 10-2 obtained and potassium hydroxide were stirred in ethanol at 60° C., for three hours. After cooling, hydrochloric acid was added to perform stirring, followed by carrying out water washing, recrystal-lization and then column purification to obtain 2,4-di-tert-amylthiophenol.

2-(2-hydroxy-3-tert-butyl-5-methylphenyl)-5-chloroben-zotriazole (2.9 g, 9.2 mmol), 2,4-di-tert-amylthiophenol (3.0 g, 12.0 mmol), potassium carbonate (2.8 g, 20.3 mmol) and potassium iodide (0.1 g, 0.6 mmol) were reacted in 60 g of DMF at 125° C., for 12 hours. After completing the reaction, pH was adjusted, followed by performing filtration, MeOH washing, water washing, recrystallization and then column purification to obtain a compound 10.

FT-IR (KBr): 3,000 cm$^{-1}$: O—H stretching vibration 1,450, 1,380 cm$^{-1}$: triazole ring stretching vibration 660 cm$^{-1}$: C—S stretching vibration $^1$H-NMR (CDCl$_3$ 400 MHz): δ 0.60 (m, 6H, —S-Ph-(CCH$_2$CH$_3$)$_2$), 1.23 (s, 6H, —S-Ph-C(CH$_3$)$_2$), 1.39 (m, 15H, —S-Ph-C(CH$_3$)$_2$, -Ph-OH—CH$_3$—C(CH$_3$)$_3$), 1.58 (q, 2H, —S-Ph-CCH$_2$CH$_3$), 1.96 (q, 2H, —S-Ph-CCH$_2$CH$_3$), 2.26 (s, 3H, -Ph-OH—CH$_3$—C(CH$_3$)$_3$), 7.05 (m, 2H), 7.20 (d, 1H), 7.27 (s, 1H), 7.30 (s, 1H)), 7.35 (s, 1H), 7.68 (d, 1H), 7.92 (d, 1H), (insg.8arom. CH), 11.50 (s, 1H, -Ph-OH—CH$_3$—C(CH$_3$)$_3$)

$^{13}$C-NMR (CDCl$_3$ 100 MHz): δ 9.22 (—S-Ph-CCH$_2$CH$_3$), 9.54 (—S-Ph-CCH$_2$CH$_3$), 20.9 (-Ph-OH—CH$_3$—C(CH$_3$)$_3$), 28.3 (—S-Ph-C(CH$_3$)$_2$), 28.8 (—S-Ph-C(CH$_3$)$_2$), 29.6 (-Ph-OH—CH$_3$—C(CH$_3$)$_3$), 34.4 (—S-Ph-C), 35.4 (-Ph-OH—CH$_3$—C(CH$_3$)$_3$), 37.0 (—S-Ph-C), 36.8 (—S-Ph-CCH$_2$), 40.5 (—S-Ph-CCH$_2$), 114.0, 117.6, 119.3, 125.0, 126.6, 127.3, 128.6, 128.7, 140.9 (CH$_{arom}$), 125.4, 141.2, 143.4 (C$_{arom}$), 128.3 (C$_{arom}$—CH$_3$), 138.3 (C$_{arom}$—S), 138.3 (S—C$_{arom}$), 139.1 (C$_{arom}$)—C(CH$_3$)$_3$), 146.6 (C$_{arom}$—OH), 150.1 (C$_{arom}$—C), 150.2 (C$_{arom}$—C)

<Synthesis Example 11> Synthesis of Compound 11

[Chemical formula 28]

2-(2-hydroxy-3-tert-butyl-5-methylphenyl)-5-chloroben-zotriazole (25.0 g, 79.2 mmol), 4-hydroxybenzenethiol (20.0 g, 158.3 mmol), potassium carbonate (24.1 g, 174.2 mmol) and potassium iodide (0.92 g, 5.54 mmol) were reacted in 62.5 g of DMF at 125° C., for 12 hours. After completing the reaction, pH was adjusted, followed by performing filtration, MeOH washing, water washing, recrystallization and then column purification to obtain a compound 11.

FT-IR (KBr): 3,000 cm$^{-1}$: O—H stretching vibration 1,445, 1,390 cm$^{-1}$: triazole ring stretching vibration 667 cm$^{-1}$: C—S stretching vibration $^1$H-NMR (CDCl$_3$ 400 MHz): δ 1.48 (s, 9H, -Ph-OH—CH$_3$—C(CH$_3$)$_3$), 2.36 (s, 3H, -Ph-OH—CH$_3$—C(CH$_3$)$_3$), 5.02 (s, 1H, -Ph-OH), 6.90 (d, 2H), 7.15 (s, 1H), 7.29 (d, 1H), 7.46 (m, 3H), 7.80 (d, 1H), 8.01 (d, 1H), (insg.9arom. CH), 11.57 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 114.0, 116.9, 117.7, 119.3, 128.3, 136.5 (CH$_{arom}$), 125.4, 141.3, 143.3 (C$_{arom}$), 128.7 (C$_{arom}$—CH$_3$), 139.1 (C$_{arom}$—C(CH$_3$)$_3$), 139.8 (C$_{arom}$—S), 139.8 (S—C$_{arom}$), 146.7, 156.6 (C$_{arom}$—OH)

<Synthesis Example 12> Synthesis of Compound 12

[Chemical formula 29]

2-(2-hydroxy-3-tert-butyl-5-methylphenyl)-5-chloroben-zotriazole (25.0 g, 79.2 mmol), 2-naphthalenethiol (25.4 g, 158.3 mmol), potassium carbonate (24.1 g, 174.2 mmol) and potassium iodide (0.92 g, 5.54 mmol) were reacted in 62.5 g of DMF at 125° C., for 12 hours. After completing the reaction, pH was adjusted, followed by performing filtration, MeOH washing, water washing, recrystallization and then column purification to obtain a compound 12.

FT-IR (KBr): 3,000 cm$^{-1}$: O—H stretching vibration 1,444, 1,389 cm$^{-1}$: triazole ring stretching vibration 667 cm$^{-1}$: C—S stretching vibration $^1$H-NMR (CDCl$_3$ 400 MHz): δ 1.48 (s, 9H, -Ph-OH—CH$_3$—C(CH$_3$)$_3$), 2.36 (s, 3H, -Ph-OH—CH$_3$—C(CH$_3$)$_3$), 7.16 (s, 1H), 7.39 (d, 1H), 7.51 (m, 3H), 7.72-7.86 (m, 5H), 8.02 (d, 1H), (insg.12arom. CH), 11.56 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 117.0, 118.0, 119.3, 126.8, 127.6, 127.8, 128.9, 129.4, 131.0, 131.9, 132.8, 133.9 (CH$_{arom}$), 125.4, 131.0, 133.9, 141.7, 143.2 (C$_{arom}$), 128.3 (C$_{arom}$—CH$_3$), 137.2 (C$_{arom}$—S), 137.2 (S—C$_{arom}$), 139.2 (C$_{arom}$—C(CH$_3$)$_3$), 146.7 (C$_{arom}$—OH)

<Synthesis Example 13> Synthesis of Compound 13

[Chemical formula 30]

2-(2-hydroxy-3-tert-butyl-5-methylphenyl)-5-chloroben-zotriazole (25.0 g, 79.2 mmol), 4,4'-thiobisbenzenethiol (9.0 g, 36.0 mmol), potassium carbonate (10.9 g, 79.2 mmol) and potassium iodide (0.4 g, 2.5 mmol) were reacted in 62.5 g of DMF at 125° C., for 12 hours. After completing the reaction, pH was adjusted, followed by performing filtration, MeOH washing, water washing, recrystallization and then column purification to obtain a compound 13.

FT-IR (KBr): 3,000 cm$^{-1}$: O—H stretching vibration 1,444, 1,389 cm$^{-1}$: triazole ring stretching vibration 667 cm$^{-1}$: C—S stretching vibration $^1$H-NMR (CDCl$_3$ 400 MHz): δ 1.48 (s, 18H, -Ph-OH—CH$_3$—C(CH$_3$)$_3$), 2.37 (s, 6H, -Ph-OH—CH$_3$—C(CH$_3$)$_3$), 7.17 (s, 2H), 7.32-7.39 (m, 10H), 7.77 (s, 2H), 7.83 (d, 2H), 8.03 (d, 2H), (insg.18arom. CH), 11.53 (s, 2H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 118.0, 118.2, 119.4, 129.0, 130.2, 131.9, 132.6, 133.6 (CH$_{arom}$), 125.3, 141.8, 143.2 (C$_{arom}$), 128.4 (C$_{arom}$—CH$_3$), 135.3 (C$_{arom}$—S), 136.0 (S—C$_{arom}$), 139.2 (C$_{arom}$—C(CH$_3$) 3), 146.8 (C$_{arom}$—OH)

<Synthesis Example 14> Synthesis of Compound 14

[Chemical formula 31]

2,2-bis(4-hydroxyphenyl) propane (24.6 g, 107.8 mmol), dimethylcarbamoyl chloride (40.0 g, 323.6 mmol) and sodium hydride (10.4 g, 238.4 mmol) were reacted in 100 g of THF at 60° C., for four hours. After completing the reaction, toluene and water were added, followed by adding hydrochloric acid for acid treatment, and then distilling away a water-washed organic layer under a reduced pressure. A solid intermediate 14-1 was then obtained by performing column purification on the liquid obtained. The intermediate 14-1 obtained was then reacted in 50 g of sulfolane at 240° C., for four hours. After completing the reaction, toluene and water were added to carry out water washing, followed by performing distillation under a reduced pressure to obtain a solid intermediate 14-2. The intermediate 14-2 obtained and potassium hydroxide were stirred in ethanol at 60° C., for three hours. After cooling, hydrochloric acid was added to perform stirring, followed by carrying out water washing, recrystallization and then column purification to obtain 2,2-bis(4-mercaptophenyl) propane.

2-(2-hydroxy-3-tert-butyl-5-methylphenyl)-5-chloroben-zotriazole (8.0 g, 25.3 mmol), 2,2-bis(4-mercaptophenyl) propane (3.0 g, 11.5 mmol), potassium carbonate (7.0 g, 50.6 mmol) and potassium iodide (0.3 g, 1.8 mmol) were reacted in 60 g of DMF at 125° C., for 12 hours. After completing the reaction, pH was adjusted, followed by performing filtration, MeOH washing, water washing, recrystallization and then column purification to obtain a compound 14.

FT-IR (KBr): 3,000 cm$^{-1}$: O—H stretching vibration 1,450, 1,380 cm$^{-1}$: triazole ring stretching vibration 660 cm$^{-1}$: C—S stretching vibration $^1$H-NMR (CDCl$_3$ 400 MHz): δ 1.49 (s, 18H, -Ph-OH—CH$_3$—C(CH$_3$)$_3$), 1.73 (s, 6H, —S-Ph-C(CH$_3$)$_3$), 2.37 (s, 6H, -Ph-OH—CH$_3$—C(CH$_3$)$_3$), 7.16 (d, 2H), 7.29 (m, 4H), 7.37 (m, 2H), 7.41 (m, 4H), 7.67 (s, 2H), 7.81 (d, 2H), 8.02 (s, 2H), (insg.18arom. CH), 11.58 (s, 2H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 30.6 (—S-Ph-C(CH$_3$)$_2$-Ph-S), 5.4 (-Ph-OH—CH$_3$—C(CH$_3$)$_3$), 43.0 (—S-Ph-C(CH$_3$)$_2$-Ph-S), 116.3, 117.9, 119.3, 128.1, 128.8, 129.6, 132.7 (CH$_{arom}$), 125.4, 141.5, 143.3 (C$_{arom}$), 128.3 (C$_{arom}$—CH$_3$), 137.6 (C$_{arom}$—S), 137.6 (S—C$_{arom}$), 139.2 (C$_{arom}$—C(CH$_3$)$_2$), 146.7 (C$_{arom}$—OH)

<Synthesis Example 15> Synthesis of Compound 15

Biphenyl-4,4'-diol (20.0 g, 107.4 mmol), dimethylcar-bamoyl chloride (39.8 g, 322.0 mmol) and sodium hydride (10.3 g, 236.1 mmol) were reacted in 100 g of THF at 60° C., for four hours. After completing the reaction, toluene and water were added, followed by adding hydrochloric acid for acid treatment, and then distilling away a water-washed organic layer under a reduced pressure. A solid intermediate 15-1 was then obtained by performing column purification on the liquid obtained. The intermediate 15-1 obtained was then reacted in 50 g of sulfolane at 240° C., for four hours. After completing the reaction, toluene and water were added to carry out water washing, followed by performing distil-lation under a reduced pressure to obtain a solid intermediate 15-2. The intermediate 15-2 obtained and potassium hydrox-ide were stirred in ethanol at 60° C., for three hours. After cooling, hydrochloric acid was added to perform stirring, followed by carrying out water washing, recrystallization and then column purification to obtain biphenyl-4,4'-dithiol.

2-(2-hydroxy-3-tert-butyl-5-methylphenyl)-5-chloroben-zotriazole (4.6 g, 14.6 mmol), biphenyl-4,4'-dithiol (1.5 g, 6.9 mmol)), potassium carbonate (4.0 g, 28.9 mmol) and potassium iodide (0.2 g, 1.2 mmol) were reacted in 60 g of DMF at 125° C., for 12 hours. After completing the reaction, pH was adjusted, followed by performing filtration, MeOH washing, water washing, recrystallization and then column purification to obtain a compound 15.

FT-IR (KBr): 3,000 cm$^{-1}$: O—H stretching vibration 1,450, 1,380 cm$^{-1}$: triazole ring stretching vibration 660 cm$^{-1}$: C—S stretching vibration $^1$H-NMR (CDCl$_3$ 400 MHz): δ 1.48 (s, 18H, -Ph-OH—CH$_3$—C(CH$_3$)$_3$), 2.38 (s, 6H, -Ph-OH—CH$_3$—C(CH$_3$)$_3$), 7.17 (d, 2H), 7.41 (d, 2H), 7.55 (d, 4H), 7.41 (d, 4H), 7.77 (s, 2H), 7.85 (d, 2H), 8.04 (d, 2H), (insg.18arom. CH), 11.56 (s, 2H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 29.5 (-Ph-OH—CH$_3$—C(CH$_3$)$_3$), 35.4 (-Ph-OH—CH$_3$—C(CH$_3$)$_3$), 118.1, 119.3, 128.1, 128.4, 128.9, 130.0, 132.8 (CH$_{arom}$), 125.4, 141.7 143.2 (C$_{arom}$), 128.4 (C$_{arom}$—CH$_3$), 136.9 (C$_{arom}$—S), 136.9 (S—C$_{arom}$), 139.2 (C$_{arom}$—C(CH$_3$)$_3$), 146.8 (C$_{arom}$—OH)

<Synthesis Example 16> Synthesis of Compound 16

[Chemical formula 33]

2-(2-hydroxy-3-tert-butyl-5-methylphenyl)-5-chloroben-zotriazole (32.3 g, 0.102 mol), cyclohexanethiol (23.8 g, 0.205 mol), potassium carbonate (31.1 g, 0.225 mol) and potassium iodide (1.2 g, 0.007 mol) were reacted in 100 g of DMF at 125° C., for 12 hours. After completing the reaction, pH was adjusted, followed by performing filtration, MeOH washing, water washing, recrystallization and then column purification to obtain a compound 16.

[Chemical formula 32]

FT-IR (KBr): 2,930 cm$^{-1}$: O—H stretching vibration 1,450, 1,391 cm$^{-1}$: triazole ring stretching vibration 667 cm$^{-1}$: C—S stretching vibration $^1$H-NMR (CDCl$_3$ 400 MHz): δ 1.40 (m, 4H, CH$_2$(CH$_2$)$_2$ (CH$_2$)$_2$CH—S), 1.49 (S, 9H, -Ph-OH—CH$_3$—C(CH$_3$)$_3$), 1.54 (m, 2H, CH$_2$ (CH$_2$)$_2$ (CH$_2$)$_2$CH—S), 1.83 (m, 2H, CH$_2$(CH$_2$)$_2$CH$_2$CH$_2$CH—S), 2.06 (m, 2H, CH$_2$(CH$_2$)$_2$ CH$_2$CH$_2$CH—S), 2.38 (s, 3H, -Ph-OH—CH$_3$—C(CH$_3$)$_3$), 3.29 (m, 1H, CH$_2$CH$_2$CH$_2$CH—S), 7.17 (s, 1H), 7.43 (d, 1H), 7.80 (s, 1H), 7.84 (d, 1H), 8.06 (d, 1H), (insg.5arom. CH), 11.62 (s, 1H, -Ph-OH—CH$_3$—C(CH$_3$)$_3$)

$^{13}$C-NMR (CDCl$_3$ 100 MHz): δ 20.9 (-Ph-OH—CH$_3$—C(CH$_3$)$_3$), 25.7 (CH$_2$(CH$_2$)$_2$ (CH$_2$)$_2$CH—S), 26.0 (CH$_2$ (CH$_2$)$_2$ (CH$_2$)$_2$CH—S), 29.5 (-Ph-OH—CH$_3$—C(CH$_3$)$_3$), 33.1 (CH$_2$(CH$_2$)$_2$(CH$_2$)$_2$CH—S), 35.4 (-Ph-OH—CH$_3$—C(CH$_3$)$_3$), 46.3 (CH$_2$(CH$_2$)$_2$ (CH$_2$)$_2$CH—S), 117.2, 117.5, 119.3, 128.3, 128.8 (CH$_{arom}$), 141.5, 143.2 (C$_{arom}$), 125.4 iodide (0.9 g, 0.005 mol) were reacted in 80 g of DMF at 125° C., for 12 hours. After completing the reaction, pH was adjusted, followed by performing filtration, MeOH washing, water washing, recrystallization and then column purification to obtain a compound 17.

FT-IR (KBr): 2,950 cm$^{-1}$: O—H stretching vibration 1,459, 1,388 cm$^{-1}$: triazole ring stretching vibration 670 cm$^{-1}$: C—S stretching vibration $^1$H-NMR (CDCl$_3$ 400 MHz): δ 2.38 (s, 3H, -Ph-OH—CH$_3$), 7.09 (d, 1H), 7.14 (d, 1H), 7.38 (d, 4H), 7.48 (d, 2H), 7.69 (s, 1H), 7.83 (d, 1H), 8.14 (d, 1H), (insg.11arom. CH), 10.94 (s, 1H, -Ph-OH—CH$_3$)

$^{13}$C-NMR (CDCl$_3$ 100 MHz): δ 20.5 (-Ph-OH—CH$_3$), 116.8, 118.1, 118.8, 121.0, 128.3, 129.6, 131.3, 132.8 (CH$_{arom}$), 124.8, 141.8, 143.4 (C$_{arom}$), 129.9 (C$_{arom}$—CH$_3$), 137.6 (C$_{arom}$—S), 139.2 (S—C$_{arom}$), 147.5 (C$_{arom}$—OH)

<Synthesis Example 18> Synthesis of Compound 18

[Chemical formula 35]

(C$_{arom}$—N), 131.2 (C$_{arom}$—CH$_3$), 136.1 (C$_{arom}$—S), 139.1 (C$_{arom}$—C(CH$_3$)$_3$), 146.7 (C$_{arom}$—OH)

<Synthesis Example 17> Synthesis of Compound 17

[Chemical formula 34]

2-(2-hydroxy-3-tert-butyl-5-methylphenyl)-5-chlorobenzotriazole (59.2 g, 0.187 mol) was added to 500 mL of toluene, and heating was then performed to 80° C. Next, aluminum trichloride (50.0 g, 0.375 mol) was added, followed by performing stirring for 30 minutes, and then cooling the mixture to room temperature before slowly adding 500 mL of an ice-cooled ion-exchange water thereto. Later, after removing an aqueous layer, washing an organic layer with water and then distilling away such organic layer under a reduced pressure, recrystallization was performed to obtain an intermediate 17-1. The obtained intermediate 17-1 (20.0 g, 0.077 mol), benzenethiol (11.0 g, 0.100 mol), potassium carbonate (23.4 g, 0.169 mol) and potassium 5-chloro-2-nitroaniline (150.0 g, 0.869 mol) was added to a 42% tetrafluoroboric acid aqueous solution (381.6 g, 1.825 mol), followed by cooling the mixture to 5 to 10° C., and then spending two hours delivering thereinto by drops a 50% sodium nitrite aqueous solution (119.7 g, 0.869 mol) at 5 to 10° C. After finishing the delivery by drops, stirring was performed for an hour, followed by adding diethyl ether thereto to filtrate the crystals, and then performing washing, thereby obtaining an intermediate 18-1.

4-tert-octylphenol (130.0 g, 0.630 mol), sodium hydroxide (26.5 g, 0.663 mol) and sodium carbonate (35.4 g, 0.334 mol) were added to and mixed with 850 mL of methanol and 450 mL of an ion-exchange water, followed by spending four hours delivering thereinto by drops, at 5 to 10° C., the intermediate 18-1 (171.0 g, 0.630 mol) dissolved in 3240 mL of an ion-exchange water. After finishing the delivery by drops, stirring was performed for an hour, followed by performing acid treatment, and then filtrating the crystals precipitated before washing the same, thereby obtaining an intermediate 18-2.

The intermediate 18-2 (75.0 g, 0.192 mol), a 2M NaOH aqueous solution (288.5 g) and a zinc powder (150.99 g) were added to 400 mL of toluene, followed by stirring them at 85° C., for two hours. After completing the reaction, filtration, washing and recrystallization were performed to obtain an intermediate 18-3.

The intermediate 18-3 (5.0 g, 0.014 mol), 4-tert-butylbenzenethiol (3.5 g, 0.021 mol), potassium carbonate (4.3 g, 0.031 mol) and potassium iodide (0.2 g, 0.001 mol) were reacted in 50 g of DMF at 125° C., for 12 hours. After completing the reaction, pH was adjusted, followed by performing filtration, MeOH washing, water washing, recrystallization and then column purification to obtain an intermediate 18-4.

The intermediate 18-4 (0.20 g, 0.410 mmol), a formalin aqueous solution (0.05 g, 0.615 mmol) and diethylamine (0.05 g, 0.697 mmol) were added to 25 mL of 1-butanol, followed by reacting them at 150° C., for 17 hours. After completing the reaction, column purification was performed to obtain an intermediate 18-5.

The intermediate 18-4 (1.00 g, 2.052 mmol), the intermediate 18-5 (1.34 g, 2.341 mmol) and a 28% sodium methylate MeOH solution (1.33 g) were added to 25 mL of xylene, followed by reacting them in an autoclave at 175° C., for 15 hours. After completing the reaction, column purification was performed to obtain a compound 18.

FT-IR (KBr): 2,953 cm$^{-1}$: O—H stretching vibration 1,460, 1,389 cm$^{-1}$: triazole ring stretching vibration 670 cm$^{-1}$: C—S stretching vibration $^1$H-NMR (CDCl$_3$ 400 MHz): δ 0.68 (s, 18H, -Ph-OH—CCH$_2$C(C$\underline{H}$$_3$)$_3$), 1.35 (s, 18H, —S-Ph-C(C$\underline{H}$$_3$)$_3$), 1.36 (s, 12H, -Ph-OH—C(C$\underline{H}$$_3$)$_2$CH$_2$C(CH$_3$)$_3$), 1.70 (s, 4H, -Ph-CC$\underline{H}$$_2$C), 4.26 (s, 2H, -Ph-OH—C$\underline{H}$$_2$—OH-Ph-), 7.34 (m, 2H), 7.37 (m, 2H), 7.43 (d, 8H), 7.63 (s, 2H), 7.80 (d, 2H), 8.02 (d, 2H), (insg.18arom. CH), 11.36 (s, 2H, -Ph-OH)

$^{13}$C-NMR (CDCl$_3$ 100 MHz): δ 30.9 (-Ph-OH—$\underline{C}$H$_2$—OH-Ph-), 31.3 (—S-Ph-C($\underline{C}$H$_3$)$_3$), 31.7 (-Ph-OH—C(C$\underline{H}$$_3$)$_2$CH$_2$C(CH$_3$)$_3$), 31.8 (-Ph-OH—C(CH$_3$)$_2$CH$_2$C($\underline{C}$H$_3$)$_3$), 32.3 (-Ph-OH—C(CH$_3$)$_2$CH$_2$$\underline{C}$(CH$_3$)$_3$), 34.7 (—S-Ph-$\underline{C}$(CH$_3$)$_3$), 38.2 (-Ph-OH—$\underline{C}$(CH$_3$)$_2$CH$_2$C(CH$_3$)$_3$), 56.6 (-Ph- OH—C(CH$_3$)$_2$$\underline{C}$H$_2$C(CH$_3$)$_3$), 115.9, 116.5, 117.9, 126.7, 129.4, 129.6, 133.0 (CH$_{arom}$), 124.4, 141.6, 143.4 (C$_{arom}$), 129.3 ($\underline{C}$$_{arom}$—CH$_2$), 129.9 ($\underline{C}$$_{arom}$—S), 138.1 (S—$\underline{C}$$_{arom}$), 141.4 (C$_{arom}$—C(CH$_3$)$_3$), 145.6 ($\underline{C}$$_{arom}$—OH), 151.8 ($\underline{C}$$_{arom}$—C(CH$_3$)$_2$)

<Synthesis Example 19> Synthesis of Compound 19

[Chemical formula 36]

2-(2-hydroxy-3-tert-butyl-5-methylphenyl)-5-chlorobenzotriazole (50.0 g, 0.158 mol), octanethiol (46.3 g, 0.316 mol), potassium carbonate (48.1 g, 0.348 mol) and potassium iodide (1.8 g, 0.011 mol) were reacted in 125 g of DMF at 125° C., for 12 hours. After completing the reaction, pH was adjusted, followed by performing filtration, MeOH washing, water washing and then recrystallization to obtain a compound 19.

FT-IR (KBr): 2,956 cm$^{-1}$: O—H stretching vibration 1,445, 1,392 cm$^{-1}$: triazole ring stretching vibration 662 cm$^{-1}$: C—S stretching vibration $^1$H-NMR (CDCl$_3$ 400 MHz): δ 0.89 (1, 3H, C$\underline{H}$$_3$ (CH$_2$)$_7$—S), 1.33 (m, 8H, CH$_3$(C$\underline{H}$$_2$)$_4$ (CH$_2$)$_3$—S), 1.49 (m, 11H, -Ph-OH—CH$_3$—C(C$\underline{H}$$_3$)$_3$, CH$_3$(CH$_2$)$_4$C$\underline{H}$$_2$ (CH$_2$)$_2$—S), 1.73 (quin, 2H, CH$_3$(CH$_2$)$_5$C$\underline{H}$$_2$CH$_2$—S), 2.38 (s, 3H, -Ph-OH—C$\underline{H}$$_3$—C(CH$_3$)$_3$), 3.02 (t, 2H, CH$_3$(CH$_2$)$_5$ CH$_2$C$\underline{H}$$_2$—S), 7.16 (s, 1H), 7.36 (d, 1H), 7.69 (s, 1H), 7.78 (d, 1H), 8.04 (s, 1H), (insg.5arom. C$\underline{H}$), 11.62 (s, 1H, -Ph-O$\underline{H}$—CH$_3$—C(CH$_3$)$_3$)

$^{13}$C-NMR (CDCl$_3$ 100 MHz): δ 14.0 ($\underline{C}$H$_3$(CH$_2$)$_7$—S), 20.9 (-Ph-OH—$\underline{C}$H$_3$—C(CH$_3$)$_3$), 22.6 (CH$_3$$\underline{C}$H$_2$(CH$_2$)$_5$ CH$_2$—S), 28.7 (CH$_3$CH$_2$($\underline{C}$H$_2$)$_4$CH$_2$CH$_2$—S), 29.5 (-Ph-OH—CH$_3$—C($\underline{C}$H$_3$)$_3$), 31.8 (-Ph-OH—CH$_3$—$\underline{C}$(CH$_3$)$_3$), 33.8 (CH$_3$(CH$_2$)$_5$$\underline{C}$H$_2$CH$_2$—S), 35.4 (CH$_3$(CH$_2$)$_5$ CH$_2$$\underline{C}$H$_2$—S), 113.6, 117.5, 119.3, 128.7, 129.2 ($\underline{C}$H$_{arom}$), 125.4, 141.2, 143.4 ($\underline{C}$$_{arom}$), 128.3 ($\underline{C}$$_{arom}$—CH$_3$), 138.0 ($\underline{C}$$_{arom}$—S), 139.1 ($\underline{C}$$_{arom}$—C(CH$_3$)$_3$), 146.7 ($\underline{C}$$_{arom}$—OH)

<Synthesis Example 20> Synthesis of Compound 20

[Chemical formula 37]

2-(2-hydroxy-3-tert-butyl-5-methylphenyl)-5-chlorobenzotriazole (20.0 g, 63.3 mmol), benzyl mercaptan (15.7 g, 126.6 mmol), potassium carbonate (19.3 g, 139.4 mmol) and potassium iodide (0.74 g, 4.5 mmol) were reacted in 50.0 g of DMF at 125° C., for 12 hours. After completing the reaction, pH was adjusted, followed by performing filtration, MeOH washing, water washing and then recrystallization to obtain a compound 20.

FT-IR (KBr): 2,960 cm$^{-1}$: O—H stretching vibration 1,441, 1,392 cm$^{-1}$: triazole ring stretching vibration 664 cm$^{-1}$: C—S stretching vibration $^1$H-NMR (CDCl$_3$ 400 MHz): δ 1.49 (s, 9H, -Ph-OH—CH$_3$—C(C$\underline{H}$$_3$)$_3$), 2.38 (s, 3H, -Ph-OH—C$\underline{H}$$_3$—C(CH$_3$)$_3$), 4.24 (s, 2H, Ph-C$\underline{H}$$_2$—S—), 7.16 (s, 1H), 7.26-7.38 (m, 6H), 7.72 (s, 1H), 7.80 (d, 1H), 8.04 (d, 1H), (insg.10arom. CH), 11.58 (s, 1H, -Ph-O$\underline{H}$—CH$_3$—C(CH$_3$)$_3$)

$^{13}$C-NMR (CDC) 100 MHz): δ 20.9 (-Ph-OH—$\underline{C}$H$_3$—C (CH$_3$)$_3$), 29.5 (-Ph-OH—CH$_3$—C($\underline{C}$H$_3$)$_3$), 35.4 (-Ph-OH—CH$_3$—$\underline{C}$(CH$_3$)$_3$), 38.6 (Ph-$\underline{C}$H$_2$—S—), 115.4, 117.6, 119.3, 128.7, 128.8, 128.8, 129.7, 137.0 (CH$_{arom}$), 125.4, 141.4, 143.4 ($\underline{C}$$_{arom}$), 128.3 ($\underline{C}$$_{arom}$—CH$_3$), 136.5 ($\underline{C}$$_{arom}$ CH$_2$—S—), 138.7 (S—$\underline{C}$$_{arom}$), 139.1 ($\underline{C}$$_{arom}$—C(CH$_3$)$_3$), 146.7 ($\underline{C}$$_{arom}$—OH)

<Synthesis Example 21> Synthesis of Compound
21

Further, a molar extinction coefficient was calculated by
the following formula (Table 4), after reading the absor-

[Chemical formula 38]

2-(2-hydroxy-3-tert-butyl-5-methylphenyl)-5-chloroben-
zotriazole (10.0 g, 31.7 mmol), hexanedithiol (4.76 g, 31.7
mmol), potassium carbonate (8.75 g, 63.3 mmol) and potas-
sium iodide (0.37 g, 2.2 mmol) were reacted in 50 g of DMF
at 130° C., for 12 hours. After completing the reaction, pH
was adjusted, followed by performing filtration, MeOH
washing, water washing, recrystallization and then column
purification to obtain a compound 21.

FT-IR (KBr): 3,009 cm$^{-1}$: O—H stretching vibration
1,431, 1,391 cm$^{-1}$: triazole ring stretching vibration 656
cm$^{-1}$: C—S stretching vibration $^{1}$H-NMR (CDCl$_3$ 400 MHz): δ 1.49 (s, 18H, -Ph-OH—
CH$_3$—C(CH$_3$)$_3$),        1.55        (m,        4H,
—S—CH$_2$CH$_2$CH$_2$CH$_2$CH$_2$CH$_2$—S—),  1.77  (m,  4H,
—S—CH$_2$CH$_2$CH$_2$CH$_2$CH$_2$CH$_2$—S—), 2.38 (s, 6H, (-Ph-
OH—CH$_3$—C(CH$_3$)$_3$),        3.04        (t,        4H,
—S—CH$_2$CH$_2$CH$_2$CH$_2$CH$_2$CH$_2$—S—), 7.16 (s, 2H), 7.37
(d, 2H), 7.70 (s, 2H), 7.81 (d, 2H), 8.05 (s, 2H)
(insg.10arom. CH), 11.60 (s, 2H, -Ph-OH—CH$_3$—C(CH$_3$)$_3$)

$^{13}$C-NMR (CDCl$_3$ 100 MHz): δ 20.9 (-Ph-OH—CH$_3$—
C(CH$_3$)$_3$), 28.4 (-Ph-OH—CH$_3$—C(CH$_3$)$_3$), 28.6 (—S—
CH$_2$CH$_2$CH$_2$CH$_2$CH$_2$CH$_2$—S—), 29.5 (-Ph-OH—CH$_3$—C
(CH$_3$)$_3$),  33.1  (—S—CH$_2$CH$_2$CH$_2$CH$_2$CH$_2$CH$_2$—S—),
35.4 (—S—CH$_2$CH$_2$CH$_2$CH$_2$CH$_2$CH$_2$—S—), 113.7, 117.6,
119.3, 128.3, 129.3 (CH$_{arom}$), 141.2, 143.4 (C$_{arom}$), 125.4
(C$_{arom}$—N), 128.3 (C$_{arom}$—CH$_3$), 137.7 (C$_{arom}$—S), 139.1
(C$_{arom}$—C(CH$_3$)$_3$), 146.7 (C$_{arom}$—OH)

1. Evaluation of Optical Property of Ultraviolet Absorber
and Light Resistance of Organic Resin Composition Con-
taining Ultraviolet Absorber <1> Optical Property of Ultraviolet Absorber Compounds 1 to 12, 16, 17 and 19 as the ultraviolet
absorbers were each dissolved in chloroform at 100 μM, and
compounds 13 to 15, 18, 21 and 22 were each dissolved in
chloroform at 50 μM, followed by housing each in a 10 mm
quartz cell, and then using an ultraviolet and visible spec-
trophotometer (V-550 by JASCO Corporation) to measure
an absorption spectrum thereof (FIGS. 1 to 4).

The absolute value of the gradient of an absorption peak
in a wavelength region of 350 to 390 nm on the long-
wavelength side was obtained by the following formula
(Table 3), with a point of intersection between the absorption
spectrum of the absorption peak of each compound on the
long-wavelength side and a baseline (line at which the
gradient of an absorption spectrum in 400 to 500 nm is 0)
serving as a peak end (e.g. FIG. 1).

|Gradient of absorption peak in wavelength region of
350 to 390 nm on long-wavelength side|=|(Ab-
sorbance at peak end−Absorbance at absorption
peak in wavelength region of 350 to 390 nm)/
(Absorption wavelength at peak end−Wave-
length at absorption peak in wavelength region
of 350 to 390 nm)| bance at the absorption peak (maximum absorption wave-
length: λmax) in the wavelength region of 350 to 390 nm Molar extinction coefficient: εmax (L/(mol·cm)=A:
Absorbance/[c: Molar concentration (mol/L)×1:
Cell optical path length (cm)]

Since each of the compounds 1 to 18 has a thioaryl ring
group or a thiocyclohexyl ring group, as compared to
2-(2-hydroxy-3-t-butyl-5-methylphenyl)-chlorobenzotriaz-
ole (absorption peak: 353.5 nm, gradient: 0.0219) as a
general  long-wavelength  absorption-type  ultraviolet
absorber, and as compared to a comparative example 1
(compound 22, TINUVIN360 by Ciba Specialty Chemi-
cals), these compounds each have an absorption peak of a
maximum absorption wavelength in 360 to 375 nm, thus
being superior in ultraviolet absorption ability in the long-
wavelength region, and the absolute value of the gradient of
the absorption peak of each of these compounds on the
long-wavelength side is not smaller than 0.030; particularly,
the gradients of the compounds 1, 2, 3, 6, 8, 10, 11, 12 and
13 were all not smaller than 0.040, and the gradients of the
compounds 2, 3, 6, 8 and 12 were all not smaller than 0.042,
which indicated that a high yellowing suppression effect can
be achieved with regard to films and transparent members.

As for molar extinction coefficient, the compounds 1 to
12, 16 and 17 of the formulae (1) and (2) each exhibited a
value of not smaller than 20.000 L/(mol·cm); it was con-
firmed that an ultraviolet in the long-wavelength region can
be absorbed with the usage of a smaller amount and more
efficiently as compared to 2-(2-hydroxy-3-t-butyl-5-meth-
ylphenyl)-chlorobenzotriazole (15.300 L/(mol·cm)). Par-
ticularly, the compounds 13 to 15 and 18 of the formulae (3)
and (4) each having two 2-phenylbenzotriazole skeletons, all
exhibited a value of not smaller than 40,000 L/(mol·cm),
thus being superior in their effects as compared to a thioaryl
ring-free comparative example 22 (33.700 L/(mol·cm))

Further, as can be seen from the absorption spectra shown
in FIGS. 1 to 4, the ultraviolet absorbers of the compounds
1 to 15, 17 and 18 of the formulae (1), (3) and (4), as a result
of introducing a phenyl ring residue or naphthyl ring residue
into the thioaryl ring group, holistically exhibited larger
absorption peaks (larger absorbances) in a region of 250 to
330 nm as compared to compounds 19 and 21 of reference
examples; it was indicated that these ultraviolet absorbers
were capable of absorbing a wide range of ultraviolet rays
from a low-wavelength ultraviolet to a long-wavelength
ultraviolet, thereby bringing about a high effect(s) of, for
example, suppressing a quality deterioration of a member as
well as the ultraviolet absorber, and preventing health prob-
lems.

<2> Production of Sample for Light Resistance Evaluation of Ultraviolet Absorber (Ultraviolet Absorber-Containing Organic Resin Composition)

Each of the compounds 1 to 16 and 19 to 21 was dissolved in a 20 wt % acrylic resin (PARALOID B72) toluene solution at the following mass ratios while taking the solubility of the compound into consideration, followed by applying the solution to a soda glass, and then performing drying at 80° C., for 10 min so as to obtain an evaluation sample.

Compounds 1 to 6, 8 to 11, 16, 19 and 20
    Compounding ratio (mass ratio)
        20 wt % acrylic resin toluene solution:compound=3.0:0.1
        (acrylic resin:compound=0.6:0.1)
    Dry film thickness: 2 to 3 μm
Compounds 7 and 12
    Compounding ratio (mass ratio)
        20 wt % acrylic resin toluene solution:compound=6.0:0.1
        (acrylic resin:compound=1.2:0.1)
    Dry film thickness: 4 to 6 μm
Compound 13
    Compounding ratio (mass ratio)
        20 wt % acrylic resin toluene solution:compound=12.0:0.1
        (acrylic resin:compound=2.4:0.1)
    Dry film thickness: 7 to 9 μm
Compounds 14, 15 and 21
    Compounding ratio (mass ratio)
        20 wt % acrylic resin toluene solution:compound=17.0:0.1
        (acrylic resin:compound=3.4:0.1)
    Dry film thickness: 50 μm <3> Evaluation of Light Resistance of Ultraviolet Absorber (Ultraviolet Absorber-Containing Organic Resin Composition)

An ultraviolet and visible spectrophotometer (spectrophotometer U-3310 by Hitachi, Ltd.) was used to measure a UV-Vis transmission spectrum of the evaluation sample obtained, where initial (before-irradiation) ultraviolet transmittances ($T_1uv$: %) at 380, 390 and 400 nm were read, followed by using an ultraviolet irradiation device (Xenon weather meter X25 FL-Z by Suga Test Instruments Co., Ltd.) to perform ultraviolet irradiation under a condition(s) of wavelength 300 to 400 nm, irradiance 42 W/m², black panel temperature 63° C. After performing irradiation for an irradiation period of 70 and 140 hours, a UV-Vis transmission spectrum was measured, and transmittances ($T_2uv$: %) at 380, 390 and 400 nm originating from the ultraviolet absorber were read, followed by using the following formula to calculate a difference in transmittance ΔTuv (%) so as to evaluate the light resistance of the ultraviolet absorber (Tables 1A and 1B).

$$\text{Difference in transmittance } (\Delta Tuv) = T_1uv - T_2uv \text{ (\%).} \quad \text{[Formula 1]}$$

Smaller ΔTuvs were obtained when the light resistance was superior as a result of having no deterioration in the ultraviolet absorber as well as ultraviolet absorption capability (i.e. ultraviolet absorption capability was not impaired). The ΔTuvs obtained after the irradiation periods of 70 and 140 hours as shown in Tables 1A and 1B were evaluated based on the following criteria and were ranked with ⊚ to x (Tables 2A and 2B).
    ⊚: ΔTuv=0 to 2.0
    ○: ΔTuv=2.1 to 4.0
    Δ: ΔTuv=4.1 to 6.0
    x: ΔTuv=6.1 or larger Further, ⊚ to x were translated into scores of 0 to 3 so as to add up the scores of each compound under each irradiation period (70, 140 hours) (S (70 h), S (140 h)).
    ⊚: 3
    ○: 2
    Δ: 1
    x: 0

While S (70 h) of each of the compounds 1 to 12 (working examples 1 to 12) of the formula (1) was 1 to 9, S (70 h) was 0 in the case of the compound 19 (reference example 1) where X in the thioalkoxy group (—S—X) is not an aryl ring residue, and in the case of the compound 20 (reference example 2) where the phenyl ring residue(s) is not directly bonded to a sulfur atom. Further, likewise, while S (70 h) of each of the compounds 13 to 15 (working examples 13 to 15) of the formula (3) was 4 to 9, S (70 h) was 3 in the case of the compound 21 of the reference example 3, which indicated that the ultraviolet absorber of the present invention with the aryl ring residues ($X^{1a}$, $X^{1c}$, $X^{2c}$) being directly bonded to sulfur atoms was superior in light resistance. It is assumed that the ultraviolet absorbers of the formulae (1), (3) and (4) exhibited a high light resistance because these ultraviolet absorbers were stabilized due to a x-electron interaction between the phenyl or naphthyl ring residues of the aromatic aryl rings that are directly bonded to sulfur atoms and the 2-phenylbenzotriazole skeleton. Further, as compared to the compounds 19 to 21 of the reference examples (S (70 h): 0 to 3), the compound 16 of the formula (2) (S (70 h): 6) also exhibited a favorable light resistance.

In addition, while S (70 h) was 9 in the case of the compound 1 where $X^{1a}$ represents a phenyl ring residue, S (70 h) was 2 in the case of the compound 12 where $X^{1a}$ represents a naphthyl ring, which indicated that compounds with X representing a phenyl ring residue had favorable tendencies.

When making a comparison of $R^{1a}$, rather than a compound with $R^{1a}$ having a hydroxy group (compound 11: S (70 h)=1, S (140 h)=0)), compounds with $R^{1a}$ having an alkoxy group (compound 4: S (70 h)-8, S (140 h)-6) and a hydrocarbon group (compounds 2, 3 and 5 to 10: S (70 h)=4 to 9. S (140 h)-0 to 6) were superior in light resistance. Particularly, a high light resistance was exhibited in the case of the compound 1 where l=0, and all the substituent groups of $X^{1a}$ are hydrogen atoms (S (70 h)=9, S (140 h)=9).

Further, in the formula (1), when $X^{1a}$ was a phenyl ring residue, the following tendencies were exhibited.
    As for the compounds 2, 5, 6, 7, 8 and 10 where l=1 to 3, and where at least one of $R^{1a}$s has a branched alkyl group having 3 to 8 carbon atoms, a difference(s) in transmittance at each of the wavelengths 380, 390 and 400 nm were all not larger than 6.0 after the irradiation period of 70 hours. These compounds exhibited a light resistance higher than that of the compounds 19 and 20) (reference examples 1 and 2) having similar structures.
    As for the compounds 2, 5, 6, 7 and 9 where l=1, and where $R^{1a}$ is a linear or branched alkyl group having 1 to 18 carbon atoms, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 2, 5, 6, 7 and 9 where l=1, and where $R^{1a}$ is a linear or branched alkyl group having 1 to 10 carbon atoms, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 2, 5, 6, 7 and 9 where l=1, and where $R^{1a}$ is a linear or branched alkyl group having 1 to 8 carbon atoms, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 2, 5, 6 and 7 where l=1, and where $R^{1a}$ is a linear or branched alkyl group having 2 to 8 carbon atoms, a difference(s) in transmittance at each of the wavelengths 380, 390 and 400 nm were all not larger than 4.0 after the irradiation period of 70 hours, and a difference(s) in transmittance at two of the wavelengths 380, 390 and 400 nm were not larger than 6.0 after the irradiation period of 140 hours. These compounds exhibited a light resistance higher than that of the compound 9; and that of the compounds 19 and 20 (reference examples 1 and 2) having similar structures.

As for the compounds 2, 5, 6 and 7 where l=1, and where $R^{1a}$ is a linear or branched alkyl group having 3 to 8 carbon atoms, a difference(s) in transmittance at each of the wavelengths 380, 390 and 400 nm were all not larger than 4.0 after the irradiation period of 70 hours, and a difference(s) in transmittance at two of the wavelengths 380, 390 and 400 nm were not larger than 6.0 after the irradiation period of 140 hours. These compounds exhibited a light resistance higher than that of the compound 9; and that of the compounds 19 and 20 (reference examples 1 and 2) having similar structures.

As for the compounds 2, 5 and 6 where l=1, and where $R^{1a}$ is a linear or branched alkyl group having 3 to 5 carbon atoms, a difference(s) in transmittance at each of the wavelengths 380, 390 and 400 nm were all not larger than 4.0 after the irradiation period of 70 hours, and a difference(s) in transmittance at each of the wavelengths 380, 390 and 400 nm were all not larger than 6.0 after the irradiation period of 140 hours. These compounds exhibited a light resistance higher than that of the compounds 7 and 9; and that of the compounds 19 and 20 (reference examples 1 and 2) having similar structures.

As for the compounds 2 and 5 where l=1, and where $R^{1a}$ is a linear or branched alkyl group having 4 to 5 carbon atoms, a difference(s) in transmittance at each of the wavelengths 380, 390 and 400 nm were all not larger than 4.0 after the irradiation period of 70 hours, a difference in transmittance at one of the wavelengths 380, 390 and 400 nm was not larger than 6.0 after the irradiation period of 140 hours, and a difference(s) in transmittance at two of the wavelengths 380, 390 and 400 nm were not larger than 4.0 after the irradiation period of 140 hours. These compounds exhibited a light resistance higher than that of the compounds 6, 7 and 9; and that of the compounds 19 and 20 (reference examples 1 and 2) having similar structures.

As for the compound 2 where l=1, and where $R^{1a}$ is a linear or branched alkyl group having 4 carbon atoms, a difference(s) in transmittance at each of the wavelengths 380, 390 and 400 nm were all not larger than 2.0 after the irradiation period of 70 hours, and a difference(s) in transmittance at each of the wavelengths 380, 390 and 400 nm were all not larger than 4.0 after the irradiation period of 140 hours. This compound exhibited a light resistance higher than that of the compounds 5, 6, 7 and 9; and that of the compounds 19 and 20 (reference examples 1 and 2) having similar structures.

Further, as for the compounds 2, 5, 6 and 7 where l=1, and where $R^{1a}$ is a tertiary and/or quaternary carbon-containing alkyl group, a difference(s) in transmittance at each of the wavelengths 380, 390 and 400 nm were all not larger than 4.0 after the irradiation period of 70 hours. These compounds exhibited a light resistance higher than that of the compound 9; and that of the compounds 19 and 20 (reference examples 1 and 2) having similar structures.

As for the compounds 3, 8 and 10 where l=2, and where $R^{1a}$ is a linear or branched alkyl group each having 1 to 18 carbon atoms, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 3, 8 and 10 where l=2, and where $R^{1a}$ is a linear or branched alkyl group each having 1 to 10 carbon atoms, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 3, 8 and 10 where l=2, and where $R^{1a}$ is a linear or branched alkyl group each having 1 to 5 carbon atoms, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 3 and 8 where l=2, and where $R^{1a}$ is a linear or branched alkyl group each having 1 to 4 carbon atoms, a difference(s) in transmittance at each of the wavelengths 380, 390 and 400 nm were all not larger than 4.0 after the irradiation period of 70 hours. These compounds exhibited a light resistance higher than that of the compound 10; and that of the compounds 19 and 20 (reference examples 1 and 2) having similar structures.

As for the compound 3 where l=2, and where $R^{1a}$ is a linear or branched alkyl group each having 1 carbon atom, a difference(s) in transmittance at each of the wavelengths 380, 390 and 400 nm were all not larger than 2.0 after the irradiation period of 70 hours. This compound exhibited a light resistance higher than that of the compounds 8 and 10; and that of the compounds 19 and 20 (reference examples 1 and 2) having similar structures.

As for the compounds 3, 8 and 10 where l=2, where $R^{1a}$ is a linear or branched alkyl group, and where a total number of the carbon atoms in the alkyl groups is 2 to 12, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 3, 8 and 10 where l=2, where $R^{1a}$ is a linear or branched alkyl group, and where a total number of the carbon atoms in the alkyl groups is 2 to 10, a difference(s) in transmittance at each of the wavelengths 380, 390 and 400 nm were all not larger than 6.0 after the irradiation period of 70 hours. These compounds exhibited a light resistance higher than that of the compounds 19 and 20 (reference examples 1 and 2) having similar structures.

As for the compounds 3 and 8 where l=2, where $R^{1a}$ is a linear or branched alkyl group, and where a total number of the carbon atoms in the alkyl groups is 2 to 5, a difference(s) in transmittance at each of the wavelengths 380, 390 and 400 nm were all not larger than 4.0 after the irradiation period of 70 hours. These compounds exhibited a light resistance higher than that of the compound 10; and that of the compounds 19 and 20 (reference examples 1 and 2) having similar structures.

As for the compound 3 where l=2, where $R^{1a}$ is a linear or branched alkyl group, and where a total number of the carbon atoms in the alkyl groups is 2, a difference(s) in transmittance at each of the wavelengths 380, 390 and 400 nm were all not larger than 2.0 after the irradiation period of 70 hours. This compound exhibited a light resistance higher than that of the compounds 8 and 10; and that of the compounds 19 and 20 (reference examples 1 and 2) having similar structures.

The compound of the formula (3) exhibited the following tendencies.

As for the compound 13 where q=1, and where $A^{2c}$ is a sulfide group, a difference(s) in transmittance at each of the wavelengths 380, 390 and 400 nm were all not larger than 2.0 after the irradiation period of 70 hours. This compound exhibited a light resistance higher than that of the compounds 15 and 21 (reference example 3) having similar structures.

As for the compound 14 where q=1, and where $A^{2c}$ is a hydrocarbon group having 1 to 8 carbon atoms, a difference(s) in transmittance at each of the wavelengths 380, 390 and 400 nm were all not larger than 2.0 after the irradiation period of 70 hours, and a difference(s) in transmittance at each of the wavelengths 380, 390 and 400 nm were all not larger than 4.0 after the irradiation period of 140 hours. This compound exhibited a light resistance higher than that of the compounds 13, 15 and 21 (reference example 3) having similar structures.

As for the compound 15 where q=0, a difference(s) in transmittance at each of the wavelengths 380, 390 and 400 nm were all not larger than 6.0 after the irradiation period of 70 hours. This compound exhibited a light resistance higher than that of the compound 21 (reference example 3) having a similar structure.

The ultraviolet absorber of the present invention suppresses an organic resin from deteriorating as a result of being exposed to ultraviolet rays; it was indicated that due to the excellent light resistance of the ultraviolet absorber, an organic resin composition containing such ultraviolet absorber is likewise able to absorb long-wavelength ultra-violet rays for a long period of time starting from the initial period while suppressing yellowing and deterioration.

2. Melting Point Evaluation of Ultraviolet Absorber

The melting points of the compounds 1 to 21 were measured using a differential scanning calorimeter (DSC 6220 by Seiko Instruments Inc.), where DSC peak top temperatures were taken as melting points (Tables 1A and 1B). Further, the melting point of the compound 17 was 114° C., and the melting point of the compound 18 was 176° C.

Each of the compounds 1 to 18 of the present invention exhibited a melting point of not lower than 100° C.; each of the compounds 1 to 3, 5 to 12, 14 to 16 and 18 exhibited a melting point of not lower than 130° C.; each of the compounds 2, 5 to 9, 11, 12, 14 to 16 and 18 exhibited a melting point of not lower than 140° C.; each of the compounds 2, 6 to 8, 11, 12, 14, 15 and 18 exhibited a melting point of not lower than 145° C. Particularly, each of the compounds 2, 11, 12, 14, 15 and 18 exhibited a melting point of not lower than 150° C.; it was confirmed that these compounds were superior in bleed-out suppression, blocking suppression, dispersibility and heat processability.

The following tendencies were confirmed. That is, as for the compounds 2, 5, 6, 7 and 9 (melting point 140 to 155° C.) where in the formula (1), l=1, and a hydrocarbon group (alkyl group) as $R^{1a}$ is in the para position with respect to the —S— bond in the thioalkoxy group, the melting points of these compounds were higher than that of the compound 1 (melting point 136° C.) in which all the $R^{1a}$s are hydrogen atoms; and that of the compound 4 (melting point 115° C.) in which $R^{1a}$ is an alkoxy group. Even among these compounds, the compounds 2, 5, 6 and 7 (melting point 141 to 155° C.) in which the alkyl group has 3 to 8 carbon atoms exhibited melting points higher than that of the compound 9 (melting point 140° C.) in which the alkyl group has 1 carbon atom. Particularly, the compounds 2 and 6 (melting point 148 to 155° C.) in which the alkyl group has 3 to 4 carbon atoms exhibited melting points higher than those of the compounds 5, 7 and 9 (melting points 141, 146 and 140° C.) in which the alkyl group has 1, 5 and 8 carbon atoms. Especially, the compound 2 in which the alkyl group has 4 carbon atoms exhibited a high melting point.

There were also observed the following tendencies. That is, the compounds 1 to 12 of the formula (1) in which the thioaryl ring group has been introduced have melting points higher than that of the compound 19 having the thioalkyl group; the compounds 14 and 15 of the formula (3) in which $A^{1c}$ has been introduced, q=0 and q=1, and $A^{2c}$ is a hydrocarbon group have melting points higher than that of the compound 21 where $A^{1c}$ is an alkylene group.

Further, as compared to the compounds 2, 3 and 5 to 10 (melting point 131 to 155° C.) where l=1 or 2, and where $R^{1a}$ is a hydrocarbon group, to the compound 1 (melting point 136° C.) where all the $R^{1a}$s are hydrogen atoms and to the compound 4 (melting point 115° C.) where $R^{1a}$ is an alkoxy group, the compounds 11 (melting point 208° C.), 14 (melting point 196° C.) and 15 (melting point 236° C.) where $R^{1a}$ is a hydroxy group, and the compounds 12 (melting point 161° C.) and 18 (melting point 176° C.) where $X^{1a}$ is a naphthyl group had higher melting points and are thus particularly highly useful in terms of bleed-out suppression and processability. In addition, as disclosed in Patent document 2 (WO2016/021664), the compound 11, when a hydroxyl group as a reactive functional group is present at $R^{1a}$, and when a functional group(s) reactive with such hydroxyl group is present in a polymer as a resin raw material, is capable of reacting with the polymer and being immobilized to the resin, thereby making it possible to suppress a time-course bleed-out.

TABLE 1A

| | | Structure | Melting point (° C.) | Wavelength observed (nm) | $T_1uv$ (%) | $\triangle Tuv$ (%) 70 h | $\triangle Tuv$ (%) 140 h |
|---|---|---|---|---|---|---|---|
| Working example 1 | Compound 1 | | 136 | 400 | 52.10 | 1.2 | 1.6 |
| | | | | 390 | 19.88 | 1.4 | 1.6 |
| | | | | 380 | 9.85 | 1.1 | 1.0 |
| Working example 2 | Compound 2 | | 155 | 400 | 47.50 | 1.6 | 3.0 |
| | | | | 390 | 18.79 | 1.7 | 3.2 |
| | | | | 380 | 10.19 | 1.0 | 2.3 |
| Working example 3 | Compound 3 | | 132 | 400 | 49.24 | 2.0 | 3.7 |
| | | | | 390 | 16.38 | 1.9 | 4.2 |
| | | | | 380 | 8.54 | 1.2 | 2.9 |
| Working example 4 | Compound 4 | | 115 | 400 | 58.94 | 1.6 | 2.3 |
| | | | | 390 | 28.87 | 2.4 | 3.2 |
| | | | | 380 | 17.20 | 1.9 | 2.3 |
| Working example 5 | Compound 5 | | 141 | 400 | 56.87 | 1.8 | 4.0 |
| | | | | 390 | 28.33 | 2.1 | 5.1 |
| | | | | 380 | 17.86 | 1.4 | 3.8 |
| Working example 6 | Compound 6 | | 148 | 400 | 56.95 | 1.8 | 4.4 |
| | | | | 390 | 28.26 | 2.3 | 5.8 |
| | | | | 380 | 17.88 | 1.8 | 4.8 |
| Working example 7 | Compound 7 | | 146 | 400 | 59.31 | 1.8 | 5.0 |
| | | | | 390 | 22.71 | 2.3 | 6.4 |
| | | | | 380 | 12.61 | 1.6 | 4.6 |

TABLE 1A-continued

| | | Structure | Mel-ting point (° C.) | Wave-length observed (nm) | $T_1$uv (%) | $\triangle$Tuv (%) | |
|---|---|---|---|---|---|---|---|
| | | | | | | 70 h | 140 h |
| Working example 8 | Com-pound 8 | | 147 | 400 | 52.51 | 2.7 | 4.7 |
| | | | | 390 | 19.27 | 2.6 | 5.6 |
| | | | | 380 | 10.64 | 1.9 | 4.0 |
| Working example 9 | Com-pound 9 | | 140 | 400 | 52.20 | 3.9 | 4.7 |
| | | | | 390 | 22.42 | 5.1 | 10.3 |
| | | | | 380 | 13.10 | 4.2 | 10.3 |
| Working example 10 | Com-pound 10 | | 131 | 400 | 39.73 | 4.6 | 14.1 |
| | | | | 390 | 17.93 | 4.6 | 14.0 |
| | | | | 380 | 12.07 | 3.7 | 11.6 |

TABLE 1B

| Working example | Compound | Structure | Melting point (° C.) | Wavelength observed (nm) | T₁uv (%) | ΔTuv (%) 70 h | ΔTuv (%) 140 h |
|---|---|---|---|---|---|---|---|
| Working example 11 | Compound 11 | *(chemical structure)* | 208 | 400 / 390 / 380 | 38.10 / 11.54 / 5.69 | 7.0 / 6.3 / 4.1 | 20.7 / 23.9 / 17.5 |
| Working example 12 | Compound 12 | *(chemical structure)* | 161 | 400 / 390 / 380 | 43.55 / 16.19 / 8.38 | 5.7 / 6.1 / 4.3 | 18.9 / 25.0 / 20.2 |
| Working example 13 | Compound 13 | *(chemical structure)* | 118 | 400 / 390 / 380 | 44.37 / 22.01 / 12.92 | 1.3 / 1.1 / 0.7 | 13.2 / 13.2 / 10.2 |
| Working example 14 | Compound 14 | *(chemical structure)* | 196 | 400 / 390 / 380 | 41.26 / 11.47 / 4.53 | 1.7 / 1.1 / 0.6 | 3.1 / 2.5 / 1.3 |
| Working example 15 | Compound 15 | *(chemical structure)* | 236 | 400 / 390 / 380 | 33.24 / 22.74 / 16.71 | 4.1 / 4.3 / 3.6 | 27.1 / 26.4 / 23.2 |

TABLE 1B-continued

| | | | Structure | Melting point (° C.) | Wavelength observed (nm) | $T_1$uv (%) | $\Delta$Tuv (%) 70 h | $\Delta$Tuv (%) 140 h |
|---|---|---|---|---|---|---|---|---|
| Working example 16 | Compound 16 | | | 141 | 400<br>390<br>380 | 54.59<br>22.59<br>12.83 | 2.8<br>3.2<br>2.5 | 5.4<br>6.3<br>4.9 |
| Reference example 1 | Compound 19 | | | 67 | 400<br>390<br>380 | 59.45<br>25.70<br>16.55 | 6.1<br>20.8<br>17.9 | 21.7<br>48.5<br>48.8 |
| Reference example 2 | Compound 20 | | | 130 | 400<br>390<br>380 | 58.91<br>23.25<br>12.80 | 13.7<br>38.0<br>37.5 | 23.5<br>52.2<br>53.8 |
| Reference example 3 | Compound 21 | | | 190 | 400<br>390<br>380 | 61.22<br>37.06<br>29.19 | 2.6<br>6.1<br>5.6 | 3.0<br>10.4<br>9.7 |

TABLE 2A

| | Structure | ΔTuv (%) | | | |
| --- | --- | --- | --- | --- | --- |
| | | 70 h | | 140 h | |
| | | S(70 h) | | S(140 h) | |
| Working example 1 | Compound 1 | ◎ ◎ ◎ | 9 | ◎ ◎ ◎ | 9 |
| Working example 2 | Compound 2 | ◎ ◎ ◎ | 9 | ○ ○ ○ | 6 |
| Working example 3 | Compound 3 | ◎ ◎ ◎ | 9 | ○ △ ○ | 5 |
| Working example 4 | Compound 4 | ◎ ○ ◎ | 8 | ○ ○ ○ | 6 |
| Working example 5 | Compound 5 | ◎ ○ ◎ | 8 | ○ △ ○ | 5 |
| Working example 6 | Compound 6 | ◎ ○ ◎ | 8 | △ △ △ | 3 |
| Working example 7 | Compound 7 | ◎ ○ ◎ | 8 | △ x △ | 2 |

TABLE 2A-continued

| | | Structure | $\Delta$Tuv (%) 70 h S(70 h) | | 140 h S(140 h) | |
|---|---|---|---|---|---|---|
| Working example 8 | Compound 8 | *(chemical structure: benzotriazole with HO, t-Bu, Me, t-Bu, Me, S substituents)* | ○ ○ ⊚ | 7 | △ △ ○ | 4 |
| Working example 9 | Compound 9 | *(chemical structure: benzotriazole with HO, t-Bu, Me, Me, S substituents)* | ○ △ △ | 4 | △ x x | 1 |
| Working example 10 | Compound 10 | *(chemical structure: benzotriazole with HO, t-Bu, Me, $C_2H_5$, $CH_3$, $CH_3$, $CH_3$, $C_2H_5$, S substituents)* | △ △ ○ | 4 | x x x | 0 |

TABLE 2B

| | | Structure | $\Delta$Tuv (%) 70 h S(70 h) | | 140 h S(140 h) | |
|---|---|---|---|---|---|---|
| Working example 11 | Compound 11 | *(chemical structure: benzotriazole with HO, t-Bu, Me, HO, S substituents)* | x x △ | 1 | x x x | 0 |
| Working example 12 | Compound 12 | *(chemical structure: benzotriazole with HO, t-Bu, Me, naphthyl, S substituents)* | △ x △ | 2 | x x x | 0 |
| Working example 13 | Compound 13 | *(chemical structure: bis-benzotriazole with t-Bu, OH, Me, S, S, S, HO, t-Bu, Me substituents)* | ⊚ ⊚ ⊚ | 9 | x x x | 0 |

TABLE 2B-continued

| | | Structure | $\angle$Tuv (%) | | | |
|---|---|---|---|---|---|---|
| | | | 70 h | | 140 h | |
| | | | | S(70 h) | | S(140 h) |
| Working example 14 | Compound 14 | t-Bu, OH ... HO, t-Bu (structure) | ◎ ◎ ◎ | 9 | ○ ○ ◎ | 7 |
| Working example 15 | Compound 15 | t-Bu, OH ... HO, t-Bu (structure) | △ △ ○ | 4 | x x x | 0 |
| Working example 16 | Compound 16 | HO, t-Bu (structure) | ○ ○ ○ | 6 | △ x △ | 2 |
| Reference example 1 | Compound 19 | HO, t-Bu (structure) CH3(CH2)7S | x x x | 0 | x x x | 0 |
| Reference example 2 | Compound 20 | HO, t-Bu (structure) CH2—S | x x x | 0 | x x x | 0 |
| Reference example 3 | Compound 21 | t-Bu, OH ... HO, t-Bu (structure) S—(CH2)6—S | ○ x △ | 3 | ○ x x | 2 |

TABLE 3

| | | Wavelength (nm) at absorption peak in wavelength region of 350 to 390 nm (maximum absorption wavelength: λ max) | Light absorbance at absorption peak in wavelength region of 350 to 390 nm | Absorption wavelength at peak end (nm) | Light absorbance at peak end | Absolute value of gradient of absorption peak in wavelength region of 350 to 390 nm on long-wavelength side |
|---|---|---|---|---|---|---|
| Working example 1 | Compound 1 | 367.5 | 2.54790 | 429.0 | 0.00053 | 0.0414 |
| Working example 2 | Compound 2 | 368.5 | 2.53410 | 427.5 | 0.00017 | 0.0429 |
| Working example 3 | Compound 3 | 369.5 | 2.53784 | 427.5 | 0.00027 | 0.0438 |
| Working example 4 | Compound 4 | 367.0 | 2.40233 | 428.0 | 0.00013 | 0.0394 |

TABLE 3-continued

| | | Wavelength (nm) at absorption peak in wavelength region of 350 to 390 nm (maximum absorption wavelength: λ max) | Light absorbance at absorption peak in wavelength region of 350 to 390 nm | Absorption wavelength at peak end (nm) | Light absorbance at peak end | Absolute value of gradient of absorption peak in wavelength region of 350 to 390 nm on long-wavelength side |
|---|---|---|---|---|---|---|
| Working example 5 | Compound 5 | 368.0 | 2.37236 | 429.0 | 0.00470 | 0.0388 |
| Working example 6 | Compound 6 | 369.0 | 2.50507 | 428.5 | 0.00011 | 0.0421 |
| Working example 7 | Compound 7 | 368.0 | 2.36473 | 429.0 | 0.00415 | 0.0387 |
| Working example 8 | Compound 8 | 369.0 | 2.58138 | 427.0 | 0.00026 | 0.0445 |
| Working example 9 | Compound 9 | 369.0 | 2.14986 | 426.5 | 0.00429 | 0.0373 |
| Working example 10 | Compound 10 | 373.5 | 2.28730 | 429.0 | 0.00899 | 0.0411 |
| Working example 11 | Compound 11 | 369.5 | 2.43674 | 429.0 | 0.00072 | 0.0409 |
| Working example 12 | Compound 12 | 370.0 | 2.51358 | 428.0 | 0.00045 | 0.0433 |
| Working example 13 | Compound 13 | 369.0 | 2.45515 | 429.0 | 0.00536 | 0.0408 |
| Working example 14 | Compound 14 | 368.0 | 2.23872 | 429.0 | 0.00418 | 0.0366 |
| Working example 15 | Compound 15 | 369.0 | 2.05831 | 429.0 | 0.00617 | 0.0342 |
| Working example 16 | Compound 16 | 367.5 | 2.10625 | 426.0 | 0.00768 | 0.0359 |
| Working example 17 | Compound 17 | 364.0 | 2.30138 | 429.0 | 0.01348 | 0.0352 |
| Working example 18 | Compound 18 | 369.5 | 2.37613 | 429.0 | 0.01237 | 0.0397 |
| Comparative example 1 | Compound 22 | 349.0 | 1.68500 | 413.0 | 0.00100 | 0.0263 |

TABLE 4

| | | Molecular weight (g/mol) | Wavelength (nm) at absorption peak in wavelength region of 350 to 390 nm (maximum absorption wavelength: λ max) | Light absorbance at absorption peak in wavelength region of 350 to 390 nm | Molar extinction coefficient at the left peak (L/(mol · cm)) (Maximum molar extinction coefficient: ε max) |
|---|---|---|---|---|---|
| Working example 1 | Compound 1 | 390 | 367.5 | 2.54790 | 25479 |
| Working example 2 | Compound 2 | 446 | 368.5 | 2.53410 | 25341 |
| Working example 3 | Compound 3 | 418 | 369.5 | 2.53784 | 25378 |

TABLE 4-continued

| | | Molecular weight (g/mol) | Wavelength (nm) at absorption peak in wavelength region of 350 to 390 nm (maximum absorption wavelength: λ max) | Light absorbance at absorption peak in wavelength region of 350 to 390 nm | Molar extinction coefficient at the left peak (L/(mol · cm)) (Maximum molar extinction coefficient: ε max) |
|---|---|---|---|---|---|
| Working example 4 | Compound 4 | 420 | 367.0 | 2.40233 | 24023 |
| Working example 5 | Compound 5 | 460 | 368.0 | 2.37236 | 23724 |
| Working example 6 | Compound 6 | 432 | 369.0 | 2.50507 | 25051 |
| Working example 7 | Compound 7 | 501 | 368.0 | 2.36473 | 23647 |
| Working example 8 | Compound 8 | 460 | 369.0 | 2.58138 | 25814 |
| Working example 9 | Compound 9 | 404 | 369.0 | 2.14986 | 21500 |
| Working example 10 | Compound 10 | 530 | 373.5 | 2.28730 | 22873 |
| Working example 11 | Compound 11 | 406 | 369.5 | 2.43674 | 24367 |
| Working example 12 | Compound 12 | 440 | 370.0 | 2.51358 | 25136 |
| Working example 13 | Compound 13 | 809 | 369.0 | 2.45515 | 49103 |
| Working example 14 | Compound 14 | 819 | 368.0 | 2.23872 | 44774 |
| Working example 15 | Compound 15 | 777 | 369.0 | 2.05831 | 41166 |
| Working example 16 | Compound 16 | 396 | 367.5 | 2.10625 | 21100 |
| Working example 17 | Compound 17 | 333 | 364.0 | 2.30138 | 23000 |
| Working example 18 | Compound 18 | 987 | 369.5 | 2.37613 | 47500 |
| Comparative example 1 | Compound 22 | 659 | 349.0 | 1.68500 | 33700 |

3. Transparency Evaluation of Organic Resin Composition Containing Ultraviolet Absorber (Compatibility Between Ultraviolet Absorber and Organic Resin)

Confirmed was a transparency of an organic resin composition owing to a compatibility of the compound(s) of the present invention to an organic resin (Table 5).

As various organic resin compositions, there were used a polymethylmethacrylate resin film (acryl) as a (meth)acryl-based resin serving as a polymer of a thermoplastic resin that contains the product of the present invention; a polyethylene terephthalate film (PET) as an ester-based resin serving as a polymer of a thermoplastic resin that contains the product of the present invention; a polycarbonate film (PC) as a poly-carbonate-based resin serving as a polymer of a thermoplastic resin that contains the product of the present invention; a polystyrene film (PS) as a styrene-based resin serving as a polymer of a thermoplastic resin that contains the product of the present invention; an acrylonitrile-butadiene-styrene copolymer film (ABS resin) as an acrylonitrile-butadiene-styrene-based copolymer serving as a copolymer of a thermoplastic resin that contains the product of the present invention; a urea-formaldehyde resin film as a urea-based resin serving as a polymer of a thermosetting resin that contains the product of the present invention; a melamine resin film as a melamine-based resin serving as a polymer of a thermosetting resin that contains the product of the present invention; an acrylic melamine resin film as an acrylic melamine-based resin serving as a copolymer of a thermosetting resin that contains the product of the present invention.

(Preparation of Polymethylmethacrylate Resin Film)

Polymethylmethacrylate resin films each having a film thickness of 100 to 150 μm and each added 3.0 wt % of each of the compounds 1, 2, 6, 9 and 17 of the working examples 19 to 23, were prepared by the following procedure.

After dissolving 0.0062 g of each of the compounds 1, 2, 6, 9 and 17 into 1.00 g of a 20 wt % polymethylmethacrylate resin toluene solution, 0.2 mL of the solution was then applied to a 1.5×1.5 cm glass slide, followed by performing drying at 80° C., for 10 min to obtain a polymethylmethacrylate resin film.

Further, a blank film for comparison was prepared by an operation similar to that described above, using 1.00 g of the 20 wt % polymethylmethacrylate resin toluene solution free of any additives.

(Preparation of Polyethylene Terephthalate PET Film)

Polyethylene terephthalate films each having a film thickness of 40 to 100 μm and each containing 3.0 wt % of each of the compounds 1, 2, 6, 9 and 17 of the working examples 19 to 23, were prepared by the following procedure.

Here, 0.2 g of polyethylene terephthalate chips and 0.0062 g of each of the compounds 1, 2, 6, 9 and 17 were kneaded at 280° C., followed by applying the kneaded product to a glass slide substrate, quickly spreading the same thereon and then performing air-cooling so as to obtain a polyethylene terephthalate film.

Further, a blank film for comparison was prepared by an operation similar to that described above without adding any additives.

(Preparation of Polycarbonate PC Film)

Polycarbonate films each having a film thickness of 100 to 200 μm and each containing 3.0 wt % of each of the compounds 1, 2, 6, 9 and 17 of the working examples 19 to 23, were prepared by the following procedure.

Here, 0.2 g of polycarbonate chips and 0.0062 g of each of the compounds 1, 2, 6, 9 and 17 were kneaded at 280° C., followed by applying the kneaded product to a glass slide substrate, quickly spreading the same thereon and then performing air-cooling so as to obtain a polycarbonate film.

Further, a blank film for comparison was prepared by an operation similar to that described above without adding any additives.

(Preparation of Polystyrene PS Film)

Polystyrene films each having a film thickness of 100 to 200 μm and each containing 3.0 wt % of each of the compounds 1, 2, 6, 9 and 17 of the working examples 19 to 23, were prepared by the following procedure.

After dissolving 0.0062 g of each of the compounds 1, 2, 6, 9 and 17 into 1.00 g of a 20 wt % polystyrene resin toluene solution, 0.2 mL of the solution was then applied to a 1.5×1.5 cm glass slide, followed by performing drying at 80° C., for 10 min to obtain a polystyrene film.

Further, a blank film for comparison was prepared by an operation similar to that described above, using 1.00 g of the 20 wt % polystyrene resin toluene solution free of any additives.

(Preparation of Acrylonitrile-Butadiene-Styrene Copolymer Film, ABS Resin)

Acrylonitrile-butadiene-styrene copolymer films each having a film thickness of 100 to 200 μm and each containing 3.0 wt % of each of the compounds 1, 2, 6, 9 and 17 of the working examples 19 to 23, were prepared by the following procedure.

After dissolving 0.0062 g of each of the compounds 1, 2, 6, 9 and 17 into 1.00 g of a 20 wt % ABS resin THF solution, 0.2 mL of the solution was then applied to a 1.5×1.5 cm glass slide, followed by performing drying at 80° C., for 10 min to obtain an acrylonitrile-butadiene-styrene copolymer film.

Further, a blank film for comparison was prepared by an operation similar to that described above, using 1.00 g of the 20 wt % ABS resin THF solution free of any additives.

(Preparation of Urea-Formaldehyde Resin Film)

Urea-formaldehyde resin films each having a film thickness of 50 to 100 μm and each containing 0.1 wt % of each of the compounds 1, 2, 6, 9 and 17 of the working examples 19 to 23, were prepared by the following procedure.

Here, 1 mL of a 37 wt % formaldehyde solution, 0.25 g of urea and 0.16 g of ammonium acetate were dissolved to produce a monomer solution. Next, 0.0007 g of each of the compounds 1, 2, 6, 9 and 17 was dissolved into 2 mL of THF, followed by uniformly mixing such THF with 1 mL of the monomer solution and then applying 0.2 mL of the mixed solution to a 1.5×1.5 cm glass slide. Next, this glass slide was put into an oven, and the temperature was raised from room temperature to 150° C., in 30 min so as to then allow the reaction to take place at 150° C., for five hours to obtain the film.

Further, a blank film for comparison was prepared by an operation similar to that described above, where no additives were added, and 0.1 mL of the monomer solution and 0.2 mL of THF were uniformly mixed together.

(Preparation of Melamine Resin Film)

Melamine resin films each having a film thickness of 10 to 50 μm and each containing 0.1 wt % of each of the compounds 1 and 2 of the working examples 19 to 23, were prepared by the following procedure.

A hexamethylol melamine solution was prepared by adding 1 g of melamine and 24.60 g of water to 5.15 g of a formaldehyde solution whose pH level had been adjusted to 7.5 with sodium hydroxide. Next, 0.0019 g of each of the compounds 1, 2, 6, 9 and 17 was dissolved into 1 mL of THF, followed by uniformly mixing such THF with 2 mL of the hexamethylol melamine solution and then applying 0.2 mL of the mixed solution to a 1.5×1.5 cm glass slide. Next, this glass slide was put into an oven, and the temperature was raised from room temperature to 150° C., in 30 min so as to then allow the reaction to take place at 150° C., for five hours before obtaining the film.

Further, a blank film for comparison was prepared by an operation similar to that described above, where no additives were added, and 0.2 mL of the monomer solution and 0.1 mL of THF were uniformly mixed together.

(Preparation of Acrylic Melamine Resin Film)

Acrylic melamine resin films each having a film thickness of 100 to 150 μm and each containing 3.0 wt % of each of the compounds 1, 2, 6, 9 and 17 of the working examples 19 to 23, were prepared by the following procedure.

Here, 0.0020 g of each of the compounds in the working examples 1, 2, 6, 9 and 17 was dissolved into 0.1 mL of THF, followed by uniformly performing mixing with 0.1 g (active ingredient 65%) of a bake-drying type topcoating material (bake-drying type topcoat (acrylic melamine monomer): ACRYCITE UB-63 CLEAR by Saito Paint Co., Ltd.), and then applying 0.2 mL of the mixed solution to a 1.5×1.5 cm glass slide. Next, this glass slide was put into an oven, and the temperature was raised from room temperature to 150° C., in 30 min so as to then allow the reaction to take place at 150° C., for two hours to obtain the film.

Further, a blank film for comparison was prepared by an operation similar to that described above, where no additives were added, and 0.1 g of the acrylic melamine monomer and 0.1 mL of THF were uniformly mixed together.

(Appearance)

The appearances of the films were observed visually and evaluated based on the following criteria.

Evaluation Criteria (Polymethylmethacrylate Resin Film, PS Film, ABS Resin Film)

o: Transparent as blank film for comparison x: White turbidity observed as compared to blank film for comparison Evaluation Criteria (PET Film, PC Film)

o: Transparent as blank film for comparison x: Cloudiness observed as compared to blank film for comparison Evaluation Criteria (Urea-Formaldehyde Resin Film, Melamine Resin Film, Acrylic Melamine Resin Film)

o: Transparent as blank film for comparison x: Crystal precipitation observed as compared to blank film for comparison As can be seen from Table 5, it was confirmed that the compound(s) of the present invention has a favorable compatibility with any of the resins, and a transparent organic resin composition can be obtained thereby.

TABLE 5

| | Structure | (Meth) acryl-based resin (Polymethyl-methacrylate resin) Additive concentration: 3.0 wt % | | Ester-based resin (PET: Polyethylene terephthalate) Additive concentration: 3.0 wt % | | Polycarbonate-based resin (PC: Polycarbonate) Additive concentration: 3.0 wt % | | Styrene-based resin (PS: Polystyrene) Additive concentration: 3.0 wt % | |
|---|---|---|---|---|---|---|---|---|---|
| | | Appearance | Film thickness (μm) | Appearance | Film thickness (μm) | Appearance | Film thickness (μm) | Film thickness (μm) | Appearance |
| Working example 19 | Compound 1 | ○ | 141 | ○ | 60 | ○ | 187 | ○ |
| Working example 20 | Compound 2 | ○ | 145 | ○ | 49 | ○ | 156 | ○ |
| Working example 21 | Compound 6 | ○ | 140 | ○ | 56 | ○ | 112 | ○ |
| Working example 22 | Compound 9 | ○ | 150 | ○ | 50 | ○ | 111 | ○ |

TABLE 5-continued

Working example 17 / Compound 23

Compound 23 structure: 2H-benzotriazole bearing a 2-(2-hydroxy-5-methylphenyl) group (HO, Me) and a phenylthio (S–C₆H₅) substituent.

| Working example | Film thickness (μm) | Acrylonitrile-butadiene-styrene-based copolymer (ABS resin: acrylonitrile-butadiene-styrene copolymer) Additive concentration: 3.0 wt % — Appearance | — Film thickness (μm) | Urea-based resin (Urea-formaldehyde resin) Additive concentration: 0.1 wt % — Appearance | — Film thickness (μm) | Melamine-based resin (Melamine resin) Additive concentration: 0.1 wt % — Appearance | — Film thickness (μm) | Acrylic melamine-based resin (Acrylic melamine resin) Additive concentration: 3.0 wt % — Appearance | — Film thickness (μm) |
|---|---|---|---|---|---|---|---|---|---|
| (Compound 23) | 106 | ○ | 121 | ○ | 145 | ○ | 70 | ○ | 176 |
| Working example 19 | 106 | ○ | 121 | ○ | 60 | ○ | 26 | ○ | 105 |
| Working example 20 | 104 | ○ | 125 | ○ | 54 | ○ | 45 | ○ | 128 |
| Working example 21 | 150 | ○ | 180 | ○ | 80 | ○ | 50 | ○ | 120 |
| Working example 22 | 200 | ○ | 150 | ○ | 81 | ○ | 50 | ○ | 140 |
| Working example 23 | 160 | ○ | 160 | ○ | 85 | ○ | 48 | ○ | 150 |

4. Evaluation of Ultraviolet Absorber Elution (Bleed-Out) from Organic Resin Composition As for the compound(s) of the present invention and the organic resin composition(s) described in 3., the elution of the compound (ultraviolet absorber) from the resin was evaluated by the following operation, using the compounds 1, 2, 6, 9 and 17 (Table 6).

Here, 0.8 mL of a resin solution prepared by an operation similar to that described in 3, was applied to a 1.5×6.0 cm glass slide to produce a film/glass slide (by an operation similar to that described in 3.), where each film/glass slide was then dipped into 80 mL of heptane and left to stand still in a thermostatic bath of 60° C., for six hours. Next, the film/glass slide was taken out, and the heptane was distilled away under a reduced pressure. An eluted substance obtained was then dissolved in THF, followed by performing quantitation using HPLC (high-performance liquid chromatography, UltiMate 3000 by Thermo Fisher Scientific Inc.).

The appearance of the film(s) after the test was observed visually, and evaluated based on the following criteria.

o: Same level of transparency as compared to before the test

Δ: Slightly clouded as compared to before the test x: Significantly clouded as compared to before the test As can be seen from Table 6, the elution amount in the polymethylmethacrylate resin film as a (meth)acryl-based resin serving as a thermoplastic resin/polymer containing each of the compounds 1, 2, 6, 9 and 17 of the present invention; the elution amount in the polyethylene terephthalate film as an ester-based resin serving as a thermoplastic resin/polymer containing each of the compounds 1, 2, 6, 9 and 17; the elution amount in the polycarbonate film as a polycarbonate-based resin serving as a thermoplastic resin/polymer containing each of the compounds 1, 2, 6, 9 and 17; the elution amount in the polystyrene film as a styrene-based resin serving as a thermoplastic resin/polymer containing each of the compounds 1, 2, 6, 9 and 17; the elution amount in the ABS resin film as an acrylonitrile-butadiene-styrene-based copolymer serving as a thermoplastic resin/copolymer containing each of the compounds 1, 2, 6, 9 and 17; the elution amount in the urea-formaldehyde resin film as a urea-based resin serving as a thermosetting resin/polymer containing each of the compounds 1, 2, 6, 9 and 17; and the elution amount in the melamine resin film as a melanin-based resin serving as a thermosetting resin/polymer containing each of the compounds 1, 2, 6, 9 and 17 were all not larger than 10.0 wt % i.e. favorable results were obtained without having the appearance(s) seriously impaired after the test. Further, even among the thermoplastic resins/polymers, the polymethylmethacrylate resin film, the polyethylene terephthalate film and the polycarbonate film exhibited a particularly favorable result(s) where the elution amount was smaller than 1.0 wt % each; and even among the thermosetting resins/polymers, the urea-formaldehyde resin film exhibited a particularly favorable result where the elution amount was smaller than 1.0 wt %. Meanwhile, as for the acrylic melamine resin film as a thermosetting resin/copolymer, the film exhibited white turbidity after the test, where an elution amount of not smaller than 95% was confirmed.

Based on the above results, it was indicated that the organic resin compositions containing the compounds of the present invention, such as the thermoplastic resins/polymers, the thermal plastic resins/copolymers and the thermosetting resins/polymers are in particular superior in appearance, and are capable of maintaining an ultraviolet absorption capability for a long period of time by suppressing elution owing to bleed-out or the like when dispersed, heat-processed or used for a long period of time.

These thermoplastic resins/polymers can be categorized into crystalline resins (e.g. polyethylene terephthalate) and non-crystalline resins (polymethylmethacrylate resin, polycarbonate and polystyrene); even among the crystalline resins and non-crystalline resins, resins with a higher degree of molecular orientation (polymethylmethacrylate resin and polycarbonate) have aromatic rings on their side chains, and were confirmed to exhibit an elution suppression effect higher than those of the resins with a lower degree of molecular orientation (polystyrene).

TABLE 6

| | Structure | (Meth) acryl-based resin (Polymethyl-methacrylate resin) Additive concentration: 3.0 wt % | | Ester-based resin (PET: Polyethylene terephthalate) Additive concentration: 3.0 wt % | | Polycarbonate-based resin (PC: Polycarbonate) Additive concentration: 3.0 wt % | | Styrene-based resin (PS: Polystyrene) Additive concentration: 3.0 wt % | |
|---|---|---|---|---|---|---|---|---|---|
| | | Elution rate (%) | Appearance | Elution rate (%) | Appearance | Elution rate (%) | Appearance | Elution rate (%) | Appearance |
| Working example 24 | Compound 1 | <1.0 | ○ | <1.0 | ○ | <1.0 | ○ | 10.0 | △ |
| Working example 25 | Compound 2 | <1.0 | ○ | <1.0 | ○ | <1.0 | ○ | 8.5 | △ |
| Working example 26 | Compound 6 | <1.0 | ○ | <1.0 | ○ | <1.0 | ○ | 9.2 | △ |
| Working example 27 | Compound 9 | <1.0 | ○ | <1.0 | ○ | <1.0 | ○ | 9.0 | △ |

TABLE 6-continued

| Working example 28 | Compound 17 | HO–[structure]–Me | <1.0 | ○ | <1.0 | ○ | <1.0 | ○ | 8.0 | △ |

| | Acrylonitrile-butadiene-styrene-based copolymer (ABS resin: acrylonitrile-butadiene-styrene copolymer) Additive concentration: 3.0 wt % | | Urea-based resin (Urea-formaldehyde resin) Additive concentration: 0.1 wt % | | Melamine-based resin (Melamine resin) Additive concentration: 0.1 wt % | | Acrylic melamine-based resin (Acrylic melamine resin) Additive concentration: 3.0 wt % | |
|---|---|---|---|---|---|---|---|---|
| | Elution rate (%) | Appearance | Elution rate (%) | Appearance | Elution rate (%) | Appearance | Elution rate (%) | Appearance |
| Working example 24 | 10.0 | △ | <1.0 | ○ | 4.6 | ○ | 95.5 | x |
| Working example 25 | 9.3 | △ | <1.0 | ○ | 2.1 | ○ | 95.8 | x |
| Working example 26 | 7.6 | △ | <1.0 | ○ | 3.9 | ○ | 96.0 | x |
| Working example 27 | 9.5 | △ | <1.0 | ○ | 4.0 | ○ | 96.5 | x |
| Working example 28 | 8.8 | △ | <1.0 | ○ | 1.6 | ○ | 96.2 | x |

5. Heat Resistance Evaluation of Ultraviolet Absorber

With regard to the heat resistance of the ultraviolet absorber, a rate of change in weight owing to thermal decomposition was evaluated. Here, 5 g of each of the compounds 2, 6, 9, 1 and 19 that had been dried at 50° C., for 12 hours in a pressure-reduced drying machine was weighed and put into a 30 mL screw tube to then measure the weight thereof. The screw tube containing the compound was then left to stand still in a thermostatic device whose temperature was set to 120° C., and a change in appearance as well as the rate of change in weight were observed after 24, 48, 72, 100 and 300 hours. The change(s) in appearance was evaluated by the following criteria. As for the rate of change in weight, an electronic balance was used to measure the weights before and after heating, and the rate of change in weight was then calculated by the formula, [(((weight before heating)−(weight after heating))/weight before heating)×100].

Next, heat resistance evaluation was performed under a condition(s) of 80° C., and 160° C. In a similar manner as above, 5 g of each of the compounds 2, 6, 9 and 1 that had been dried at 50° C., for 12 hours in a pressure-reduced drying machine was weighed and put into a 30 mL screw tube to then measure the weight thereof. The screw tube was then left to stand still in a thermostatic device whose temperature was set to 80° C., and the change in appearance as well as the rate of change in weight were observed after 300 hours. Further, by a similar operation, the screw tube was left to stand still in a thermostatic device whose temperature was set to 160° C., and the change in appearance as well as the rate of change in weight were observed after 6, 12 and 24 hours, where the change in appearance was evaluated by the following criteria.

Evaluation Criteria

Heat Resistance Evaluation at 120° C.

o; Change in appearance: No changes

Δ; Change in appearance: Light yellow x; Change in appearance: Yellow

Heat Resistance Evaluation at 160° C.

◎; Change in appearance: No changes o; Change in appearance: Light yellow

Δ; Change in appearance: Yellow x; Change in appearance: Black

In the heat resistance test carried out at 80° C., for 300 hours, it was confirmed that the compounds 2, 6, 9 and 1 did not discolor. Further, no change(s) in weight were observed. As can be seen from Table 7, after being heated at 120° C., for 48 hours, while the compound 19 of the reference example turned light yellow, the compounds 2, 6, 9 and 1 of the working examples of the present invention did not discolor. That is, it was confirmed that as compared to the compound 19 of the reference example, the compound(s) of the present invention having the thioaryl ring group had a heat resistance.

Next, as can be seen from Table 8, under the condition of 160° C., the effect of the substituent group in the thioaryl ring group was evaluated. As compared to the compound 1 (6 h: black) having no alkyl group in the thioaryl ring group, the compounds 2, 6 and 9 (6 h: no changes to yellow) having an alkyl group(s) in the thioaryl ring group exhibited smaller changes in appearance after a long period of time, thus being superior in heat resistance. Further, it was confirmed that the compounds 2 and 6 (6 h: no changes, 12 h: no changes to light yellow) whose alkyl groups have 3, 4 carbon atoms had a heat resistance higher than that of the compound 9 (6 h: yellow; 12 h: yellow) whose alkyl group has 1 carbon atom; particularly, it was confirmed that the compound 2 (12 h: no changes) whose alkyl group has 4 carbon atoms was superior to the compound 6 (12 h: light yellow) whose alkyl group has 3 carbon atoms in heat resistance.

Further, as for the change(s) in weight under a heated environment, as can be seen from Table 7, after being heated at 120° C., for 48 hours, while the rate of change in weight of the compound 19 of the reference example was 0.03% by weight, the rate of change in weight of each of the compounds 2, 6, 9 and 1 of the working examples was 0.01% by weight i.e. the superiority of the aryl ring group was confirmed.

Next, as can be seen from Table 8, after being heated at 160° C., for six hours, while the rate of change in weight of the compound 1 was 0.20% by weight, the rate of change in weight of each of the compounds 2, 6 and 9 was not larger than 0.1% by weight, which indicated that the compounds having alkyl group(s) in the phenyl ring group were superior in heat resistance. Further, after being heated at 160° C., for 12 hours, the rate of change in weight of the compound 6 was 0.03% by weight, and the rate of change in weight of the compound 2 was 0.01% by weight, which indicated that compounds having, in the phenyl ring group, alkyl groups having 3, 4 carbon atoms were superior in heat resistance; after being heated for 24 hours, the compound 2 (rate of change in weight: 0.01) whose alkyl group has 4 carbon atoms was superior to the compound 6 (rate of change in weight: 0.04) whose alkyl group has 3 carbon atoms in heat resistance.

Moreover, as a result of measuring a 5% weight reduction temperature of the compounds 1 and 19 at the time of heating, using a TG/DTA measurement device (by Seiko Instruments Inc.), under a nitrogen atmosphere and a temperature rising condition of 10° C./min, while the 5% weight reduction temperature of the compound 19 of the reference example was 294° C., the 5% weight reduction temperature of the compound 1 was 290° C., which brought a result where the compound 19 exhibited a higher 5% weight reduction temperature. However, as shown in this heat resistance evaluation test, in the heat resistance evaluation that was carried out under a more practical condition, the results were such that the compound 1 having the phenyl residues, as the ultraviolet absorber of the present invention had a high heat resistance.

Normal molding temperatures for general thermoplastic resins are such that polymethylmethacrylate resin (PMMA): 160° C. or higher; polyethylene terephthalate (PET): 260° C. or higher; polycarbonate (PC): 220° C. or higher; polystyrene (PS): 100° C. or higher; ABS resin ABS: 220° C. or higher. Normal thermal curing temperatures for thermosetting resins are such that urea-formaldehyde resin: 150° C.; melamine resin: 150° C.; acrylic melamine resin film: 150° C. Though depending on the molding time and thermal curing time of a resin, the ultraviolet absorber of the present invention has a high heat resistance, and can thus be favorably used in a resin(s) having a thermal molding temperature or thermal curing temperature of not lower than 80° C., particularly not lower than 120° C., more particularly not lower than 160° C.

TABLE 7

| | | Structure | 5% weight reduction temperature (° C.) | 120° C. Upper: appearance Lower: rate of change in weight (%) | | | | | |
|---|---|---|---|---|---|---|---|---|---|
| | | | | 0 h | 24 h | 48 h | 72 h | 100 h | 300 h |
| Working example 29 | Compound 2 | (benzotriazole structure; t-Bu–phenyl–S–; HO, t-Bu, Me substituents) | 309 | ○ 0.00 | ○ 0.00 | ○ 0.01 | ○ 0.01 | ○ 0.01 | ○ 0.01 |
| Working example 30 | Compound 6 | (benzotriazole structure; i-Pr–phenyl–S–; HO, t-Bu, Me substituents) | 297 | ○ 0.00 | ○ 0.00 | ○ 0.01 | ○ 0.01 | ○ 0.01 | ○ 0.01 |
| Working example 31 | Compound 9 | (benzotriazole structure; Me–phenyl–S–; HO, t-Bu, Me substituents) | 293 | ○ 0.00 | ○ 0.00 | ○ 0.01 | ○ 0.01 | ○ 0.01 | ○ 0.01 |
| Working example 32 | Compound 1 | (benzotriazole structure; phenyl–S–; HO, t-Bu, Me substituents) | 290 | ○ 0.00 | ○ 0.00 | ○ 0.01 | ○ 0.01 | ○ 0.01 | ○ 0.01 |
| Reference example 4 | Compound 19 | (benzotriazole structure; $CH_3(CH_2)_7S$–; HO, t-Bu, Me substituents) | 294 | ○ 0.00 | ○ 0.00 | △ 0.03 | △ 0.05 | △ 0.05 | x 0.06 |

TABLE 8

| | | Structure | 5% weight reduction temperature (° C.) | 160° C. Upper: appearance Lower: rate of change in weight (%) | | | |
|---|---|---|---|---|---|---|---|
| | | | | 0 h | 6 h | 12 h | 24 h |
| Working example 33 | Compound 2 | (benzotriazole structure; t-Bu–phenyl–S–; HO, t-Bu, Me substituents) | 309 | ◎ 0.00 | ◎ 0.00 | ◎ 0.01 | ◎ 0.01 |
| Working example 34 | Compound 6 | (benzotriazole structure; i-Pr–phenyl–S–; HO, t-Bu, Me substituents) | 297 | ◎ 0.00 | ◎ 0.02 | ○ 0.03 | ○ 0.04 |

TABLE 8-continued

| | | Structure | 5% weight reduction temperature (° C.) | 160° C. Upper: appearance Lower: rate of change in weight (%) | | | |
|---|---|---|---|---|---|---|---|
| | | | | 0 h | 6 h | 12 h | 24 h |
| Working example 35 | Compound 9 | (chemical structure: HO, t-Bu, Me, Me, S, triazole) | 293 | ◎ 0.00 | △ 0.08 | △ 0.08 | △ 0.12 |
| Working example 36 | Compound 1 | (chemical structure: HO, t-Bu, Me, S, triazole) | 290 | ◎ 0.00 | x 0.20 | x 0.22 | x 0.22 |

6. Heat Resistance Evaluation of Organic Resin Composition Containing Ultraviolet Absorber <1> Preparation of Sample for Heat Resistance Evaluation Ultraviolet Absorber/Thermoplastic Resin, (Meth)Acryl-Based Resin: Polymethylmethacrylate Resin Each of the compounds 2, 6, 9, 1 and 19 as the ultraviolet absorbers of the present invention and the compound 19 of the reference example 5 was dissolved into a 2.5 wt % polymethylmethacrylate resin (by Tokyo Chemical Industry Co., Ltd.) chloroform solution in a manner such that the compound dissolved would be in an amount of 10 wt % with respect to the acrylic resin, followed by delivering about 0.5 ml of the solution by drops onto a glass (glass slide, MICRO SLIDE GLASS S1112 by Matsunami Glass Ind., Ltd.), and then performing spin coating to form a film, thereby obtaining an evaluation sample.

Ultraviolet Absorber/Thermoplastic Resin, Polycarbonate-Based Resin: Polycarbonate Each of the compounds 2, 6, 9, 1 and 19 as the ultraviolet absorbers of the present invention and the compound 19 of the reference example 5 was dissolved into a 5.0 wt % polycarbonate chloroform solution in a manner such that the compound dissolved would be in an amount of 10 wt % with respect to the acrylic resin, followed by delivering about 0.5 ml of the solution by drops onto a glass (glass slide, MICRO SLIDE GLASS S1112 by Matsunami Glass Ind., Ltd.), and then performing spin coating to form a film, thereby obtaining an evaluation sample.

Ultraviolet Absorber/Thermosetting Resin, Acrylic Melamine-Based Resin: Acrylic Melamine Resin Each of the compounds 2, 6, 9, 1 and 19 as the ultraviolet absorbers of the present invention and the compound 19 of the reference example 5 was dissolved into a 5.0 wt % acrylic melamine resin chloroform solution in a manner such that the compound dissolved would be in an amount of 10 wt % with respect to the acrylic resin, followed by delivering about 0.5 ml of the solution by drops onto a glass (glass slide, MICRO SLIDE GLASS S1112 by Matsunami Glass Ind., Ltd.), and then performing spin coating to form a film, thereby obtaining an evaluation sample.

<2> Appearance and Heat Resistance Evaluation

The evaluation sample obtained in the above manner was then left to stand still and be heated in a thermostatic device that was set to 160° C., and a change(s) in appearance as well as the transmittance thereof were observed after 6 and 12 hours. The change(s) in appearance were evaluated by the following criteria.

Evaluation Criteria

Heat resistance evaluation at 160° C.

○; Change in appearance: No changes

△; Change in appearance: Light yellow x; Change in appearance: Yellow

As for transmittance, an ultraviolet and visible spectrophotometer (spectrophotometer UH4150 by Hitachi, Ltd.) was used to measure a UV-Vis transmission spectrum, where initial (before-irradiation) ultraviolet transmittances ($T_1$uv: %) at 380, 390 and 400 nm were read, a UV-Vis transmission spectrum after heating was measured, transmittances ($T_2$uv: %) at 380, 390 and 400 nm were read, and a difference in transmittance $\Delta$Tuv (%) was then calculated by the following formula.

$$\text{Difference in transmittance } (\Delta Tuv) = T_1uv - T_2uv \ (\%). \quad \text{[Formula 1]}$$

TABLE 9

| Structure | Wavelength observed (nm) | (Meth)acryl-based resin (Polymethyl methacrylate resin) ΔTuv(%) 6 h | ΔTuv(%) 12 h | Rate of change in ΔTuv [|ΔTuv(12 h)/ ΔTuv (6 h)] (%) | Appearance 12 h | Polycarbonate-based resin (PC: Polycarbonate) ΔTuv(%) 6 h | ΔTuv(%) 12 h | Rate of change in ΔTuv [|ΔTuv(12 h)/ ΔTuv (6 h)] (%) | Appearance 12 h | Acrylic melamine-based resin (Acrylic melamine resin) ΔTuv(%) 6 h | ΔTuv(%) 12 h | Rate of change in ΔTuv [|ΔTuv(12 h)/ ΔTuv (6 h)] (%) | Appearance 12 h |
|---|---|---|---|---|---|---|---|---|---|---|---|---|---|
| Working example 37 Compound 2 | 400 | 9.5 | 16.8 | 177 | ○ | 12.1 | 13.7 | 113 | ○ | 4.8 | 13.5 | 293 | ○ |
|  | 390 | 15.4 | 35.6 | 231 | ○ | 15.7 | 26.4 | 168 | ○ | 1.8 | 5.6 | 311 | ○ |
|  | 380 | 15.5 | 42.9 | 277 | ○ | 15.9 | 30.1 | 189 | ○ | 0.7 | 2.7 | 386 | ○ |
| Working example 38 Compound 6 | 400 | 12.4 | 17.6 | 142 | ○ | 15.0 | 19.2 | 128 | ○ | 5.2 | 18.1 | 348 | ○ |
|  | 390 | 23.2 | 36.3 | 156 | ○ | 16.1 | 30.3 | 188 | ○ | 2.3 | 10.2 | 443 | ○ |
|  | 380 | 26.5 | 43.9 | 166 | ○ | 16.2 | 31.2 | 193 | ○ | 1.1 | 6.0 | 545 | ○ |
| Working example 39 Compound 9 | 400 | 18.1 | 21.5 | 119 | ○ | 21.5 | 22.3 | 104 | ○ | 7.5 | 30.7 | 409 | ○ |
|  | 390 | 31.9 | 44.2 | 139 | ○ | 39.9 | 40.2 | 101 | ○ | 2.5 | 16.2 | 648 | ○ |
|  | 380 | 34.2 | 60.3 | 176 | ○ | 45.0 | 56.6 | 126 | ○ | 1.5 | 9.6 | 640 | ○ |
| Working example 40 Compound 1 | 400 | 18.4 | 21.6 | 117 | ○ | 21.8 | 22.7 | 104 | ○ | 14.6 | 59.5 | 408 | ○ |
|  | 390 | 35.1 | 48.9 | 139 | ○ | 42.8 | 43.4 | 101 | ○ | 5.9 | 54.7 | 927 | ○ |
|  | 380 | 39.0 | 61.4 | 157 | ○ | 46.0 | 57.7 | 125 | ○ | 2.6 | 45.1 | 1735 | ○ |

Structures:

Working example 37, Compound 2: benzotriazole with HO, t-Bu, Me substituents and S-linked 4-t-Bu phenyl group.

Working example 38, Compound 6: benzotriazole with HO, t-Bu, Me substituents and S-linked 4-i-Pr phenyl group.

Working example 39, Compound 9: benzotriazole with HO, t-Bu, Me substituents and S-linked 4-Me phenyl group.

Working example 40, Compound 1: benzotriazole with HO, t-Bu, Me substituents and S-linked phenyl group.

TABLE 9-continued

| | Structure | Wavelength observed (nm) | (Meth)acryl-based resin (Polymethyl methacrylate resin) | | | | Polycarbonate-based resin (PC: Polycarbonate) | | | | Acrylic melamine-based resin (Acrylic melamine resin) | | | |
|---|---|---|---|---|---|---|---|---|---|---|---|---|---|---|
| | | | ΔTuv(%) 6 h | ΔTuv(%) 12 h | Rate of change in ΔTuv [ΔTuv (12 h)/ ΔTuv (6 h)] (%) | Appearance 12 h | ΔTuv(%) 6 h | ΔTuv(%) 12 h | Rate of change in ΔTuv [ΔTuv (12 h)/ ΔTuv (6 h)] (%) | Appearance 12 h | ΔTuv(%) 6 h | ΔTuv(%) 12 h | Rate of change in ΔTuv [ΔTuv (12 h)/ ΔTuv (6 h)] (%) | Appearance 12 h |
| Reference example 5 | Compound 19 <br> (structure) | 400 | 19.1 | 22.4 | 117 | ○ | 23.6 | 23.6 | 100 | ○ | 24.5 | 61.1 | 249 | ○ |
| | | 390 | 36.0 | 50.7 | 141 | ○ | 45.4 | 46.8 | 103 | ○ | 6.7 | 62.6 | 934 | ○ |
| | | 380 | 40.1 | 64.9 | 162 | ○ | 46.9 | 58.2 | 124 | ○ | 3.4 | 55.5 | 1632 | ○ |

As for the appearance evaluations in Table 9, the ultraviolet absorbers of the working examples 37 to 40 and the organic resin compositions containing them were transparent due to a favorable affinity to glass, superior in heat resistance, and maintained a favorable appearance both immediately after the evaluation sample was prepared and after being heated for 12 h (also suitable as an ultraviolet shielding film). As compared to the thioalkyl group-containing compound 19 of the reference example, the thioaryl ring group-containing compounds 2, 6, 9 and 1 each correspondingly exhibited a smaller $\Delta$Tuv(s) at 380, 390 and 400 nm after 6, 12 h (no deterioration in ultraviolet absorption capability), and a more excellent heat resistance i.e. the superiority of the aryl ring group was confirmed.

Further, as a result of comparing the $\Delta$Tuvs of the compounds 2, 6, 9 and 1 at 380, 390 and 400 nm after 6 h and 12 h, the resin compositions were in such a correlation with one another that: compound 2 (Ph-tBu)/organic resin <compound 6 (Ph-iPr)/organic resin <compound 9 (Ph-Me)/organic resin <compound 1 (Ph)/organic resin (e.g. polymethacrylic methyl resin, 400 nm, after 6 h. compound 2: 9.5<compound 6: 12.4<compound 9: 18.1<compound 1: 18.4). That is, the organic resin compositions of compounds having a linear or branched alkyl group(s) in the aryl ring group (phenyl residue) were superior in light resistance. Particularly, in terms of alkyl group, an organic resin composition having an iPr group with 3 carbon atoms or a tBu group with 4 carbon atoms was superior to that having a methyl group with 1 carbon atom in heat resistance; more particularly, an organic resin composition having a tBu group with 4 carbon atoms was superior to that having an iPr group with 3 carbon atoms in heat resistance.

A rate(s) of change in $\Delta$Tuv ($\Delta$Tuv (12 h)/$\Delta$Tuv (6 h)) was calculated from $\Delta$Tuv (6 h) after 6 h and $\Delta$Tuv (12 h) after 12 h, and are shown in Table 9. The rates of change in the cases of the resin compositions of the combination of ultraviolet absorber/polymethylmethacrylate resin as a thermoplastic resin and the combination of ultraviolet absorber/polycarbonate as a thermoplastic resin, were smaller than that in the case of the resin composition of the combination of ultraviolet absorber/acrylic melamine resin as a thermosetting resin, and were superior in heat resistance.

7. Light Resistance Evaluation of Glass Having Ultraviolet Shielding Film as Inorganic Material (Glassy Material)

<1> Preparation of Sample for Light Resistance Evaluation

Using a paint conditioner, each of the compounds 2, 6, 7, 9, 16, 19 and 21 as the ultraviolet absorbers of the present invention as well as the compound 22 of the comparative example 2 (TINUVIN360, 2,2'-methylenebis [6-(benzotriazole-2-yl)-4-tert-octylphenyl] by Ciba Specialty Chemicals) was mixed with zirconia beads and then pulverized into fine particles having an average particle size of 100 nm. An aqueous dispersion containing 10% by mass of such ultraviolet absorber fine particles, a pure water, an ethyl alcohol, tetraethoxysilane (TEOS), glycidoxypropyltrimethoxy silane (GPTMS; 3-glycidyloxy propyltrimethoxy silane) as a silane coupling agent, triethyleneglycol (TEG) as a polyol compound, a polyether phosphate ester-based polymer (Solsperse 41000 by The Lubrizol Corporation) as a polyether compound, an ITO fine particle dispersion liquid (ethylene alcohol solution containing 40% by mass of ITO particles; by Mitsubishi Materials Corporation, average particle size (nominal) 100 nm or smaller) and a concentrated hydrochloric acid (35% by mass) were mixed and stirred to obtain a film-forming solution of an ultraviolet shielding film. The film-forming solution was prepared in a way such that the concentration of each component (content rate) would be the value(s) shown in Table 10. A compound 23 of a comparative example 3 (Uvinul 3050, 2,2',4,4'-tetrahydroxybenzophenone by BASF Japan Ltd.) was at first dissolved in an ethyl alcohol before being added to the film-forming solution. TEG and Solsperse correspond to the organic compound(s) C. Further, in certain working examples, sorbitol polyglycidyl ether (DENACOL EX-614 by Nagase ChemteX Corporation) was used as the organic compound C. Sorbitol polyglycidyl ether is a polyepoxy compound, and turns into a hydroxy group-containing polyol compound in the film, the polyol compound being that generated by a reaction of the glycidyl group(s). However, in the working examples 52 to 54, since the temperature of an oven in the heating and drying step was set to 180° C., which was even higher than the melting point of the organic compound A, the organic compound A melted and was thus added to the film. Next, by a flow coating method, this forming solution was applied to a washed soda-lime silicate glass substrate (commercially available UV-cut green glass 100×100 mm, thickness 3.1 mm) under a humidity of 30% and room temperature. After being directly dried at room temperature for about 5 min, the substrate was then put into an oven whose temperature had already been raised to the temperature(s) shown in Table 10, and was heated for 15 min before being cooled as to form an ultraviolet shielding film thereon. A correlation(s) between the temperature of the film-coated glass the melting point of the ultraviolet absorber in such heating process are shown in Table 10. In the working examples 41 to 51, 55 and 56; and comparative example 2, the temperatures of the film-coated glass were lower than the melting points of the ultraviolet absorbers; in such heating process, the temperatures of the film-coated glass would not surpass the melting points of the ultraviolet absorbers. Here, the UV-cut green glass used exhibited a light transmittance of 40% at a wavelength of 380 nm (T380), and a light transmittance of 77% at a wavelength of 550 nm (T550). This UV-cut green glass contained about 0.9% by mass of a total iron oxide(s) in terms of $Fe_2O_3$. In the working examples 52 to 54, since the temperature of an oven in the heating and drying step was set to 180° C., which was even higher than the melting points of the ultraviolet absorbers, the ultraviolet absorbers melted and were thus added to the film. In the comparative example 2, since the ultraviolet absorber was added to the film-forming solution as an ethylene alcohol solution, the ultraviolet absorber dissolved and was thus added to the film.

TABLE 10

Preparation of glass composition, production of glass plate sample

| | Silicon oxide component | | | Ultraviolet absorber a/b | | Organic compound C | | | | ITO | Organic compound B/Part | Oven temp- | Interaction between heating temp- erature/ melting point of |
| | Part by mass | TEOS- derived | GPTMS- derived | Compound No. | Part by mass | C1 | Part by mass | C2 | Part by mass | Part by mass | by mass | erature (° C.) | ultraviolet absorber |
|---|---|---|---|---|---|---|---|---|---|---|---|---|---|
| Working example 41 | 100 | 92.5 | 7.5 | Compound 16 | 28.9 | TEG | 3.8 | Solsperse | 2.2 | 11.1 | — | 65 | Low |
| Working example 42 | 100 | 90 | 10 | Compound 9 | 26.7 | TEG | 3.8 | Solsperse | 2.2 | 11.1 | — | 65 | Low |
| Working example 43 | 100 | 90 | 10 | Compound 6 | 21.1 | TEG | 3.8 | Solsperse | 2.2 | 11.1 | — | 65 | Low |
| Working example 44 | 100 | 95 | 5 | Compound 6 | 18.9 | — | 0 | Solsperse | 2.2 | 11.1 | | 65 | Low |
| Working example 45 | 100 | 90 | 10 | Compound 6 | 18.3 | TEG | 3.8 | Solsperse | 2.2 | 11.1 | Compound 22/6.1 | 65 | Low |
| Working example 46 | 100 | 95 | 5 | Compound 2 | 22.2 | — | 0 | Solsperse | 2.2 | 11.1 | — | 65 | Low |
| Working example 47 | 100 | 95 | 5 | Compound 2 | 20 | — | 0 | Solsperse | 2.2 | 11.1 | — | 65 | Low |
| Working example 48 | 100 | 90 | 10 | Compound 2 | 14.5 | DEN | 12.5 | Solsperse | 1.8 | 91 | — | 65 | Low |
| Working example 49 | 100 | 87.5 | 12.5 | Compound 2 | 14.5 | DEN | 10 | Solsperse | 1.8 | 9.1 | — | 65 | Low |
| Working example 50 | 100 | 82.5 | 17.5 | Compound 2 | 14.5 | — | 0 | Solsperse | 1.8 | 9.1 | — | 65 | Low |
| Working example 51 | 100 | 85 | 15 | Compound 2 | 15.5 | DEN | 2.5 | Solsperse | 1.8 | 9.1 | — | 65 | Low |
| Working example 52 | 100 | 92.5 | 7.5 | Compound 16 | 28.9 | TEG | 3.8 | Solsperse | 2.2 | 11.1 | — | 180 | High |
| Working example53 | 100 | 90 | 10 | Compound 9 | 26.7 | TEG | 3.8 | Solsperse | 2.2 | 11.1 | — | 180 | High |
| Working example 54 | 100 | 92.5 | 75 | Compound 9 | 27.8 | TEG | 3.8 | Solsperse | 2.2 | 11.1 | — | 180 | High |
| Working example 55 | 100 | 8292.5 | 7.5 | Compound 21 | 17.8 | TEG | 5 | Solsperse | 2.2 | 11.1 | — | 65 | Low |
| Working example 56 | 100 | 85 | 15 | Compound 7 | 18.2 | DEN | | Solsperse | 1.8 | 9.1 | — | 65 | Low |
| Comparative example 2 | 100 | 92.5 | 7.5 | — | — | TEG | 3.8 | Solsperse | 2.2 | 11.1 | Compound 22/15.6 | 65 | Low |
| Comparative example 3 | 100 | 40 | 60 | — | — | — | 0 | 57 additive | 0.14 | 6.9 | Compound 23/44.8 | 65 | Intro- duced after dis- solution |

<2> Optical Property Evaluation

Optical properties were measured using a spectrophotometer (UV-3100PC by Shimadzu Corporation). The properties measured were a visible light transmittance Tvis measured using an A light source of CIE standard in accordance with JIS R$^{3212}$; an ultraviolet transmittance $T_{uv}380$ calculated in accordance with ISO9050 (1990 edition); an ultraviolet transmittance $T_{uv}400$ calculated in accordance with ISO13837 (convention A); a blue light cut ratio BLcut calculated based on a blue light hazard function defined in JIS T7330; a L*a*b *color system of a transmitted light that is measured using a C light source of CIE standard in accordance with JIS Z8729; a yellow index YI of a transmitted light that is measured using a C light source of CIE standard in accordance with JIS K7373 (2006); a dominant wavelength and excitation purity of a transmitted light that is measured using a C light source of CIE standard in accordance with JIS Z8701 (1999); and a light transmittance T1500 at a wavelength of 1,500 nm. Here, $T_{uv}380$ was a value calculated based on light transmittances at wavelengths of 280 to 380 nm, $T_{uv}400$ was a value calculated based on light transmittances at wavelengths of 300 to 400 nm, and the blue light cut ratio was a value calculated based on light transmittances at wavelengths of 380 to 500 nm.

<3> Light Resistance (Ultraviolet Resistance Property) Evaluation

Light resistance (ultraviolet resistance property) was evaluated in a manner such that an ultraviolet irradiation device (EYE SUPER UV TESTER SUV—W13) manufactured by IWASAKI ELECTRIC CO., LTD, was used to irradiate the ultraviolet shielding film-coated glass from a surface thereof on which the film was not formed with an ultraviolet for a given period of time (100 hours) and under a condition(s) of: wavelength 295 to 450 nm; irradiance 76 mW/cm$^2$; black panel temperature 83° C.; humidity 50% RH. Optical properties (YA, $T_{uv}400$) after the ultraviolet irradiation test were measured, and changes before and after the test ($\Delta$YA, $\Delta T_{uv}400$) were then calculated.

TABLE 11

High light resistance effect with glass plate

| | | | | | | Optical property | | | | | | | Light resistance | |
| | Film thick-ness | Tvis | Tuv380 | Tuv400 | BL cut | L*a*b* | | | Yel-low index | Domi-nant wave-length | Exci-tation purity | T1500 | Change in transmittance after UV irradiation | |
| | (µm) | (%) | (%) | (%) | (%) | L* | a* | b* | Y! | (nm) | (%) | (%) | ΔYA | ΔTuv400 |
|---|---|---|---|---|---|---|---|---|---|---|---|---|---|---|
| Glass plate | — | 72.8 | 13.4 | 24.6 | 33.6 | 88.8 | −8.1 | 5.6 | 5 | 549 | 4.3 | 36.4 | 0 | 0 |
| Working example 41 | 3 | 71.9 | 0.04 | 0.88 | 36.7 | 88.4 | −8.7 | 6.9 | 6.9 | 553 | 5.5 | 22.2 | 0.2 | 1.6 |
| Working example 42 | 2.1 | 71.6 | 0.09 | 1 | 38.4 | 88.1 | −8.8 | 7.9 | 8.9 | 557 | 6.6 | 25.5 | 0.5 | 1.8 |
| Working example 43 | 1.7 | 71.9 | 0.3 | 0.75 | 37.4 | 88.4 | −8.9 | 7.1 | 7.2 | 553 | 5.7 | 25.2 | 0.4 | 1 |
| Working example 44 | 2 | 72.6 | 0.3 | 0.83 | 36 | 88.7 | −8.7 | 6.7 | 6.3 | 552 | 5.2 | 25.1 | −0.1 | 1.4 |
| Working example 45 | 2.5 | 70.7 | 0.1 | 0.83 | 39.9 | 87.7 | 9 | 8.5 | 9.8 | 558 | 7.2 | 25.5 | 0.4 | 0.4 |
| Working example 46 | 2.1 | 72.4 | 0.1 | 0.59 | 36.4 | 88.6 | −8.7 | 6.8 | 6.8 | 553 | 5.5 | 25.1 | 0.1 | 0.1 |
| Working example 47 | 2 | 72.3 | 0.1 | 0.8 | 36.2 | 88.6 | −8.7 | 6.8 | 6.7 | 552 | 5.4 | 25.2 | 0.1 | 0.2 |
| Working example 48 | 2.7 | 72.4 | 0.1 | 0.76 | 36.3 | 88.6 | −8.7 | 6.8 | 6.7 | 552 | 5.4 | — | 0 | 0.2 |
| Working example 49 | 2.5 | 72.4 | 0.2 | 0.93 | 36.2 | 88.6 | −8.6 | 6.7 | 6.6 | 552 | 5.4 | — | 0 | 0.2 |
| Working example 50 | 2.3 | 72.4 | 0.2 | 0.91 | 36.2 | 88.6 | −8.6 | 6.8 | 6.8 | 553 | 5.4 | — | 0 | 0.2 |
| Working example 51 | 2.5 | 72.4 | 0.1 | 0.74 | 36.3 | 88.6 | −8.7 | 6.8 | 6.7 | 552 | 5.4 | 24 | 0.2 | 0.2 |
| Working example 52 | 3.2 | 72.1 | 0.04 | 0.5 | 36.3 | 88.5 | −8.7 | 6.5 | 6.2 | 551 | 5.1 | 22.9 | −0.1 | 10 |
| Working example53 | 2.2 | 72.5 | 0.07 | 0.64 | 36.7 | 88.7 | −8.8 | 6.9 | 6.9 | 553 | 5.5 | 25.9 | 0.4 | 6.3 |
| Working example 54 | 2.7 | 72.2 | 0.09 | 0.98 | 36.2 | 88.5 | −8.8 | 6.6 | 6.3 | 551 | 5.2 | 24.8 | −1 | 19 |
| Working example 55 | 1.9 | 72.1 | 0.1 | 0.8 | 36.7 | 88.5 | −8.9 | 6.7 | 6.4 | 551 | 5.3 | 26.2 | 0 | 18 |
| Working example 56 | 2.8 | 72.2 | 0.1 | 0.81 | 36.3 | 88.5 | −8.7 | 6.6 | 6.3 | 551 | 5.2 | 23.5 | −0.1 | 0.1 |
| Comparative example 2 | 3.3 | 72.1 | 0.2 | 7.9 | 35.3 | 88.5 | −8.3 | 6.4 | 6.3 | 552 | 5.1 | 17.6 | — | — |
| Comparative example 3 | 7.5 | 71.4 | 0.02 | 0.27 | 44.5 | 88 | 11.3 | 13.7 | 17.5 | 562 | 12.3 | 18.9 | −0.7 | −0.1 |

As can be seen from the optical property evaluation in Table 1, the glasses of the working examples 41 to 56 using the ultraviolet absorbers of the present invention each exhibit a high adhesion and transparency, and each exhibited, as optical properties, $T_{uv}$ 380 of not higher than 0.3%, $T_{uv}$400 of not higher than 1%, a blue light cut ratio of lower than 40%, a* of −9 to −8 and b* of 5 to 9 in the L*a*b *color system, and a yellow index YI of not higher than 10; as for light resistance, the rate of change in transmittance of each of the glasses of these working examples after the ultraviolet irradiation test ($T_{uv}$400) was not larger than 20, particularly, in the case of the thiophenyl ring group-containing ultraviolet absorber, the rate of change was smaller than 6. Further, in comparing the rates of change in ultraviolet transmittance in Tables 1A and 11, in the cases of the working examples 2 and 47 using the compound 2, the working example 47 where the compound 2 was added to the glassy ultraviolet shielding film exhibited a rate of change lower than that of the working example 2 where the compound was added to the resin film. From this result, it was indicated that in terms of maintaining an ultraviolet shielding effect for a long period of time, the ultraviolet absorber of the present invention was suitable for use in a glassy ultraviolet shielding film. As for a light resistance in the ultraviolet range (rate of change in transmittance: $T_{uv}$400), as a result of comparing similar compounds, the compounds 2, 6, 9 and 7 each having the thioaryl group ($—S—X^{1a}—(R^{1a})_i$) as represented by the formula (1) in [IV] exhibited rates of change that were smaller than those of the compounds 19 and 21 each having a thioalkyl group(s) i.e. it was indicated that the thioaryl group contributed to light resistance. Even among the thioaryl group-containing compounds, compounds whose $R^{1a}$ has 3 to 8 carbon atoms (and contains a tertiary and/or quaternary carbon(s)) were superior in light resistance.

A low $T_{uv}$400 failed to be achieved with the comparative example 2; while a low $T_{uv}$400 was able to be achieved with the comparative example 3, a higher yellow index YI was observed. In contrast, in each working example, $T_{uv}$400 was able to be lowered while suppressing a significant coloration to a yellowish color. Further, in comparing the working examples 41 and 42 with the working examples 52 and 53, it was confirmed that the light resistance of the film could be improved by adding the organic compound A as fine particles. Furthermore, as are the cases with the compounds 2, 6 and 7, when employing an organic compound A having a thioaryl ring group bonded to a branched chain alkyl group as a substituent group of a hydrogen atom, although $ΔT_{uv}$400 of these compounds alone was not exceptionally excellent. $\Delta T_{uv}400$ of the film was able to be controlled in a significant manner.

8. Transparency and Optical Property Evaluation of Glass Having Ultraviolet Shielding Film as Organic Material <1> Preparation of Sample for Light Resistance Evaluation Each of the compounds 1, 2, 9 and 19 as the ultraviolet absorbers of the present invention and the compound 24 of the comparative example 4 was dissolved into a 2.5 wt % polymethylmethacrylate resin (by Tokyo Chemical Industry Co., Ltd.) chloroform solution in a manner such that the compound dissolved would be in an amount of 10 wt % with <2> Appearance and Optical Property Evaluation As for the evaluation sample obtained, the appearance thereof was observed, and an ultraviolet and visible spectrophotometer (spectrophotometer UH4150 by Hitachi, Ltd.) was used to measure a UV-Vis transmission spectrum, where ultraviolet transmittances at 380, 390 and 400 nm were read. Further, the absolute value of the gradient of an absorption peak in a wavelength region of 350 to 390 nm on the long-wavelength side was calculated by a method similar to that described in 1. <1>.

TABLE 12

| | | Structure | Film thickness (nm) | Wavelength (nm) | Transmittance (%) | Absolute value of gradient of absorption peak in wavelength region of 350 to 390 nm on long-wavelength side |
|---|---|---|---|---|---|---|
| Working example 57 | Compound 1 | | 2.0 | 400<br>390<br>380 | 62.7<br>27.7<br>15.0 | 0.0186 |
| Working example 58 | Compound 2 | | 2.4 | 400<br>390<br>380 | 64.3<br>32.0<br>19.4 | 0.0181 |
| Working example 59 | Compound 9 | | 2.6 | 400<br>390<br>380 | 61.2<br>27.5<br>15.9 | 0.0182 |
| Working example 60 | Compound 19 | | 2.3 | 400<br>390<br>380 | 68.7<br>30.5<br>18.5 | 0.0181 |
| Comparative example 4 | Compound 24 | | 2.4 | 400<br>330<br>380 | 86.9<br>63.4<br>38.6 | 0.0103 | respect to the acrylic resin, followed by delivering 1 ml of the solution by drops onto a glass (glass slide, MICRO SLIDE GLASS S1112 by Matsunami Glass Ind., Ltd.), and then using a spin coater (sealed-type spin coater ACT-300AII by ACTIVE Co., Ltd.) to hold the glass at 1,500 rpm for 20 sec so as to form a film, thereby obtaining an ultraviolet shielding film-containing glass as an evaluation sample.

As can be seen from the appearance evaluation in Table 12, in the working examples 57 to 60, even when the ultraviolet absorber was present at a high concentration of 10 wt % with respect to the resin, and the ultraviolet absorber and the glass were thus in a closer contact with each other, a favorable affinity was exhibited, a favorable adhesiveness between the glass and the ultraviolet shielding film was observed, and the ultraviolet shielding film-containing glass had a transparent appearance. Further, it was confirmed that the ultraviolet shielding film-containing glasses of the working examples exhibited transmittances at 380 to 400 nm that were smaller than that of the glass of the comparative example 4; the glasses of the working examples were superior in long-wavelength absorption. Furthermore, the absolute values of the gradients of the absorption peaks of the ultraviolet shielding film-containing glasses of the working examples were larger than that of the comparative example, which indicated that the glasses of the working examples had a yellowing suppression effect.

The invention claimed is:

1. A light-resistant ultraviolet absorber comprising a 2-phenylbenzotriazole derivative that contains a thioaryl ring group or thiocyclohexyl ring group and is represented by any one of the following formulae (1), (3) and (4):

$$PhBzT^{1a}—S—X^{1a}—(R^{1a})_l \tag{1}$$

wherein $PhBzT^{1a}$ represents a 2-phenylbenzotriazole skeleton bonded to a thioaryl ring group (—S—$X^{1a}$— . . . ), the 2-phenylbenzotriazole skeleton being represented by the following formula (A):

(A)

wherein in the formula (A), $R^6$, $R^7$, $R^8$ and $R^9$ are each independently the thioaryl ring group or a hydrogen atom and at least one of $R^6$, $R^7$, $R^8$ and $R^9$ is the thioaryl ring group, $R^1$, $R^2$, $R^3$, $R^4$ and $R^5$ are each independently a hydrogen atom, a hydrocarbon group having 1 to 10 carbon atoms or a hydroxy group, and the thioaryl ring group being such that:

i) $X^{1a}$ represents a residue of phenyl ring, $R^{1a}$ independently represents a tertiary and/or quaternary carbon-containing alkyl group having 3 to 8 carbon atoms, and l represents an integer of 1, ii) $X^{1a}$ represents a residue of phenyl ring, each of l $R^{1a}$s independently represents a linear or branched alkyl group having 1 to 4 carbon atoms, l represents an integer of 2, and a total number of the carbon atoms in these alkyl groups is 2 to 5, iii) $X^{1a}$ represents a residue of phenyl ring, each of l $R^{1a}$s independently represents an alkoxy group possessing a linear or branched alkyl group having 1 to 18 carbon atoms, and l represents an integer of 1 to 3, and wherein the light-resistant ultraviolet absorber exhibits a difference in transmittance ($\Delta$Tuv) of not larger than 2.0% at at least one of wavelengths of 380, 390 and 400 nm when measured under the following condition:

<Condition for measuring difference in transmittance> a sample prepared by applying to a soda glass an acrylic resin and the ultraviolet absorber at a mass ratio of 0.6 to 3.4:0.1 and at a film thickness of 2 to 50 μm is irradiated with an ultraviolet for 70 hours under a condition(s) of wavelength 300 to 400 nm, irradiance 42 W/m², black panel temperature 63° C.; based on a transmittance by UV-Vis transmission spectrum before irradiation ($T_1$uv) and a transmittance by UV-Vis transmission spectrum after irradiation ($T_2$uv), calculation is performed using the following formula:

$$\text{Difference in transmittance } (\Delta Tuv) = T_1uv - T_2uv \ (\%),$$

or $$PhBzT^{1c}—S—A^{1c}—S—PhBzT^{2c} \tag{3}$$

wherein each of $PhBzT^{1c}$ and $PhBzT^{2c}$ independently represents a substituted or unsubstituted 2-phenylbenzotriazole skeleton bonded to a thioaryl ring group represented by —S-$A^{1c}$-S— in formula (3), wherein $A^{1c}$ represents a phenyl or naphthyl ring residue or is a group expressed by the following formula, $$—[X^{1c}—(R^{1c})_n]—(A^{2c})_q—[X^{2c}—(R^{2c})_p]—$$

wherein each of $X^{1c}$ and $X^{2c}$ independently represents a residue of a phenyl or naphthyl ring, each of n $R^{1c}$s and p $R^{2c}$s independently represents a hydrocarbon group having 1 to 18 carbon atoms, an alkoxy group having 1 to 18 carbon atoms or a hydroxy group, each of n and p represents an integer of 0 to 4, $A^{2c}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom, a divalent aromatic group or a sulfide group-S—, q represents an integer of 0 or 1;

$$(R^{1d})_r—X^{1d}-S—PhBzT^{1d}-A^{1d}-PhBzT^{2d}-S—X^{2d}—(R^{2d})_e \tag{4}$$

wherein each of —$X^{1d}$—S-$PhBzT^{1d}$- and -$PhBzT^{2d}$-S—$X^{2d}$— moiety in formula (4) independently represents a substituted or unsubstituted 2-phenylbenzotriazole skeleton that has a thioaryl ring group represented by —$X^{1d}$—S— or —S—$X^{2d}$— in formula (4) bonded to a phenyl moiety of a benzotriazole skeleton and $A^{1d}$ bonded to a position-2 phenyl skeleton Ph, each of $X^{1d}$ and $X^{2d}$ independently represents a residue of a phenyl or naphthyl ring, each of r $R^{1d}$s and s $R^{2d}$s independently represents a hydrocarbon group having 1 to 18 carbon atoms, an alkoxy group having 1 to 18 carbon atoms or a hydroxy group, each of r and s represents an integer of 0 to 5, $A^{1d}$ represents a divalent hydrocarbon group that has 1 to 20 carbon atoms and may have hydrogen atoms therein substituted by, at least one of two ends thereof interrupted by, or carbon-carbon bonds therein interrupted by a monovalent or divalent group(s) selected from an aromatic group, an unsaturated group, a nitrogen-containing group, a sulfur-containing group, an oxygen-containing group, a phosphorus-containing group, an alicyclic group and a halogen atom.

2. The light-resistant ultraviolet absorber according to claim 1, wherein the 2-phenylbenzotriazole derivative is represented by any one of the formulae (1), (3) and (4), $X^{1a}$, $X^{1c}$, $X^{2c}$, $X^{1d}$ and $X^{2d}$ in the formulae (1), (3) and (4) represent residues of phenyl rings, each of the l $R^{1a}$s, n $R^{1c}$s, p $R^{2c}$s, r $R^{1d}$s and s $R^{2d}$s independently represents a tertiary and/or quaternary carbon-containing alkyl group having 3 to 8 carbon atoms, each of l, n, p, r and s represents an integer of 1.

3. The light-resistant ultraviolet absorber according to claim 1, wherein $X^{1a}$, $X^{1c}$, $X^{2c}$, $X^{1d}$ and $X^{2d}$ in the formulae (1), (3) and (4) represent residues of phenyl rings, each of the l $R^{1a}$s, n $R^{1c}$s, p $R^{2c}$s, r $R^{1d}$s and s $R^{2d}$s independently represents a linear or branched alkyl group having 1 to 4 carbon atoms, each of l, n, p, r and s represents an integer of 2, and a total number of the carbon atoms in these alkyl groups is 2 to 5.

4. The light-resistant ultraviolet absorber according to claim 1, wherein the 2-phenylbenzotriazole derivative is represented by any one of the formulae (1), (3) and (4), $X^{1a}$, $X^{1c}$, $X^{2c}$, $X^{1d}$ and $X^{2d}$ in the formulae (1), (3) and (4) represent residues of phenyl rings, each of the l $R^{1a}$s, n $R^{1c}$s, p $R^{2c}$s, r $R^{1d}$s and s $R^{2d}$s independently represents an alkoxy group possessing a linear or branched alkyl group having 1 to 18 carbon atoms, and wherein l represents an integer of 1 to 3.

5. The light-resistant ultraviolet absorber according to claim 1, wherein the 2-phenylbenzotriazole derivative is represented by the formula (3); in the formula (3), $X^{1c}$ and $X^{2c}$ represent residues of phenyl rings, q represents 1, $A^{2c}$ represents a sulfide group —S—.

6. The light-resistant ultraviolet absorber according to claim 1, wherein the 2-phenylbenzotriazole derivative is represented by the formula (3); in the formula (3), $X^{1c}$ and $X^{2c}$ represent residues of phenyl rings, q represents 1, $A^{2c}$ represents a hydrocarbon group having 1 to 8 carbon atoms.

7. The light-resistant ultraviolet absorber according to claim 1, wherein the 2-phenylbenzotriazole derivative is represented by the formula (3); in the formula (3), $X^{1c}$ and $X^{2c}$ represent residues of phenyl rings, q represents 0.

8. An organic resin composition comprising:
    the light-resistant ultraviolet absorber according to claim 1; and
    an organic resin.

9. The organic resin composition according to claim 8, wherein the organic resin is a polymer or copolymer of a thermoplastic resin.

10. The organic resin composition according to claim 8, wherein the organic resin is a polymer or copolymer of a thermosetting resin.

*   *   *   *   *